US012702705B2

(12) United States Patent
Adamo et al.

(10) Patent No.: US 12,702,705 B2
(45) Date of Patent: Aug. 11, 2026

(54) CARBOCYCLIC DERIVATIVES AND CONJUGATED DERIVATIVES THEREOF, AND THEIR USE IN VACCINES

(71) Applicant: GLAXOSMITHKLINE BIOLOGICALS SA, Rixensart (BE)

(72) Inventors: Roberto Adamo, Siena (IT); Francesco Berti, Siena (IT); Paolo Costantino, Milan (IT); Luigi Lay, Milan (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 900 days.

(21) Appl. No.: 17/436,692

(22) PCT Filed: Mar. 6, 2020

(86) PCT No.: PCT/EP2020/055950

§ 371 (c)(1),
(2) Date: Sep. 7, 2021

(87) PCT Pub. No.: WO2020/182635

PCT Pub. Date: Sep. 17, 2020

(65) Prior Publication Data

US 2022/0152183 A1 May 19, 2022

(30) Foreign Application Priority Data

Mar. 8, 2019 (EP) .................................... 19161716

(51) Int. Cl.

*A61K 39/095* (2006.01)
*A61K 39/00* (2006.01)

(Continued)

(52) U.S. Cl.

CPC .......... *A61K 39/095* (2013.01); *A61K 39/385* (2013.01); *A61K 47/6415* (2017.08);

(Continued)

(58) Field of Classification Search

CPC ................ A61K 39/095; A61K 39/385; C08B 37/0006; C08G 79/02

See application file for complete search history.

(56) References Cited

U.S. PATENT DOCUMENTS 8,753,651 B2 * 6/2014 Costantino ............. A61P 43/00 424/278.1
8,889,152 B2 * 11/2014 Costantino ............. A61P 43/00 424/282.1

(Continued)

FOREIGN PATENT DOCUMENTS

CN 1976724 A 6/2007
WO 2020030782 A1 2/2020

OTHER PUBLICATIONS

Harale et al., "Synthesis of a tetrasaccharide and its glycoconjugate corresponding to the capsular polysaccharide of Neisseria meningitidis serogroup X and its immunochemical studies" RSC Advances vol. 5 pp. 41332-41340, DOI:10.1039/c5ra02993g (Year: 2015).*

(Continued)

*Primary Examiner* — Andrea Olson

(57) ABSTRACT

The invention is in the field of vaccines and relates to oligomers having a selected degree of polymerization, obtained by connecting together a number of carbocyclic repeating units, and to conjugated derivatives thereof. The oligomers and conjugated derivatives thereof of the invention also have a selected degree of acetylation. The derivatives of the invention are useful for the preparation of immunogenic compositions, e.g. in the form of a vaccine.

24 Claims, 10 Drawing Sheets

(51) Int. Cl.
*A61K 39/385* (2006.01)
*A61K 47/64* (2017.01)
*C08B 37/00* (2006.01)

(52) U.S. Cl.
CPC ........ *A61K 47/646* (2017.08); *C08B 37/0006* (2013.01); *A61K 2039/6037* (2013.01)

(56) References Cited

U.S. PATENT DOCUMENTS

| | | | | |
|---|---|---|---|---|
| 8,895,516 | B2* | 11/2014 | Giannozzi | A61P 25/00 514/23 |
| 10,272,147 | B2 | 4/2019 | Costantino | |
| 10,668,142 | B2 | 6/2020 | Costantino | |
| 2008/0241180 | A1 | 10/2008 | Contorni | |
| 2015/0004191 | A1 | 1/2015 | Contorni | |
| 2023/0346905 | A1* | 11/2023 | Adamo | A61P 31/04 |

OTHER PUBLICATIONS

Lemercinier et al., "Full 'H NMR assignment and detailed O-acetylation patterns of capsular polysaccharides from Neisseria Meningitidis used in vaccine production" Carbohydrate Research vol. 296 pp. 83-96 (Year: 1996).*

Gudlavalleti et al., "In vivo determination of Neisseria meningitidis serogroup A capsular polysaccharide by whole cell high-resolution magic angle spinning NMR spectroscopy" Carbohydrate Research vol. 341 pp. 557-562, doi: 10.1016/j.carres.2005.11.036 (Year: 2006).*

Berry, D.S., et al., "Effect of O Acetylation of Neisseria meningitidis Serogroup A Capsular Polysaccharide on Development of Functional Immune Responses." Infection and Immunity; Jul. 1, 2002; pp. 3707-3713; vol. 70(7).

Berti, F., et al., "Relative stability of meningoccal serogroup A and X polysaccharides." Vaccine; Aug. 22, 2012; pp. 6409-6415; vol. 30(45).

Gao, Qi, et al., "Immunoactivity of Protein Conjugates of Carba Analogues from Neisseria meningitidis A Capsular Polysaccharide." ACS Chemical Biology; Sep. 19, 2013; pp. 2561-2567; vol. 8(11).

Hlozek, et al., "Conformations of Neisseria meningitidis serogroup A and X polysaccharides: The effects of chain length and O-acetylation" Carbohydrate Research; Jul. 1, 2018; pp. 44-51; vol. 465.

Berry, D.S., et al., "Effect of O Acetylation of Neisseria meningitidis Serogroup A Capsular Polysaccharide on Development of Functional Immune Responses." Infection and Immunity; Jul. 2002; pp. 3707-3713; vol. 70(7).

Gao, Qi, et al., "Immunoactivity of Protein Conjugates of Carba Analogues from Neisseria meningitidis A Capsular Polysaccharide." ACS Chemical Biology; Nov. 15, 2013; pp. 2561-2567; vol. 8(11) (Epub Sep. 3, 2013).

Hlozek, et al., "Conformations of Neisseria meningitidis serogroup A and X polysaccharides: The effects of chain length and O-acetylation" Carbohydrate Research; Jul. 30, 2018; pp. 44-51; vol. 465 (Epub Jun. 22, 2018).

International Search Report and Written Opinion in corresponding International Patent Application No. PCT/EP2020/055950, mailed Jun. 4, 2020 (13 pages).

Greene T.W., et al., "Protective Groups in Organic Synthesis," A Wiley-Interscience Publication John Wiley & Sons, Inc, New York, 1999, Chapter 9, pp. 660-674, (20 Pages).

Berti F., et al., "Role of O-acetylation in the Immunogenicity of Bacterial Polysaccharide Vaccines," Molecules, 2018, vol. 23, 1340, pp. 1-10, Retrieved from [doi:10.3390/molecules23061340].

Co-pending U.S. Appl. No. 18/869,582, inventors Agnese; Marcelli et al., filed Nov. 26, 2024 (a 371 of international application PCT/EP2023/064448, filed on May 30, 2023).

International Search Report for International Application No. PCT/EP2021/073217, mailed Jan. 28, 2022, 7 Pages.

* cited by examiner

Post II

Anti Meningococcal A PS IgG (GMT 95% CI)

10000
1000
100
10
1

MenA–CRM Native
carbaMenA DP6OAc–CRM
carbaMenA DP8OAc–CRM
carbaMenA DP6–CRM
carbaMenA DP8–CRM

**
*
***

Legend:

-square symbol=titer of the pool from each Group;

-titer 8 assigned to non-responder samples (<16);

-Mann-Whitney test used for stat elaboration.

full liquid formulation stability study (Alum 10mM NaPi pH6.5)

FS %

100.0
90.0
80.0
70.0
60.0
50.0
40.0
30.0
20.0
10.0
0.0

0
5
10
15
20
25
30

Time days

MenA-CRM in Alum @ 37°C
CarbaMenA OAc DP7-CRM in Alum @ 37°C

CARBOCYCLIC DERIVATIVES AND CONJUGATED DERIVATIVES THEREOF, AND THEIR USE IN VACCINES

CROSS-REFERENCE TO RELATED APPLICATIONS

This application is filed pursuant to 35 U.S.C. § 371 as a United States National Phase Application of International Application No. PCT/EP2020/055950 filed 6 Mar. 2020 which claims priority from EP19161716.6, filed 8 Mar. 2019.

FIELD OF THE INVENTION

The invention is in the field of vaccines, and it relates to oligomers having a selected degree of polymerization, obtained by connecting together a number of carbocyclic repeating units, and to conjugated derivatives thereof. The oligomers and conjugated derivatives thereof of the invention also have a selected degree of acetylation. The derivatives of the invention are useful for the preparation of immunogenic compositions, e.g. in the form of a vaccine.

BACKGROUND OF THE INVENTION

*Neisseria meningitidis* is a leading cause of bacterial meningitis and sepsis worldwide, capable of causing outbreaks and epidemics of invasive disease. Invasive meningococcal disease occurs worldwide. Although incidence varies in different regions of the world, infants, children, and adolescents are the most vulnerable to developing invasive disease. Symptoms of the disease progress rapidly and often result in devastating outcomes. Based on antigenic differences in their capsular polysaccharide, 12 serogroups of *N. meningitidis* have been identified. Virtually all disease-associated isolates are encapsulated, with serogroups A, B, C, W, X and Y being responsible for over 90% of invasive meningococcal infections worldwide. The distribution of these serogroups varies geographically and temporally.

In general, the *Neisseria meningitidis* capsular polysaccharides (CPSs) are T-cell independent antigens, which means that they can give an immune response without the involvement of T-cells. This response lacks several important properties that characterize the T-cell dependent immune response, such as immunological memory, class switch from IgM to IgG, and affinity maturation. If the polysaccharide part is connected to a carrier protein, however, it triggers cellular immune response that creates memory effect, and also gives protection in young children. Such polysaccharide linked to a carrier protein are often referred to as glycoconjugates and are especially valuable as vaccines. In this respect, especially efficient vaccines (glycoconjugate vaccines) can be made by attaching the saccharide to a carrier protein through a linker moiety (or spacer) or even by direct coupling of the saccharide with the selected carrier protein. In any case, the glycoconjugates can induce a T-cell dependent immune response with memory and effect also in young children, while the non-conjugated CPS generally fails to provide either a memory effect in adults or any substantial immunogenic effect in infants.

Among the *Neisseria meningitidis* capsular polysaccharides, the *Neisseria meningitidis* serogroup A capsular polysaccharide (MenA CPS) is known to suffer from inherent chemical instability in water (see e.g. Frasch et al. Adv. Biotechnol. Processes, 1990, 12, 123-145). The MenA CPS is composed of (1→6)-linked 2-acetamido-2-deoxy-α-D-mannopyranosyl phosphate repeating units and the hydrolysis instability of MenA polysaccharide is mainly due to the ring oxygen and N-acetamide promoted hydrolysis on the phosphodiester linkage. It has in fact been observed that both the oxygen in the ring and N-acetyl group destabilize the phosphodiester glycosidic linkage and the axial position of NHAc also contributes to this mechanism as indicated in the below reported Scheme A (Berti et al. Vaccine, 2012, 30, 6409-6415):

Scheme A

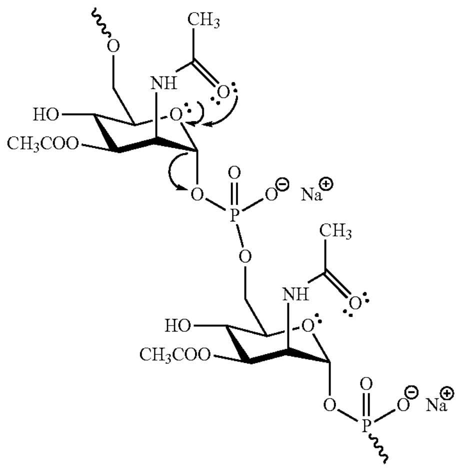

The availability of MenA polysaccharide mimics resistant to hydrolysis is very attractive for the development of more stable conjugate vaccines. Stabilization of the CPS can be achieved in different ways, and MenA CPS analogues in which the ring-oxygen is replaced by a methylene group, have been reported in the prior art. In particular in this respect, when the oxygen in the ring is replaced by a carbon, the destabilization described in Scheme A is prevented as provided in Scheme B:

Scheme B

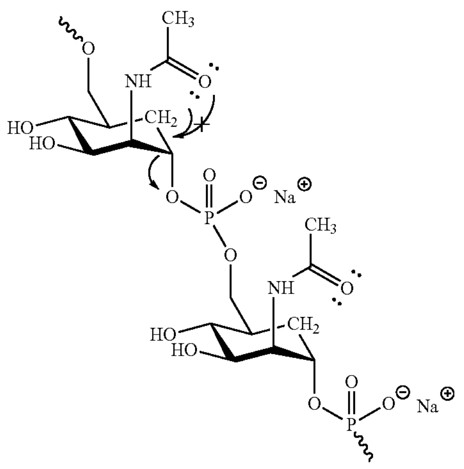

Toma et al. Org. Biomol. Chem., 2009, 7, 3734-3740 describe the preparation of the monomer 0-(2-acetamido-2-deoxy-5a-carba-α-D-mannopyranosyl)phosphate, where a methylene group replaces the pyranose oxygen of the repeating unit of the MenA CPS. The publication refers to the chemical synthetic preparation of the monomer itself, only.

Gao et al. (Org. Biomol. Chem. 2012, 10(33), 6673, and ACS Chem. Biol. 2013, 8(11), 2561) and Ramella D. et al. (Eur J. Org. Chem, 2014, 5915-5924) describes the stabilization of the glycosyl 1-0-phosphates by using carbasugars, where a methylene group replaces the pyranose oxygen atom. They also report the conjugation of the synthetic carba-trimer to a protein carrier, without however further investigating the behaviour of carba-analogues having a higher degree of polymerization. There is also no mention of a carba-analogue, which has a specific level of acetylation and/or specific acetylation pattern. Even further, the trimer considered showed poor potential in inhibiting the binding of anti-MenA CPS antibodies, indicating the described derivatives to be relatively poor synthetic antigens.

Thus, there is a need to find carba analogue polysaccharide derivatives having good stability and also exhibiting a good immunogenic profile, obtainable following a reliable and convenient synthetic approach, and suitable for the preparation of a vaccine, preferably to be formulated in liquid form, against meningitis.

SUMMARY OF THE INVENTION

In a first aspect, the invention relates to an oligomer of Formula (Ia) or (Ib):

(Ia)

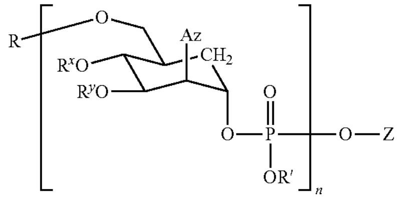

or (Ib)

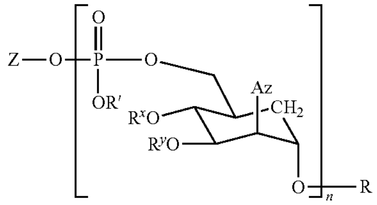

wherein n is ≥6;

R is H or —P(O)(OR")$_2$, wherein R" is H or a pharmaceutically acceptable phosphate counterion;

R' is H or a pharmaceutically acceptable phosphate counterion;

$R^x$ is H or —C(O)$CH_3$ and may be the same or different in each repeat unit;

$R^y$ is H or —C(O)$CH_3$ and may be the same or different in each repeat unit;

wherein at least one of $R^x$ or $R^y$ is —C(O)$CH_3$ in at least one repeat unit, and wherein, taken together, about 50 to 90% of $R^x$ and $R^y$ in the oligomer is —C(O)$CH_3$;

Az is an aza substituent selected from the group consisting of —NH(CO)$R^1$, —N($R^1$)2 and —$N_3$, wherein $R^1$ is independently selected from the group consisting of H, a linear or branched $C_1$-$C_6$-alkyl and a linear or branched $C_1$-$C_6$-haloalkyl;

Z is (i) a protecting group, (ii) a functional linker for conjugation to a protein, or (iii) a linear or branched $C_1$-$C_6$ alkyl, optionally substituted phenyl, —C(O)Y, or a linear or branched $C_1$-$C_6$-alkyl-X, wherein Y is H, a linear or branched $C_1$-$C_6$-alkyl or a protecting group, and wherein X is —$NH_2$, —$N_3$, —C≡CH, —CH═$CH_2$, —SH or —S—C≡N.

In a second aspect, the invention relates to an oligomer conjugate antigen of Formula (IIa) or (IIb):

(IIa)

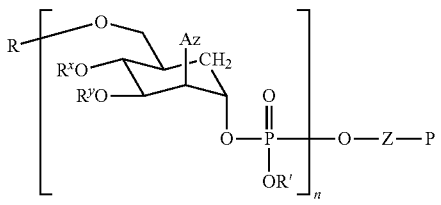

or (IIb)

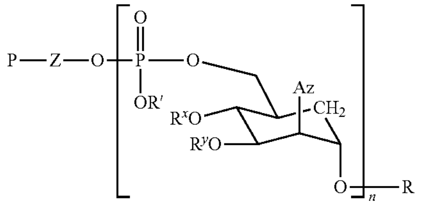

wherein n, R, R', $R^x$ and $R^y$ are as defined above in connection with the first aspect;

Z is a linker or a bond; and

P is a protein.

In a third aspect, the invention relates to an immunogenic composition comprising (a) a conjugate as described above according to the second aspect of the invention; and (b) at least one pharmaceutically acceptable excipient.

In a fourth aspect, the invention relates to a vaccine comprising a conjugate as described above according to the second aspect of the invention, or an immunogenic composition as described above according to the third aspect of the invention.

In a fifth aspect, the invention relates to a method for the treatment or prevention of Meningitis A, C, W135 or Y in a subject, the method comprising administering to the subject a therapeutically or prophylactically effective amount of a conjugate according to the second aspect of the invention, or an immunogenic composition according to the third aspect of the invention, or a vaccine according to the fourth aspect of the invention.

In a sixth aspect, the invention relates to a method of immunizing against Meningitis A, C, W135 or Y in a subject, the method comprising administering to the subject an immunologically effective amount of the immunogenic composition according to the third aspect of the invention, or vaccine according to the fourth aspect of the invention.

In a seventh aspect, the invention relates to a method of inducing an immune response to Meningitis A, C, W135 or Y in a subject, the method comprising administering to the subject an immunologically effective amount of the immunogenic composition according to the third aspect of the invention, or vaccine according to the fourth aspect of the invention.

In an eighth aspect, the invention relates to the use of the immunogenic composition according to the third aspect of the invention, or vaccine according to the fourth aspect of the invention in the manufacture of a medicament for the treatment or prevention of Meningitis A, C, W135 or Y.

In a ninth aspect, the invention relates to an immunogenic composition according to the third aspect of the invention, or vaccine according to the fourth aspect of the invention, for use in the treatment of prevention of Meningitis A, C, W135 or Y.

In a tenth aspect, the invention relates to an immunogenic composition according to the third aspect of the invention, or vaccine according to the fourth aspect of the invention, for use in inducing an immune response to Meningitis A, C, W135 or Y.

DETAILED DESCRIPTION OF THE INVENTION

Figure 1:
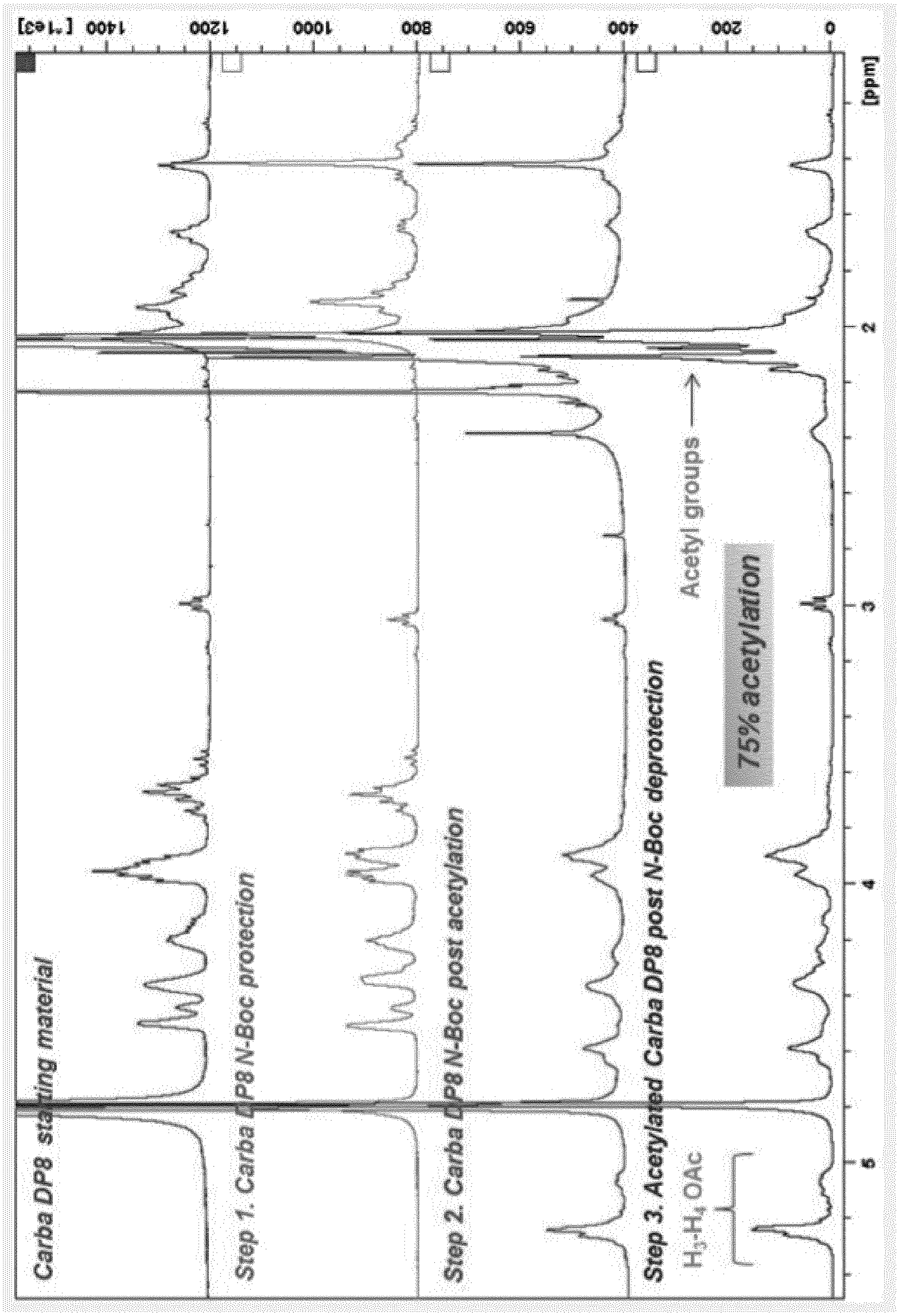
FIG. 1 is a $^{1}$H-NMR spectrum monitoring of the three reaction steps for random O-acetylation of carba-analogue DP8, i.e. Formula (Ia) where n=8.

To facilitate an understanding of the present invention, a number of terms and phrases are defined below. Art-recognized synonyms or alternatives of the following terms and phrases (including past, present, etc. tenses), even if not specifically described, are contemplated.

As used in the present disclosure and claims, the singular forms "a," "an," and "the" include plural forms unless the context clearly dictates otherwise; i.e., "a" means "one or more" unless indicated otherwise.

The term "and/or" as used in a phrase such as "A and/or B" is intended to include "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless specified otherwise, all of the designations "A %-B %," "A-B %," "A % to B %," "A to B %," "A %-B," "A % to B" are given their ordinary and customary meaning. In some embodiments, these designations are synonyms.

The terms "substantially" or "substantial" mean that the condition described or claimed functions in all important aspects as the standard described. Thus, "substantially free" is meant to encompass conditions that function in all important aspects as free conditions, even if the numerical values indicate the presence of some impurities or substances. "Substantial" generally means a value greater than 90%, preferably greater than 95%, most preferably greater than 99%. Where particular values are used in the specification and in the claims, unless otherwise stated, the term "substantially" means with an acceptable error range for the particular value.

An "effective amount" means an amount sufficient to cause the referenced effect or outcome. An "effective amount" can be determined empirically and in a routine manner using known techniques in relation to the stated purpose.

By "immunologically effective amount" or "therapeutically effective amount", it is meant that the administration of that amount to an individual, either in a single dose or as part of a series, is effective for treatment or prevention. This amount can vary depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

The term "treatment" means any one of more of the following: (i) the prevention of infection or re-infection, as in a traditional vaccine, (ii) the reduction in severity of, or, in the elimination of symptoms, (iii) the delay in recurrence of symptoms, and (iv) the substantial or complete elimination of the pathogen or disorder in question in a subject. Hence, treatment may be affected prophylactically (prior to infection) or therapeutically (following infection).

The term "% w/w" indicates the weight percentage of a given compound, over a different compound or over the whole content of a composition, as indicated.

Analogously, the term "% v/v" indicates the volume percentage of a given compound, over a different compound or over the whole content of a composition, as indicated.

The term "oligosaccharide" comprises in its meaning polysaccharides having from 3 to 10 monosaccharide units, as generally known in the art (see e.g. https://en.wikipedia.org/wiki/Oligosaccharide).

The term "oligomer" refers to carba-analogue polysaccharides, where the endocyclic oxygen has been replaced by a methylene (—CH2-) group, thus providing a cyclohexane backbone.

"Degree of Polymerization" (DP) indicates the number of monomers connected together to provide the final oligomer. In the present invention, unless otherwise provided, the DP is represented by "n" in the formulae (I) and (II).

"Average Degree of Polymerization" (avDP) indicates the average number of repeating units composing the oligomer.

The term "capsular polysaccharides/saccharides" (CPSs) indicates those saccharides which can be found in the layer that lies outside the cell envelope of bacteria, thus being part of the outer envelope of the bacterial cell itself. CPSs are expressed on the outermost surface of a wide range of bacteria, and in some cases even in fungi.

Unless otherwise provided, the term "conjugation" indicates the connection or linkage of the subjected entities, particularly the oligomers of the invention having n (i.e. DP) and the selected protein.

As used herein, the term "alkyl" represents a saturated, straight, or branched hydrocarbon moiety. The term "$C_1$-$C_6$-alkyl" refers to an alkyl moiety containing from 1 to 6 carbon atoms.

As used herein, the term "haloalkyl" represents a saturated, straight, or branched hydrocarbon moiety where one or more of the hydrogen atoms has been replaced with a halogen atom. In particular, reference to "haloalkyl" is a reference to "fluoroalkyl", i.e. wherein the halogen is fluoro. The term "$C_1$-$C_6$-haloalkyl" refers to an alkyl moiety containing from 1 to 6 carbon atoms wherein one or more of the hydrogen atoms has been replaced with a halogen atom. Examples include —$CF_3$, —$CH_2F$, —$CH_2CF_3$ and so on.

As used herein, particularly according to the definition of Z, phenyl may be optionally substituted. The phenyl group may be optionally substituted with one or more reactive functional groups to enable conjugation, such as $N_3$, $NH_2$, SH. Other suitable groups are well known by a person skilled in the art.

As used herein, the term "protecting group" is any suitable protecting group for the intended purpose. Selection and usage of such protecting groups and details of their usage are available in, for example, Greene, T. W. and Wuts, P. G. M., "Protective Groups in Organic Synthesis". Suitable protecting groups are well known by a person skilled in the art.

As used herein, the term "pharmaceutically acceptable phosphate counterion" is any counterion suitable for a phosphate group, i.e., a metal cation which is within the scope of sound medical judgment, suitable for use in contact with the tissues of human beings and animals without excessive toxicity, irritation, or other problem or complication, commensurate with a reasonable benefit/risk ratio. The pharmaceutically acceptable phosphate counterion may be a Group 1 or Group 2 metal. Particular examples of such a pharmaceutically acceptable phosphate counterion are sodium ($Na^+$) and potassium ($K^+$). It is preferred that the counterion is sodium, for example when the oligomer or conjugate of the invention is in buffer.

As described above, the invention relates to polysaccharide carba-analogues (i.e. where the ring oxygen of the mannosamine unit is replaced with a methylene) having a degree of polymerization of at least 6, having the first analogue monomer connected to the second analogue monomer through a 1,6 linkage which connects C-1 of the first unit to C-6 of the second unit, and wherein the 1,6-linkage comprises a phosphonate moiety. Of note, the derivatives of the invention are not only able to mimic the native polysaccharide from MenA serogroup, but they are also expected to have improved stability versus the native CPS.

In one embodiment, the oligomers of the invention are defined by Formula (Ia). In one embodiment, the oligomer conjugate antigens of the invention are defined by Formula (IIa).

As defined above, n is 6. In one embodiment, n is from 8 to 30. In another embodiment, n is from 8 to 20. In a particular embodiment, n is from 8 to 15. In one embodiment, n is 15. In particular, n is 8 or 10. In one embodiment, n is 8.

In one embodiment, R is H or —P(O)(OR")$_2$, wherein at least one R" is $Na^+$. In one embodiment, R is H.

In one embodiment, R' is $Na^+$, such that an oligomer of the invention is defined according to Formula (Ia') or (Ib'), preferably Formula (Ia'):

(Ia')

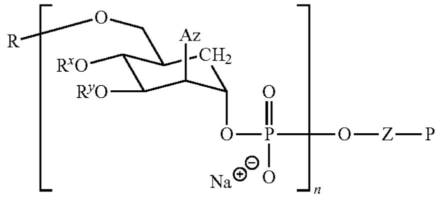

or (Ib')

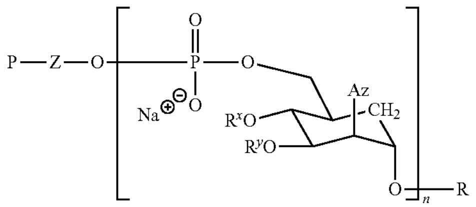

Therefore, it follows that in one embodiment, an oligomer conjugate antigen of the invention is defined according to Formula (IIa') or Formula (IIb'), preferably Formula (IIa'):

(IIa')

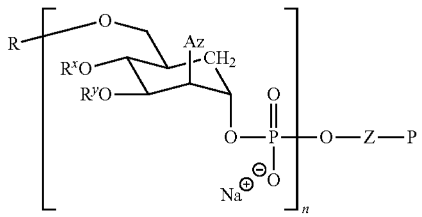

or (IIb')

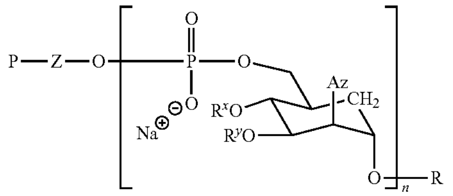

As defined above, $R^x$ is H or —C(O)$CH_3$ and may be the same or different in each repeat unit and $R^y$ is H or —C(O)$CH_3$ and may be the same or different in each repeat unit, wherein at least one of $R^x$ or $R^y$ is —C(O)$CH_3$ in at least one repeat unit and wherein taken together, about 50 to 90% of $R^x$ and $R^y$ in the oligomer is —C(O)$CH_3$. Thus, it should be understood that the formulae as defined inside the square brackets according to Formula (Ia), (IIa), (Ib) and (IIb), means that each unit of the oligomer has this backbone, but the monomer unit defined by the square brackets is not necessarily the same given that different options for $R^x$ and $R^y$ may be chosen for each repeat unit defined by the square brackets. It will therefore be appreciated that different % acetylation may be achieved, depending on n and the choice of H or —C(O)$CH_3$ for $R^x$ and $R^y$. For example, each repeat unit of the oligomer, defined by the square brackets, may be the same of different depending on the level of acetylation, i.e., depending on the choice of H or —C(O)$CH_3$ for each of $R^x$ and $R^y$.

As defined above, taken together, about 50 to 90% of $R^x$ and $R^y$ in the oligomer is —C(O)$CH_3$. In other words, the total amount of acetylation of the oligomer is about 50 to 90%. In other words, in the oligomers of the invention at least one of $R^x$ and one of $R^y$ is —C(O)$CH_3$ in a same or a different repeat unit, with the total of acetylation degree at 3 ($R^y$ is —C(O)$CH_3$) and 4 ($R^x$ is —C(O)$CH_3$) positions of about 50 to 90%. For the avoidance of doubt, as noted above, $R^x$ and $R^y$ may be the same or different in each repeat unit of the oligomer.

In another embodiment, taken together, about 60 to 80% of $R^x$ and $R^y$ in the oligomer is —C(O)$CH_3$. In other words, the total amount of acetylation of the oligomer is about 60 to 80%. For the avoidance of doubt, as noted above, $R^x$ and $R^y$ may be the same or different in each repeat unit of the oligomer.

In one embodiment, both of $R^x$ and $R^y$ are —C(O)$CH_3$ in at least one same repeat unit of the present oligomers, and preferably in about 40 to 50% of the repeat units of the oligomer; from about 10 to 30% of the remaining repeat units may have one of $R^x$ or $R^y$ that is —C(O)$CH_3$, the rest of the repeat units in the oligomer having $R^x$=$R^y$=H.

As defined above, Az is an aza substituent selected from the group consisting of —NH(CO)$R^1$, —N($R^1$)$_2$ and —$N_3$, wherein $R^1$ is independently selected from the group consisting of H, a linear or branched $C_1$-$C_6$-alkyl and a linear or branched $C_1$-$C_6$-haloalkyl. The nitrogen atom is directly attached to the carba-analogue repeat unit.

Examples of such Az substituents include —$N_3$, —$NH_2$, —NH—$C_1$-$C_6$ alkyl, —N—($C_1$-$C_6$ alkyl)$_2$ and —NH(CO)—$C_1$-$C_6$ alkyl. In one embodiment, the —$C_1$-$C_6$ alkyl is a —$C_1$-$C_4$ alkyl, in particular a —$CH_3$. Thus, according to one embodiment, Az is —NH(CO)—$C_1$-$C_6$ Alkyl, in particular-NH(CO)—$CH_3$, also indicated as —NHAc (where Ac denotes an acetate, i.e. —C(O)$CH_3$).

Z may have different meanings depending on whether or not the oligomers of the invention are conjugated or not to a protein.

According to Formula (Ia) or (Ib), an oligomer of the invention is not conjugated to a protein. Therefore, as defined above, according to Formula (Ia) or (Ib) Z is one of the following:

(i) a protecting group, (ii) a linear or branched $C_1$-$C_6$ alkyl, optionally substituted aryl, —C(O)Y, or a linear or branched $C_1$-$C_6$-alkyl-X, or (iii) a functional linker for conjugation to a protein.

Thus, according to one embodiment, Z is a means for capping the terminal saccharide unit, such that it may be unreactive or reactive, for example to further chain elongation or for subsequent modification.

When Z is intended to be a means for capping the terminal carba-analogue unit, it can comprise protecting groups or capping groups, such as a linear or branched $C_1$-$C_6$ alkyl, optionally substituted phenyl, —C(O)—Y, or a linear or branched —$C_1$-$C_6$ alkyl-X, wherein X is —$NH_2$, —$N_3$, —C≡CH, —CH=$CH_2$, —SH or —S—C≡N, and wherein Y is H, a linear or branched $C_1$-$C_6$-alkyl or a protecting group.

As defined herein, Z may be a functional linker for conjugation to a protein. In this case, "functional linker" refers to any linker known in the art to be used for conjugation of a saccharide to a protein.

In one embodiment, X is —$NH_2$.

In one embodiment, Z according to Formula (Ia) or (Ib) is selected from: —$(CH_2)_6$—$NH_2$, —$(CH_2)_4$—$NH_2$, —$(CH_2)_3$—$NH_2$ and —$(CH_2)_2$—$NH_2$, where the amino group is optionally protected by a suitable protecting group, e.g. —C(O)$CH_3$ (selection and usage of such protecting groups and details of their usage are available in. for example, Greene, T. W. and Wuts, P. G. M., "protective groups in organic synthesis").

The oligomers of the invention can be prepared following synthetic approaches known in organic synthesis for the preparation of polysaccharide carba-analogues. Generally, the preparation of the oligomers of the invention can be achieved by linking at least 6 mannosamine carba-analogue building blocks in a desired way by forming a 1,6-alpha linkage between the repeating units, thus providing an oligomer having a degree of polymerization of at least 6. As indicated in Formula (I), the monomers are linked through an alpha-(1→6) phosphate linkage, and such a connection can be performed using standard polymerization techniques, such as among others the one described in Gao et al., Org. Biomol. Chem., 2012, 10, 6673.

The mannosamine carba-analogue building blocks could bear an acetate at position 3 and/or 4 or a protective group that can be replaced with an acetate at any stage of the synthesis.

Alternatively, and according to one embodiment, the invention relates to a process for the preparation of the oligomers of Formula (I) comprising the steps of:

a. Preparation of the monomer having phosphodiester linkage;

b. Elongation reaction of the thus obtained monomer using, for example, phosphoramidite.

c. O-acetylation of the oligomer.

In one embodiment, when $R^y$ is C(O)$CH_3$, steps (b) and (c) may be the other way around such that O-acetylation is performed prior to the elongation reaction.

In more detail, the process may comprise the steps illustrated in Scheme 1:

Scheme 1 Process for the preparation of an oligosaccharide of the invention.

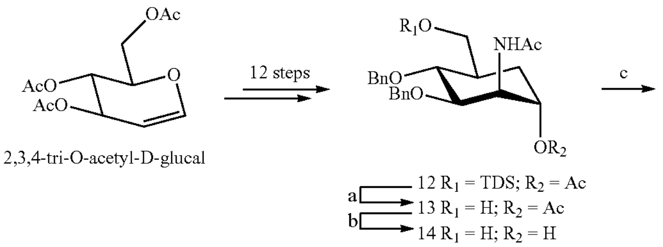

2,3,4-tri-O-acetyl-D-glucal

12 $R_1$ = TDS; $R_2$ = Ac

13 $R_1$ = H; $R_2$ = Ac

14 $R_1$ = H; $R_2$ = H

-continued
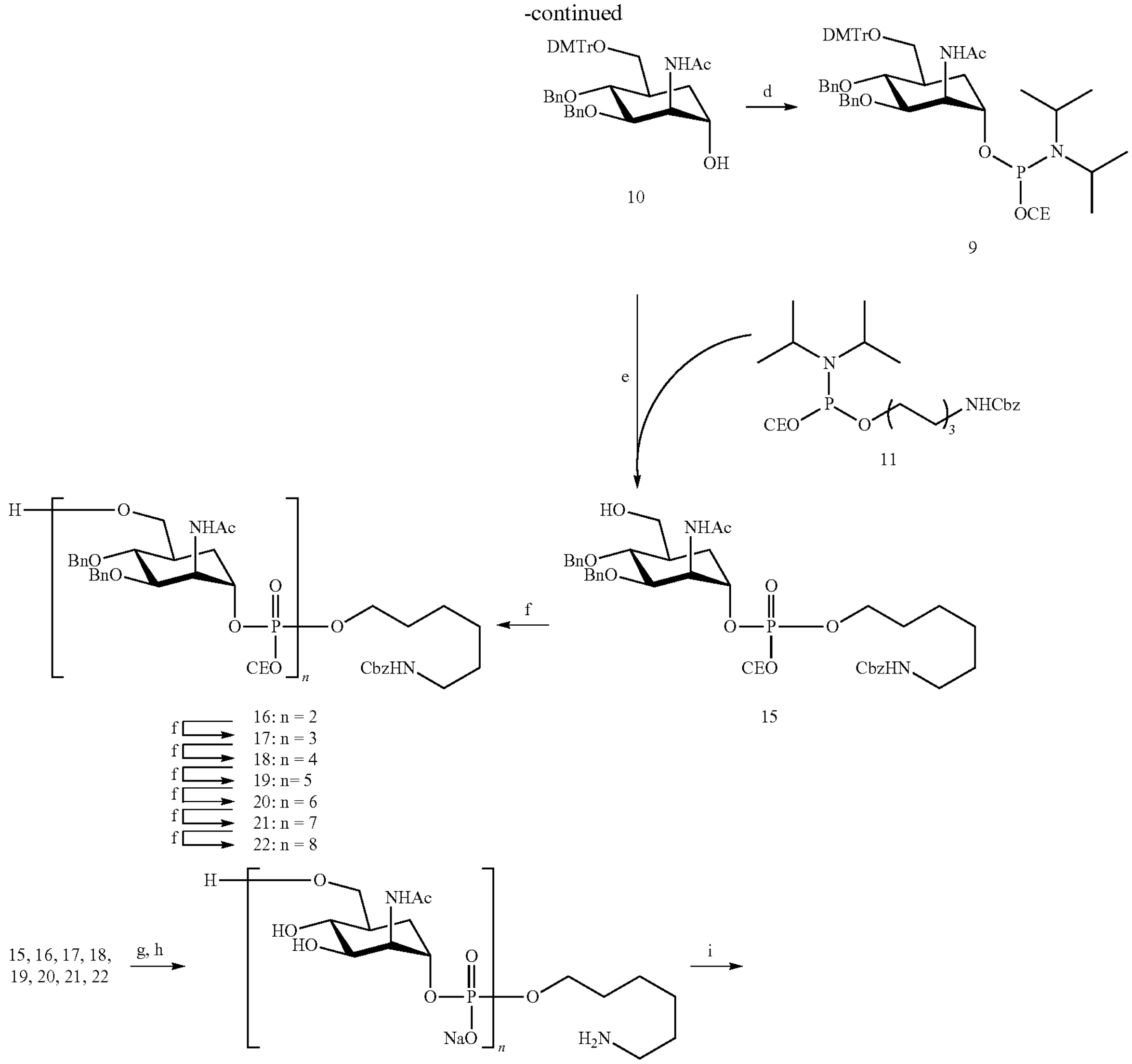
10
9
11
15
16: n = 2
17: n = 3
18: n = 4
19: n= 5
20: n = 6
21: n = 7
22: n = 8
15, 16, 17, 18, 19, 20, 21, 22
1: n = 1 2: n = 2
3: n = 3 4: n = 4
5: n = 5 6: n = 6
7: n = 7 8: n = 8
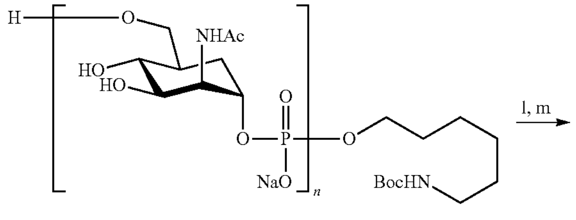
1a: n = 1 2b: n = 2
3c: n = 3 4d: n = 4
5e: n = 5 6f: n = 6
7g: n = 7 8h: n = 8

-continued

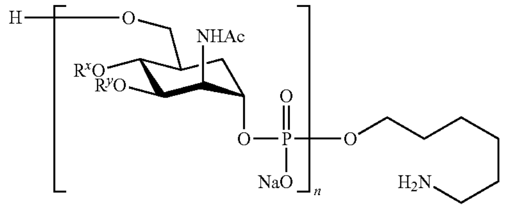

or

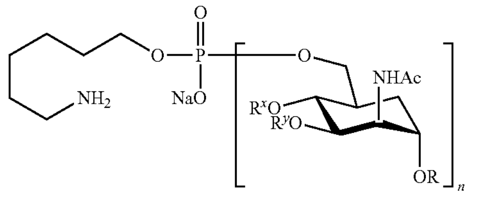

$R^x$ = H $R^y$ = Ac
$R^x$ = Ac, $R^y$ = H
$R^x$ = $R^y$ = Ac
1c: n = 1 2c: n = 2
3c: n = 3 4c: n = 4
5c: n = 5 6c: n = 6
7c: n = 7 8c: n = 8

$R^x$ = H $R^y$ = Ac
$R^x$ = Ac, $R^y$ = H
$R^x$ = $R^y$ = Ac
1d: n = 1 2d: n = 2
3d: n = 3 4d: n = 4
5d: n = 5 6d: n = 6
7d: n = 7 8d: n = 8

For the avoidance of doubt, Ac is intended to refer to an acetyl group, i.e. —$C(O)CH_3$.

(a) TBAF, THF, 0° C. → rt. 92%. (b) MeONa, MeOH, rt, 85%. (c) DMTrCl, $Et_3N$, DCM, rt, 91%.

(d) 2-cyanoethyl N,N-diisopropyl-chlorophosphormidite, N,N-diisopropylethylamine, DCM, rt, 9 (94%). (e) I, 11, DCI, MeCN, II. CSO, MeCN, III. TCA,DCM, $H_2O$, 94%. (f) I. 9, DCI, MeCN, II. CSO, MeCN, III. TCA, DCM, $H_2O$, $H_2O$, 16 (82%), 17 (95%), 18, (90%), 19 (92%), 20 (88%), 21 (86%), 22 (87%). (g) $NH_4OH$, $H_2O$, dioxane. (h) $H_2$, Pd black, $H_2O$, AcOH, 1 (99%), 2 (76%), 3 (69%), 4 (39%). 5 (88%), 6 (83%), 7 (77%), 8 (44%), (i): $(Boc)_2O$, $NaHCO_3$, rt, 16 h; (I): $Ac_2O$/imidazole, 40° C., ~9 d; (m); TFA, rt, 1 h.

In particular, the use of phosphoramidite building blocks is more effective for the formation of the phosphodiester linkages. We opted for the use of the dimethoxytrityl (DMTr) ether to temporarily mask the primary alcohol functions to be elongated. Each elongation step is based on the iteration of a three-step sequence, comprising the coupling of the phosphoramidite with the growing chain alcohol, oxidation of the intermediate phosphite to the corresponding phosphodiester and unmasking of the primary hydroxyl on the (n+1) oligomer. As illustrated in Scheme 1 the key building block 9 is obtained from intermediate 10, which in turn is derived in three steps from known carbasugar 12 (see e.g. Q. Gao et al. Org. Biomol. Chem., 2012, 10, 6673-6681). The latter carba mannose building block can be prepared from the commercially available 3,4,6-tri-O-acetyl-D-glucal according to prior art methodologies. Thus, the primary silyl ether and acetyl ester were removed from compound 12 by the consecutive action of tetrabutylammonium fluoride (TBAF) and NaOMe, to give diol 14 in 85% yield. Next the DMTr group regioselectively introduced providing alcohol 10 in 91% yield. This compound was converted into the elongation block phosphoramidite 9 by reaction with 2-cyanoethyl-N,N-diisopropyl-chlorophosphoramidite. With the building blocks in hand the target oligomers were assembled. The synthesis started with the installation of the aminohexanol spacer on alcohol 10 using known phosphoramidite 11. The building blocks were coupled in a two-step one pot reaction using dicyanoimidazole (DCI) as activator for activation of the phosphoramidite. Oxidation of the in situ formed phosphite was carried out with (1S)-(+)-(10-camphorsulfonyl)-oxaziridine (CSO). DCI ($pK_a$ 5.2) was preferred over the conventionally used tetrazole ($pK_a$ 4.9) because it is less acidic and suitable to be used in combination with the acid labile DMTr group. CSO was used instead of iodine because of its higher solubility in non-aqueous solvents such as acetonitrile. The crude phodiester product was treated with TCA to cleave the DMTr group. The product was purified by size-exclusion chromatography (Sephadex LH-20) giving spacer-equipped monomer 15 in 94% yield. The subsequent couplings were all performed following the procedure described above until reaching the desired degree of polymerization of 8 or higher. For elongation of the longer oligomers, a larger amount of the phosphoramidite 9 was used and the coupling reaction time was increased to ensure complete conversion of the alcohol. The yield for each elongation cycle was good to excellent, ranging between 82% and 95%. Octamer 22 was obtained in 40% overall yield starting from 10. Fragments 16-22 were deprotected using a two-steps sequence. First the cyanoethyl groups (CE) were removed using an aqueous ammonia solution (33%). Next, all remaining protecting groups (the benzyl ethers and carboxybenzyl carbamate) on the so-formed phosphodiesters were cleaved off by hydrogenolysis over palladium black, to give the target non-acetylated oligomers 1-8.

The non-acetylated oligomers 1-8 may be 0-acetylated in a random fashion at the 3- and/or 4-position, i.e. such that, taken together, about 50 to 90% of $R^x$ and $R^y$ in the oligomer is —$C(O)CH_3$. This may be achieved by (i) BOC-protecting the free amine group; (ii) 0-acetylation using, for example $Ac_2O$/imidazole; and (iii) deprotection to afford acetylated oligomers 1c-8c or 1d to 8d. Such acetylated oligomers may then be activated with a linker group such as bis-succinimidyl adipate (also known as SIDEA) and conjugated to a protein such as $CRM_{197}$.

Scheme 2. Process leading to the preparation of the 3-O-acetylated monomer building block

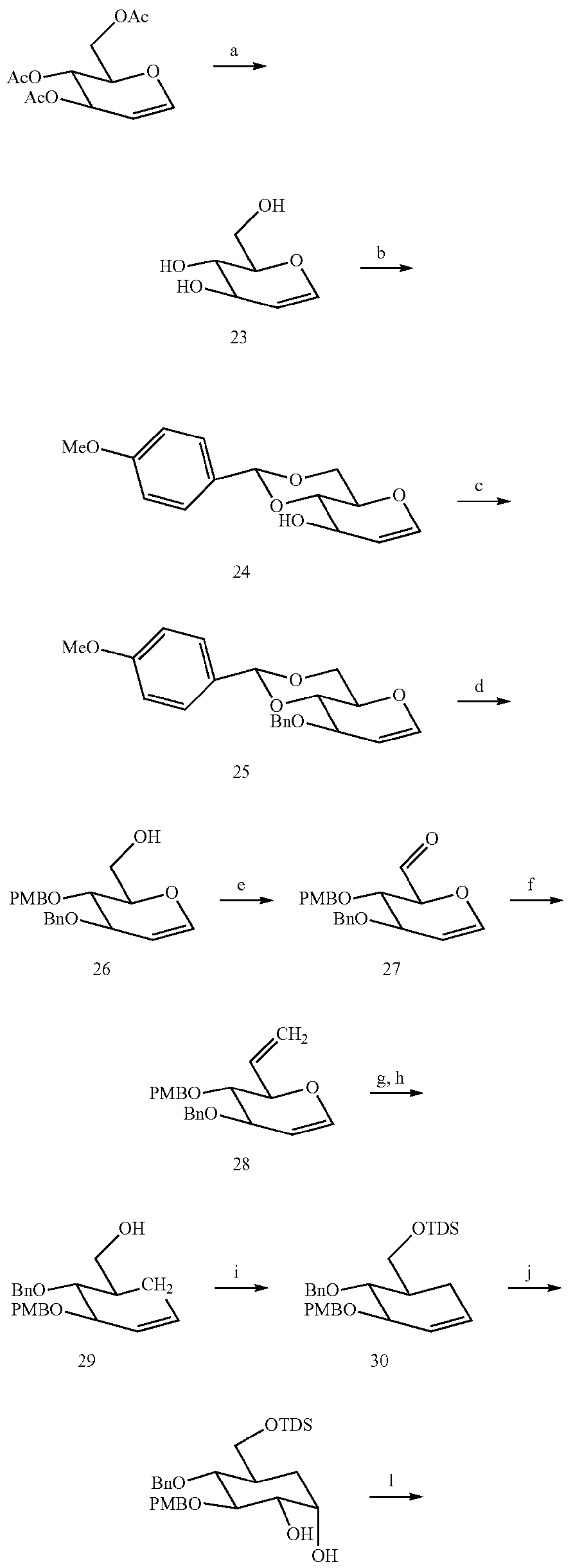

23 24 25 26 27 28 29 30 31

-continued

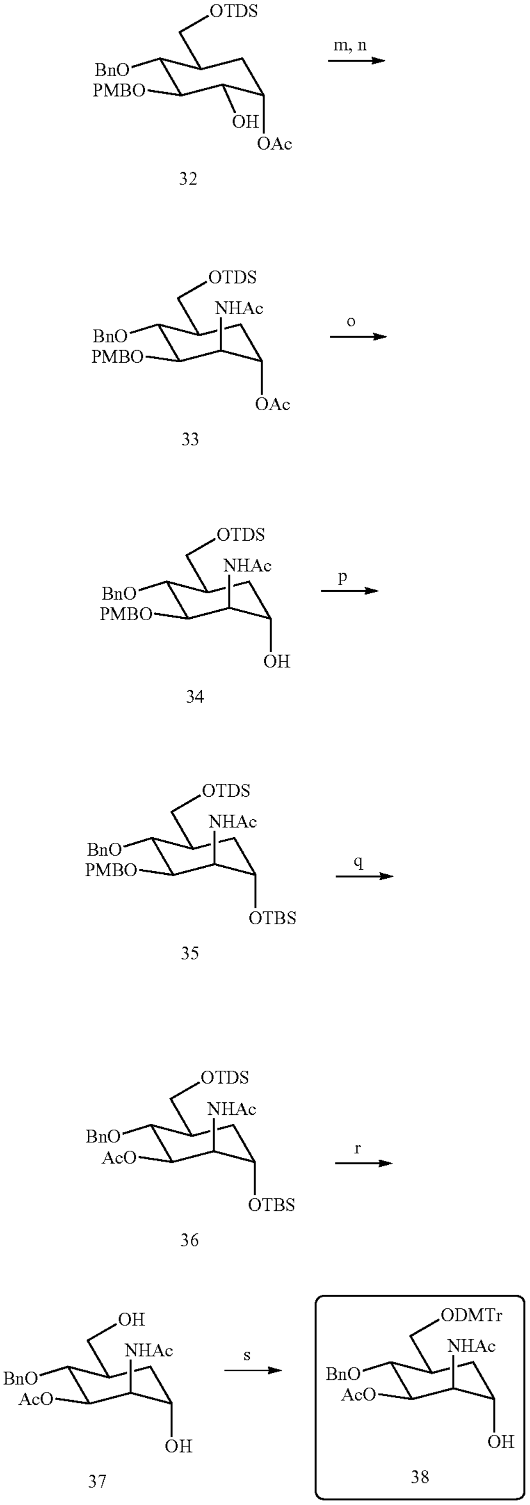

32 33 34 35 36 37 38

(a) $K_2CO_3$, MeOH; (b) $PMBCH(OMe)_2$, PPTS; (c) BnBr, NaH; (d)DIBAL—H, DCM; (e) DMP, DCM; (f) $PPh_3CH_3I$, KHMDS, THF, -78° C; (g) m_dichlorobenzene, t, μ-waves; (h) $NaBH_4$, EtOH/THF; (i) TDSCl, Im, DCM; (j) $OsO_4$, TMANO, 3:1 acetone-$H_2O$; (l) $(MeO)_3Cme$, PTSA, CAN, then 80% AcOH; (m) $Tf_2O$, DCM/py, -20° C. to rt; then $NaN_3$, 19:1 DMF—$H_2O$; (n) $PPh_3$, THF, 60° C. $H_2O$; then $Ac_2O$, MeOH; (o) NaOMe/MeOH; (p) TBSOTf, 2,6-lutidine, DCM; (q) DDQ, then $Ac_2O$, py; (r) HF/Pyridine, THF; (s) DMTrCl, pyridine, DCM.

In the alternative, 3-O-acetylated monomer building blocks and 4-O-acetylated building blocks can be prepared by a process depicted in the following Scheme 3:

Scheme 3. Process leading to the preparation of 3-O-acetylated and of 4-O-acetylated monomer building block

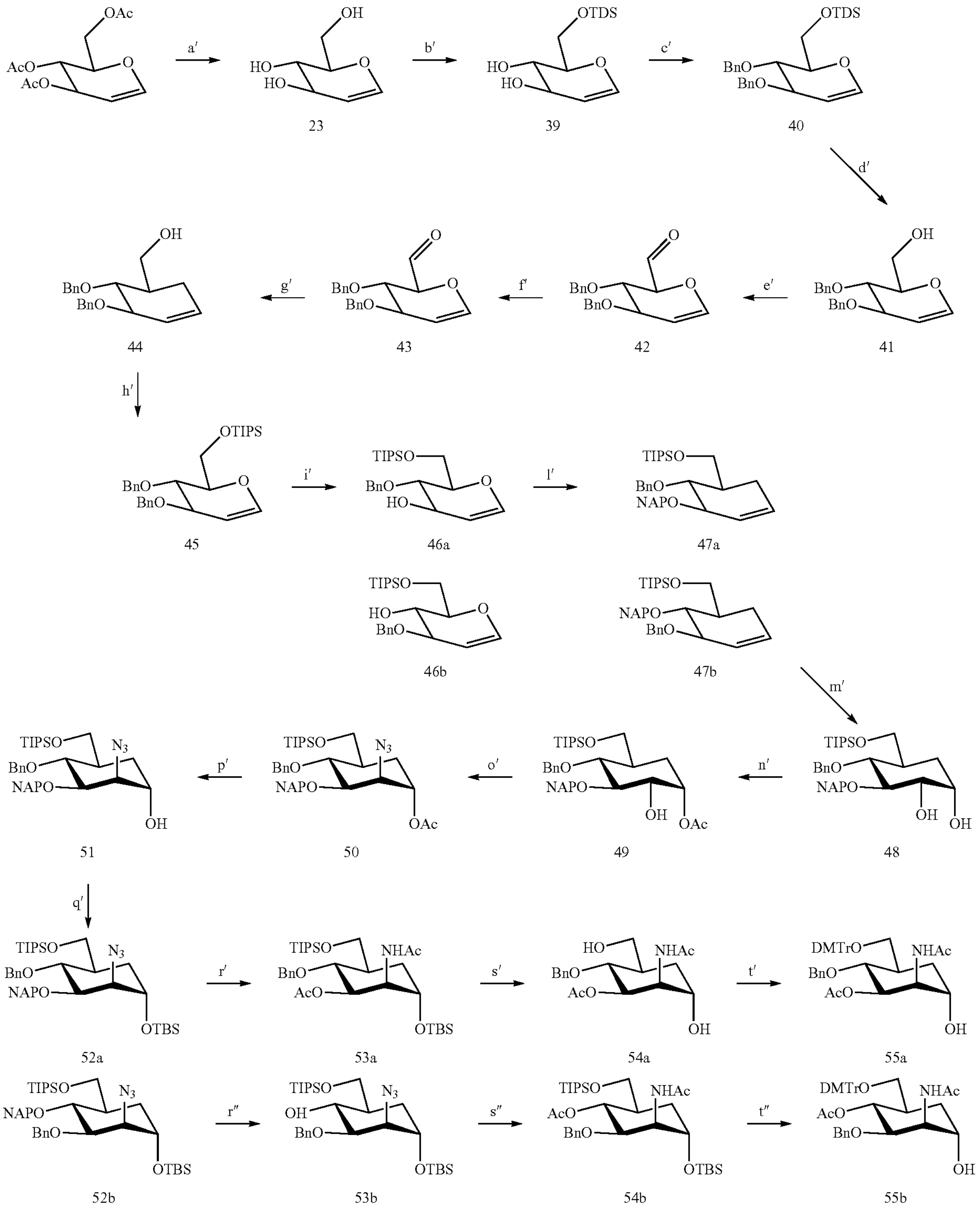

(a′) $K_2CO_3$, MeOH; (b′) TDSCl, imidazole, DMF, -30° C.; (c′) BnBr, NaH, DMF, 0° C.; (d′) TBAF, THF; (e′) IBX, AcOEt; (f′) $PPh_3CH_3I$, KHMDS, THF, -78° C. to rt; (g′) 1,3-dichlorobenzene, $NaBH_4$, EtOH/THF, 230° C.; (h′) TIPSCl, imidazole, DMF; (i′) $TiCl_4$, DCM/Toluene 2:8, -70° C.; (I′) NapBr, NaH, DMF, 0° C.; (m′) $Me_3NO$ $2H_2O$, acetone/$H_2O$ 3:1, $OsO_4$; (n′) $(MeO)_3CMe$, PTSA, ACN; (o′) $Tf_2O$, DCM/Py, -20° C. to rt; then $NaN_3$, 19:1 DMF—$H_2O$; (p′) NaOMe, MeOH; (q′) TBSOTf, -10°C. to 70° C., Pyr, DMAP; (r′) Pd/C, $H_2$, AcOH, then AcOH, then $Ac_2O$, Pyr; (s′) HF pyr, Pyr; (t′) DMTrCl, Pyr, 0° C.; (r″) DDQ, DCM, $H_2O$; (s″) $PPh_3$, $H_2O$, THF, then DMTrCl, Pyr.

Acetylated building blocks 38, 55a, 55b and fully acetylated building blocks (i.e. having O—Ac groups in both C3 and C4 positions of the same unit) may be converted to oligomeric versions by transformation to phosphorimidate and subsequent coupling as described above in relation to compound 9.

An important prerequisite for the immunogenicity of the carba analogues of the invention is their ability to mimic the corresponding MenA capsular saccharide. To investigate this, competitive ELISA were performed using carba analogues with different degrees of polymerization.

The oligomers of the invention can be introduced into a host, including a mammalian host and preferably a human host, either alone or linked to a carrier protein or as homopolymer or heteropolymer of mannose carba-analogue units. In a particular embodiment, oligomers of the invention are used as protein conjugates. Thus, in a further aspect, the invention comprises a conjugate derivative comprising the oligomers of the present invention of Formula (I), connected to a protein, according to general Formula (IIa) or (IIb):

(IIa)

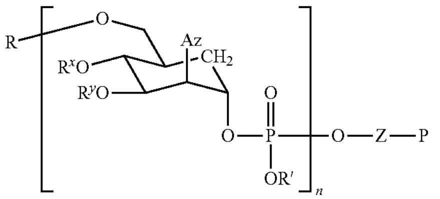

or (IIb)

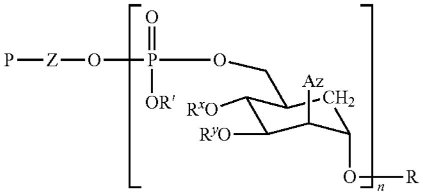

wherein n, R, R', $R^x$ and $R^y$ are as defined above;

Z is a linker or a bond; and

P is a protein.

The oligomers of general Formula (Ia) or (Ib) are especially useful when conjugated to a protein, preferably through the Z moiety connected to the C-1 carbon of the first repeating unit through a phosphate moiety. The thus obtained oligomer-protein conjugated derivatives of Formula (IIa) or (IIb) are potentially useful for the preparation of compositions able to elicit immunogenic responses in infants, and also possibly able to elicit cellular responses that provide a memory effect to prolong the effectiveness of the vaccination.

In one embodiment, the oligomer conjugate is preferably defined by Formula (IIa), i.e. where the protein is conjugated at the 1-position rather than the 6-position of the carba analogue.

The protein (or carrier protein) may influence the immunogenic response and even affect the precise nature of the antibodies that result from treatment of a mammal with one or more compounds of the invention when delivered as conjugates. Suitable proteins are those having functional groups able to react with the terminal portion of the Z moiety, thus forming the conjugate derivatives of the invention. Preferably, said functional groups are selected from $—NH_2$ and —SH, able to be connected to the Z moiety forming an amide bond or a thioether. More preferably, the protein has $—NH_2$ groups, suitable for the formation of an amide bond when reacted with Z.

Useful proteins are well known in the art. However, in one embodiment, P is an inactivated bacterial toxin selected from diphtheria toxoid (DT), tetanus toxoid (TT), $CRM_{197}$, *E. coli* ST and *Pseudomonas aeruginosa* exotoxin (rEPA), or P is a polyamino acid such as poly(lysine:glutamic acid) or P is hepatitis B virus core protein or SPR96-2021, or *N. meningitidis* serogroup B antigen fHbp-231 (i.e. the fusion protein of variant2, variant3, and variantl of factor H binding protein (fHbp) as defined in WO 2015/128480, which is hereby incorporated by reference).

In one embodiment, P is TT, DT or $CRM_{197}$.

In a particular embodiment, P is $CRM_{197}$.

As defined above, according to Formula (IIa) or (IIb), Z is a linker or a bond. When Z is a linker, it can be derived from any suitable linker known in the art which is suitable for conjugation of an oligosaccharide to a protein.

In other words, Z in its unreacted form, i.e. when not linked to the oligomer and protein may have functional groups enabling it to act as a linker between the oligomers of the invention and the protein, such that Z is a functional linker (as defined according to Formula (Ia) and Formula (Ib)). Preferably, Z is derived from a compound comprising an amine, carboxylate, or hydroxyl group for coupling to a complementary group on a protein carrier, but other groups known in the art to provide a way to conjugate an oligosaccharide to a protein are also contemplated.

When oligomers of the invention are conjugated to a protein, a preferred Z moiety in Formula (IIa) or (IIb) is derived from a linker which is an amine-substituted alkoxy group, optionally in protected from. When in this form, the amine is acetylated or alkylated with a bi-functional reagent, the other end of which is similarly attached to a protein.

In one embodiment, according to Formula (IIa) or (IIb), Z is derived from a linker, either homobifunctional or heterobifunctional, able to connect an oligomer of the invention to a protein. In this respect, bifunctional linkers suitable for use in the conjugates of the invention include those known in art, such as di-carboxylic acids, preferably malonic, succinic, adipic and suberic, or activated forms thereof. Alternatively, squarate esters can be used. These types of reagents are particularly convenient for linking a compound where the spacer moiety comprises an amine to a protein. Preferably, said bifunctional linkers are derived from adipic acid N-hydroxysuccinimide diester (SIDEA), and BS(PEG)5.

In some embodiments, Z is at least two or three atoms in length. Some non-limiting examples of linkers include: $—(CH_2)_m$-A, -Ph-A, $—(CH_2)_a$-Ph-$(CH_2)_a$-A and substituted forms thereof, wherein each Ph represents an optionally substituted phenyl group, and each a and m independently represents an integer from 1-10. "A" represents a functional group or a residue thereof that is capable of or links the protein, such as $—NH_2$, —OH or —SH, an ester, an amide, or other carboxyl-containing group, a diene, or a dienophile, a maleimide, an alkyne, a cycloalkyne. Z may comprise OR', SR' or $N(R')_2$, wherein each R' is independently H or $C_1$-$C_6$-alkyl, acyl, aryl, arylalkyl, heteroacyl, heteroaryl, or heteroarylalkyl group and may further comprise A.

In one embodiment, Z in Formula (IIa) or (IIb) is a heterobifunctional linker having the following formula:

$$*—(CH_2)_p—NH(CO)—(CH_2)_p—(X—(CH_2)_p)_p—C(O)—*$$

wherein * represents the point of attachment, and wherein p is independently selected from 1 to 10; and X is selected from —O—, —S— and —NH—.

In one embodiment, Z has the formula $*—(CH_2)_6NHCO(CH_2)_4CO*$.

In another embodiment, Z is a linker having the following formula:

$$*—(CH_2)_m—NHC(O)—(CH_2)_m—C(O)—*$$

wherein * represents the point of attachment, and wherein m is independently selected from 1 to 10.

In an alternative embodiment, Z has the following formula:

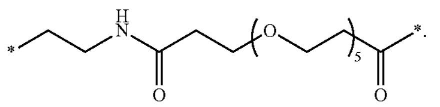

The Z linker is typically introduced into a monomer to be linked to the protein before elongating monomers are attached, and is optionally introduced in protected form, so to not impact or participate in the subsequent elongation reactions.

Therefore, in one embodiment, Z is a divalent linker having the general formula:

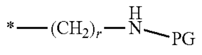

wherein r is an integer between 2 and 6, (*) represent the point of attachment to the oligomer and PG represents hydrogen or a protecting group, preferably selected from; alkoxycarbonyl, methoxycarbonyl, t-butyloxy carbonyl or benzyloxycarbonyl. The protein is attached through the amine.

When present, PG can be suitably removed to allow the reaction of the Z moiety with the protein to obtain the conjugate thereof. Alternatively, the PG can be removed and the free amino group thus obtained may be further functionalized, e.g. by introducing further spacer moieties, suitable for the connection to the protein.

In one embodiment, there is provided an oligomer conjugate according to the following formula:

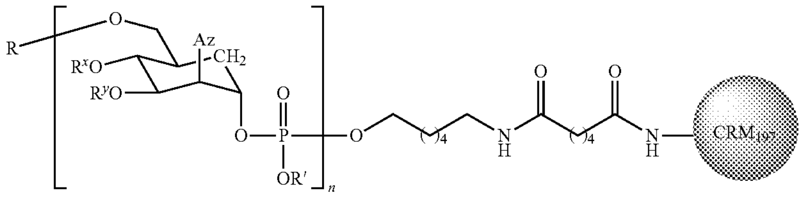

wherein n, R, R', $R^x$ and $R^y$ are as defined above.

In one embodiment of the invention, there is provided an oligomer conjugate according to the following formula, i.e. where R' is $Na^+$:

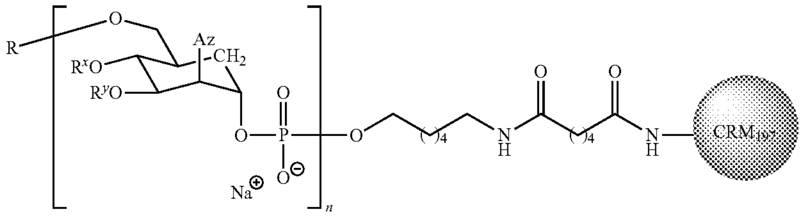

wherein n, R, $R^x$ and $R^y$ are as defined above.

When the present randomly acetylated oligomer conjugate is incorporated into a vaccine composition it shows a higher stability of the acetylation percentage than a native MenA conjugate, with less than 5% of the acetylation that may be lost when the carba analogue is formulated in the vaccine.

For the avoidance of doubt, it should be noted that the oligomers of the invention may be conjugated to a protein by any suitable method known in the art, for example, in accordance with those reported in "The design of semi-synthetic and synthetic glycoconjugate vaccines", P. Constantino et al., *Expert Opin. Drug. Discov.*

The conjugation reaction may also be carried out using conjugation methods similar to those used for the conjugation of the MenA saccharide to a carrier protein, and e.g. described in WO2004/067030. In one embodiment, the oligomers of the invention can be coupled to $CRM_{197}$ using a conjugation procedure that takes advantage of the di-N-hydroxysuccinimidyl adipate linker, as e.g. reported in Berti et al., ACS Chem. Biol., 2012, 7, 1420-1428. After treatment with the selected linker in DMSO containing trimethylamine, the obtained activated oligomers can be purified by co-precipitation with acetone and used for conjugation. Thus, the desired neo-conjugate can be obtained by overnight incubation with $CRM_{197}$ at a 100:1 oligomer/protein molar ratio. The conjugation can contemplate the activation of an oligomer of Formula (Ia)/(Ib), followed by conjugation to the protein of choice, or the activation of the concerned protein functionality and subsequent conjugation with the oligosaccharides of the invention, typically through the Z moiety. Thus, according to one embodiment, the oligomers of the invention are first activated with an appropriate activating agent, followed by coupling with the $—NH_2$ residue of the selected protein, according to methods known in the art.

In one embodiment, the Z group is activated by reaction with a first terminal portion of a linker, whereby the other end of the linker can be connected to the protein of choice. For example, and according to one embodiment, the process may comprise the activation of the oligomers of the invention with SIDEA in the presence of triethylamine, to obtain an activated ester of the starting oligomer. Such activated ester may then be reacted with $CRM_{197}$ in the presence of a phosphonate buffer to give the desired conjugate.

After conjugation, the oligomer-protein conjugate may be purified by a variety of techniques known in the art. One goal of the purification step is to remove the unbound oligomers from the oligomer-protein conjugate. Typically, conjugates of the invention can be purified from unreacted protein and oligomers by any number of standard techniques including inter alia size exclusion chromatography, density gradient centrifugation, hydrophobic interaction chromatography or ammonium sulphate fractionation, as e.g. described in Anderson, P. W., et al. J. Immunol. (1986) 137:1181-1186, and in Jennings, H. J. et al., J. Immunol. (1981) 127:1011-1018.

In an additional embodiment, Z can be a monosaccharide, preferably a mannosamine as described below. Thus, in a further embodiment, the invention also relates to oligomers having the following formula (III), wherein:

(III)

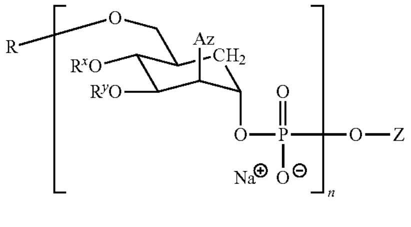

wherein R, Az and n are as defined above; and

Z is:

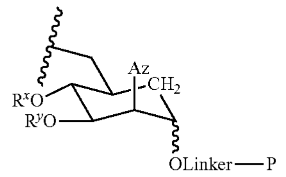

and P and the Linker are as above defined in connection with the definition of Z for Formulae (I) and (II).

For example, an example of a conjugate defined in this way is as follows:

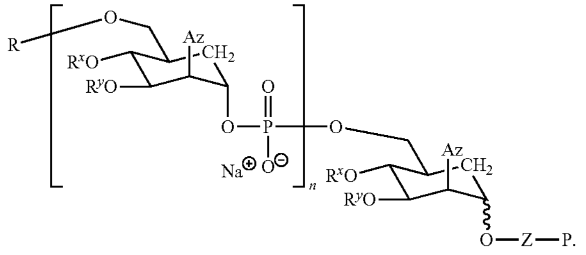

According to this embodiment, the derivatives of the invention can be linked to a selected protein directly through an —O-Linker Z moiety, thus leading to conjugate derivatives having the —OLinker-P moiety directly connected to the carbon atom of the terminal monomer. As far as the linker is concerned, this may be any suitable bivalent linker according to the above indicated linkers Z. Alternatively Z could be an amine for conjugation to a protein derivatized with linkers bearing a keto or aldehyde group.

According to a further aspect of the invention, there is provided an immunogenic composition comprising (a) a conjugate as described above; and (b) at least one pharmaceutically acceptable excipient.

Generally, the pharmaceutically acceptable excipient can be any substance that does not itself induce the production of antibodies and is not harmful to the patient receiving the composition, and which can be administered without undue toxicity. Pharmaceutically acceptable carriers and excipient are those used in the art, and can include liquids such as water, saline, glycerol and ethanol. Auxiliary substances, such as wetting or emulsifying agents, pH buffering substances, and the like, can also be present in such vehicles, according to the prior art.

The immunogenic composition may further comprise an adjuvant. The adjuvant may be an aluminium based adjuvant such as aluminium hydroxide or aluminium phosphate.

The immunogenic composition may further comprise at least one antigen derived from one of N. *Meningitidis* serogroup C, W135, Y and optionally A.

The immunogenic composition of the invention many be administered in combination with other pharmaceutically active substances or other vaccines. Compositions for administration may include other types of immunogenic compounds such as glycoconjugate, e.g. eliciting an immune response to provide protection against other *meningitidis* pathogens.

According to a further aspect of the invention, there is provided a vaccine comprising a conjugate as described above, or an immunogenic composition as previously described.

The vaccine may be formulated as a sterile substantially aqueous mixture, pyrogen-free buffered saline or phosphate-containing solution, which may include a preservative or may be preservative free. The solution may be approximately isotonic, and its isotonicity may be adjusted with agents such as sodium tartrate, sodium chloride, propylene glycol and the like. The concentration of the immunogenic oligomer conjugates of the invention in the formulations can vary widely, e.g. from less than about 0.1%, to as much as 20% to 50% or more by weight and will be selected primarily by fluid volumes, viscosities, etc., and in accordance with the particular mode of the selected administration.

The invention may also include a method for raising an immune response in a vertebrate, preferably a mammal, comprising administering an oligomer conjugate of the invention or an immunogenic composition of the invention to the mammal or other vertebrate. The immune response is preferably protective and preferably involves antibodies. The method may raise a booster response.

In one aspect, the invention relates to a method for the treatment or prevention of Meningitis A, C, W135 or Y in a subject, the method comprising administering to the subject a therapeutically or prophylactically effective amount of an oligomer conjugate according to the invention, or an immunogenic composition according to the invention, or a vaccine according to the invention. Such method may additionally comprise administration in combination with at least one serotype selected from C, W135, Y and optionally A.

As herein used, the term "derivatives of the invention" refers to both oligomers and oligomer conjugates thereof. Derivatives of the invention may also be used to immunise other mammals e.g. cattle, sheep and pigs, and other non-mammal vertebrates including fish and poultry.

In another aspect, the invention relates to a method of immunizing against Meningitis A, C, W135 or Y in a subject, the method comprising administering to the subject an immunologically effective amount of the immunogenic composition according to the invention or vaccine according to the invention.

In another aspect, the invention relates to a method of inducing an immune response to Meningitis A, C, W135 or Y in a subject, the method comprising administering to the subject an immunologically effective amount of the immunogenic composition according to the invention or vaccine according to the invention.

In one embodiment, the subject is a human.

In a further aspect, the invention relates to the use of an immunogenic composition according to the invention or vaccine according to the invention, in the manufacture of a medicament for the treatment or prevention of Meningitis A, C, W135 or Y.

In another aspect, the invention relates to an immunogenic composition according to the invention or vaccine according to the invention for use in the treatment of prevention of Meningitis A, C, W135 or Y or for use in inducing an immune response to Meningitis A, C, W135 or Y.

Immunogenic compositions of the invention will generally be administered directly to a subject. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration is preferred e.g. to the thigh or the upper arm. Injection may be via a needle (e.g. a hypodermic needle), but needle-free injection may alternatively be used.

The invention may also be used to elicit systemic and/or mucosal immunity. Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined. Infections affect various areas of the body and so the compositions of the invention may be prepared in various forms. For example, the compositions may be prepared as injectable, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. Compositions suitable for parenteral injection are most preferred. The composition is preferably sterile. It is preferably pyrogen-free. It is preferably buffered e.g. at between pH 6 and pH 8, generally around pH 7. Compositions of the invention may be isotonic with respect to humans.

Immunogenic compositions comprise an immunologically effective amount of a conjugate of the invention, as well as any other of other specified components, as needed. Dosage treatment may be a single dose schedule or a multiple dose schedule (e.g. including booster doses). The composition may be administered in conjunction with other immunoregulatory agents. Adjuvants which may be used in compositions of the invention include, but are not limited to insoluble metal salts, oil-in-water emulsions (e.g. MF59 or AS03, both containing squalene), saponins, non-toxic derivatives of LPS (such as monophosphoryl lipid A or 3-O-deacylated MPL), immunostimulatory oligonucleotides, detoxified bacterial ADP-ribosylating toxins, microparticles, liposomes, imidazoquinolones, or mixtures thereof, preferably Aluminium hydroxide, phosphate or mixture thereof. Other substances that act as immunostimulating agents are disclosed for instance in Watson, Pediatr. Infect. Dis. J. (2000) 19:331-332. These salts include oxyhydroxides and hydroxyphosphates. The salts can take any suitable form (e.g. gel, crystalline, amorphous, etc.).

NUMBERED EMBODIMENTS

Embodiment 1 An oligomer of Formula (Ia) or (Ib):

(Ia)

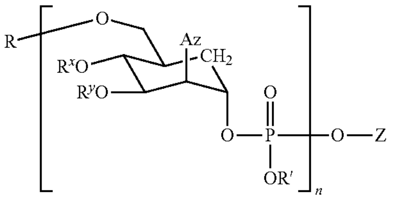

or

-continued (Ib)

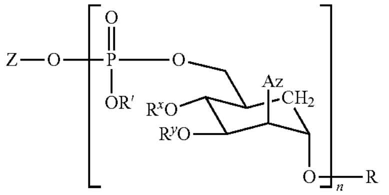

wherein n is ≥6;

R is H or —P(O)(OR")$_2$, wherein R" is H or a pharmaceutically acceptable phosphate counterion;

R' is H or a pharmaceutically acceptable phosphate counterion;

$R^x$ is H or —C(O)$CH_3$ and may be the same or different in each repeat unit;

$R^y$ is H or —C(O)$CH_3$ and may be the same or different in each repeat unit;

wherein at least one of $R^x$ or $R^y$ is —C(O)$CH_3$ in at least one repeat unit, and wherein taken together, about 50 to 90% of $R^x$ and $R^y$ in the oligomer is —C(O)$CH_3$;

Az is an aza substituent selected from the group consisting of —NH(CO)$R^1$, —N($R^1$)$_2$ and —$N_3$, wherein $R^1$ is independently selected from the group consisting of H, a linear or branched $C_1$-$C_6$-alkyl and a linear or branched $C_1$-$C_6$-haloalkyl;

Z is (i) a protecting group, (ii) a functional linker for conjugation to a protein, or (iii) a linear or branched $C_1$-$C_6$ alkyl, optionally substituted phenyl, —C(O)Y, or a linear or branched $C_1$-$C_6$-alkyl-X, wherein Y is H, a linear or branched $C_1$-$C_6$-alkyl or a protecting group, and wherein X is —$NH_2$, —$N_3$, —C≡CH, —CH═$CH_2$, —SH or —S—C≡N.

Embodiment 2 The oligomer of embodiment 1, which is defined by Formula (Ia).

Embodiment 3 The oligomer of embodiment 1 or embodiment 2, wherein n is 8 to 30.

Embodiment 4 The oligomer of embodiment 1 or embodiment 2, wherein n is 8 to 20.

Embodiment 5 The oligomer of embodiment 1 or embodiment 2, wherein n is 8 to 15.

Embodiment 6 The oligomer according to any one of the preceding embodiments, wherein Az is —NHC(O)$CH_3$.

Embodiment 7 The oligomer according to any one of the preceding embodiments, wherein n is 8.

Embodiment 8 The oligomer according to any one of embodiments 1 to 7, both of $R^x$ and $R^y$ are —C(O)$CH_3$ in at least one same repeat unit.

Embodiment 9 The oligomer according to any one of embodiments 1 to 8, wherein both of $R^x$ and $R^y$ are —C(O)$CH_3$ in 40 to 50% of the repeat units of the oligomer.

Embodiment 10 The oligomer according to embodiment 9, wherein in 10 to 20% of the remaining repeat units of the oligomer one of $R^x$ or $R^y$ is —C(O)$CH_3$, the rest of the repeat units in the oligomer having $R^x$═$R^y$═H.

Embodiment 11 An oligomer conjugate antigen of Formula (IIa) or (IIb):

(IIa)

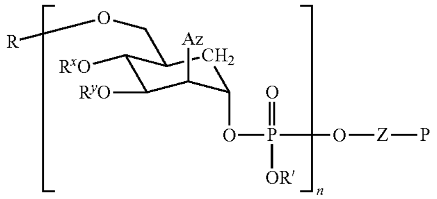

or (IIb)

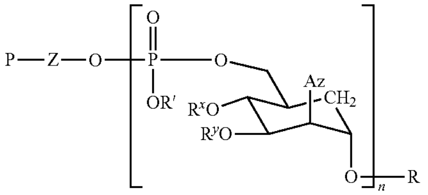

wherein n, R, R', $R^x$ and $R^y$ are as defined in any one of embodiments 1 to 10;

Z is a linker or a bond; and

P is a protein.

Embodiment 12 The conjugate of embodiment 11, which is defined by Formula (IIa).

Embodiment 13 The conjugate of embodiment 11 or 12, wherein P is an inactivated bacterial toxin selected from diphtheria toxoid (DT), tetanus toxoid (TT), $CRM_{197}$, *E. coli* ST and *Pseudomonas aeruginosa* exotoxin (rEPA), or P is a polyamino acid such as poly(lysine:glutamic acid) or P is hepatitis B virus core protein or SPR96-2021.

Embodiment 14 The conjugate of any one of embodiments 11 to 13, wherein P is $CRM_{197}$.

Embodiment 15 The conjugate of any one of embodiments 11 to 14, wherein Z is a linker having the following formula:

$$*—(CH_2)_p—NH(CO)—(CH_2)_p—(X—(CH_2)_p)_p—C(O)—*$$

wherein * represents the point of attachment, and wherein p is independently selected from 1 to 10; and X is selected from —O—, —S— and —NH—.

Embodiment 16 The conjugate of any one of embodiments 11 to 14, wherein Z is a linker having the following formula:

$$*—(CH_2)_m—NHC(O)—(CH_2)_m—C(O)—*$$

wherein m is independently selected from 1 to 10.

Embodiment 17 A conjugate according to any one of embodiments 11 to 16 having the following structure:

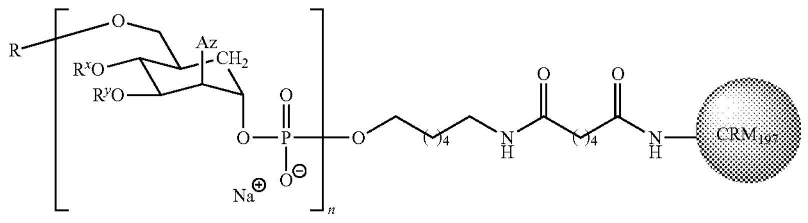

wherein n, R, $R^x$ and $R^y$ are as defined in any one of embodiments 1 to 10.

Embodiment 18 An immunogenic composition comprising (a) a conjugate according to any one of embodiments 11 to 17; and (b) at least one pharmaceutically acceptable excipient.

Embodiment 19 The immunogenic composition according to embodiment 18, further comprising an adjuvant.

Embodiment 20 The immunogenic composition according to embodiment 18 or embodiment 19, further comprising at least one antigen derived from one of *N. Meningitidis* serogroup C, W135, Y and optionally A.

Embodiment 21 A vaccine comprising a conjugate according to any one of embodiments 11 to 17, or an immunogenic composition according to any one of embodiments 17 to 18.

Embodiment 22 A method for the treatment or prevention of Meningitis A, C, W135 or Y in a subject, the method comprising administering to the subject a therapeutically or prophylactically effective amount of a conjugate according to any one of embodiments 11 to 17, or an immunogenic composition according to any one of embodiments 18 to 20, or a vaccine according to embodiment 21.

Embodiment 23 A method of immunizing against Meningitis A, C, W135 or Y in a subject, the method comprising administering to the subject an immunologically effective amount of the immunogenic composition according to any one of embodiments 18 to 20 or vaccine according to embodiment 21.

Embodiment 24 A method of inducing an immune response to Meningitis A, C, W135 or Y in a subject, the method comprising administering to the subject an immunologically effective amount of the immunogenic composition according to any one of embodiments 18 to 20 or vaccine according to embodiment 21.

Embodiment 25 The method according to any one of embodiments 22 to 24, wherein the subject is a human.

Embodiment 26 Use of the immunogenic composition according to any one of embodiments 18 to 20, or a vaccine according to embodiment 21, in the manufacture of a medicament for the treatment or prevention of Meningitis A, C, W135 or Y.

Embodiment 27 An immunogenic composition according to any one of embodiments 18 to 20, or a vaccine according to embodiment 21, for use in the treatment or prevention of Meningitis A, C, W135 or Y.

Embodiment 28 An immunogenic composition according to any one of embodiments 18 to 20, or a vaccine according to embodiment 21, for use in inducing an immune response to Meningitis A, C, W135 or Y.

The invention will be now described in more details in the below experimental part, which is intended to better illustrate the invention without posing any limitation to its scope.

Experimental Section

General Procedures and Materials.

All chemicals (Acros, Biosolve, Sigma-Aldrich and TCI) were used as received and all reactions were effectuated under an argon atmosphere, at ambient temperature (22° C.), unless stated otherwise.

For the TLC analysis were used aluminium sheets (Merck, TLC silica gel 60 F254), sprayed with a solution of $H_2SO_4$ (20%) in EtOH or with a solution of $(NH_4)_6Mo_7O_{24}\cdot 4H_2O$ (25 g/L) and $(NH_4)_4Ce(SO_4)_4\cdot 2H_2O$ (10 g/L) in 10% aqueous $H_2SO_4$ or with a solution of $KMnO_4$ (2%) and $K_2CO_3$ (1%) in $H_2O$ and then heated at ≈140° C. For the column chromatography was used 40-63 μm 60 Å silica gel (SD Screening Devices). NMR spectra ($^1H$, $^{13}C$ and $^{31}P$) were recorded with a BrukerAV-400 liq or a Bruker AV-500 or a Bruker AV-600. High resolution mass spectra were recorded by direct injection on a mass spectrometer (Thermo Finnigan LTQ Orbitrap) equipped with an electrospray ion source in positive mode (source voltage 3.5 kV, sheath gas flow 10, capillary temperature 250° C.) with resolution R=60000 at m/z 400 (mass range m/z=150-2000) and dioctylphthalate (m/z=391.28428) as a lock mass.

Abbreviations

AcOH=acetic acid
ACN=acetonitrile
DCM=dichloromethane
DMTrCl=4,4'-Dimethoxytrityl chloride
EtOAc=Ethyl acetate
THF=tetrahydrofuran
TBAF=tetrabutylammonium fluoride Example 1: Preparation of Oligomers of the Invention of Formula (Ia), According to Scheme 1

Acetamido-3,4-di-O-benzyl-2-deoxy-6-O-thexyldimethylsilyl-5a-carba-α-Dmannopyranose (13)

Silyl ether 12 may be prepared in accordance with the procedure described in Q. Gao et al. Org. Biomol. Chem., 2012, 10, 6673.

Silyl ether 12 (1.6 g, 2.7 mmol) was dissolved in dry THF (20 mL). The mixture was cooled down to 0° C. A 0.1 M solution in THF of TBAF (4.1 mL, 4.1 mmol) was slowly added. The reaction was heated up to room temperature and stirred for 3 h. To the reaction was added AcOH (0.31 mL). The solution was extracted 3 times with DCM and washed once with brine. The organic layer was dried over $Na_2SO_4$ and concentrated in vacuo. The crude was purified by flash chromatography (EtOAc/Hexane) leading to product 13 (1.1 g, 2.52 mmol) in 92% yield. The spectroscopic data were in agreement with the reported data.

2-Acetamido-3,4-di-O-benzyl-2-deoxy-5a-carba-α-D mannopyranose (14)

Alcohol 13 (1.12 g, 2.5 mmol) was dissolved in MeOH (32 mL). To the mixture was added NaOMe (0.03 g, 0.5 mmol). The reaction was stirred for 3 h at room temperature. Amberlite H+ resin was added until neutral pH was reached. The suspension was filtrated and concentrated in vacuo. $^{1}$H NMR (400 MHz, $CDCl_3$) δ=1.70-1.85 (m, 2H, H-5a), 1.90 (s, 3H, AcNH), 2.19-2.23 (m, 1H, H-5), 3.60-3.79 (m, 3H, H-6, H-1), 3.83-3.90 (m, 1H, H-2), 3.91-3.99 (m, 1H, H-4), 4.14-4.23 (m, 1H, H-3), 4.33-4.41 (m, 1H, CHH Bn), 4.54-4.72 (m, 3H, CH2 Bn, CHH Bn), 5.79 (m, 1H, NHAc), 7.22-7.42 (m, 10H, Harom). $^{13}$C NMR (100 MHz, $CDCl_3$) δ=23.5 (CH3 AcNH), 30.6 (CH2 C-5a), 39.5 (CH C-5), 53.5 (CH C-3), 64.1 (CH2 C-6), 67.9 (CH C-4), 72.4 (CH2 Bn), 73.8 (CH2 Bn), 75.5 (CH C-1), 79.0 (CH C-4), 127.3-128.9 (CHarom), 171.8 (C═O AcNH). HRMS: [C23H29NO5+H]+ requires 400.21251, found 400.21179.

2-Acetamido-3,4-di-O-benzyl-2-deoxy-6-O-(bis(4-methoxyphenyl) (phenyl))-5-carba-α-D-mannopyranose (10)

Diol 14 (0.9 g, 2.25 mmol) was dissolved in dry DCM (30 mL). To the mixture was added $Et_3N$ (1.9 mL, 13.5 mmol). DMTrCl (1.16 g, 3.38 mmol) was added. The reaction was stirred for 2 hours. To the reaction was added $H_2O$ and was washed once with brine. The organic layer was dried over $Na_2SO_4$ and concentrated in vacuo. The crude was purified by flash chromatography (EtOAc/Hexane) leading to product 10 (1.6 g, 2.04 mmol) in 91% yield. 1H NMR (400 MHz, CD3CN) δ5=1.70-1.85 (m, 1H, 5a'—H), 1.91 (s, 3H, AcNH), 2.00-2.21 (m, 2H, 5a-H, 5-H), 3.01-3.19 (m, 1H, 6'-H), 3.27-3.37 (m, 1H, 6-H), 3.51-3.67 (m, 1H, H-4), 3.73 (s, 7H, H-3, 2×OMe), 4.06-4.20 (m, 1H, H-1), 4.22-4.32 (m, 1H, CHH Bn), 4.40-4.62 (m, 3H, CH2 Bn, H-2), 4.65-4.73 (m, 1H, CHH Bn), 6.35-6.44 (m, 1H, NHAc), 6.78-7.47 (m, 23H, Harom). 13C NMR (100 MHz, CD3CN) δ=23.2 (CH3 AcNH), 31.6 (CH2 C-5a), 38.6 (CH C-5), 53.3 (CH C-2), 55.8 (2×CH3 OMe), 64.6 (CH2 C-6), 67.6 (CH C-1), 72.1 (CH2 Bn), 73.8 (CH2 Bn), 77.2 (CH C-4), 79.8 (CH C-3), 86.5 (Cq DMTr), 113.9 (CHarom), 127.3-130.7 (CHarom), 137.2-159.4 (5×Cq DMTr), 171.1 (C═O AcNH). HRMS: [C44H47NO7+Na]+ requires 724.32501, found 724.32483.

1-O—((N,N-Diisopropylamino)-O-2-cyanoethyl-phosphoramidite))-2-Acetamido-3,4-di-O-benzyl-2-deoxy-6-O-(bis(4-methoxyphenyl)(phenyl))-5a-carba-α-D-mannopyranose (9)

Alcohol 10 (1.5 g, 2.14 mmol) was co-evaporated 3 times with ACN, and dissolved in dry DCM (22 mL). To the mixture were added freshly activated MS3 Å and DIPEA (0.6 mL, 3.2 mmol). To the mixture was added 2-cyanoethyl N,N-diisopropyl-chlorophosphoramidite (0.6 mL, 2.6 mmol). The reaction was stirred for 2 hours. To the solution was added $H_2O$, and was washed once with a 1:1 solution of brine/$NaHCO_3$. The organic layer was dried over $Na_2SO_4$ and concentrated in vacuo. The crude was purified by flash chromatography (DCM/Acetone/$Et_3N$) leading to product 9 (1.81 g, 2.0 mmol) in 94% yield (mixture of diastereoisomers). 1H NMR (400 MHz, CD3CN) δ=1.04-1.24 (m, 12H, 4× isopropylamino), 1.70-1.85 (m, 1H, 5a'—H), 1.92 (s, 3H, AcNH), 2.00-2.21 (m, 2H, 5a-H, 5-H), 2.55-2.75 (m, 2H, CH2 cyanoethyl), 2.98-3.10 (m, 1H, 6'-H), 3.27-3.37 (m, 1H, 6-H), 3.47-3.70 (m, 3H, 2×CH isopropylamino, H-4), 3.70-3.88 (m, 9H, H-3, CH2 cyanoethyl, 2×OMe), 4.06-4.20 (m, 1H, H-1), 4.22-4.32 (m, 1H, CHH Bn), 4.40-4.62 (m, 3H, CH2 Bn, H-2), 4.65-4.73 (m, 1H, CHH Bn), 6.35-6.44 (m, 1H, NHAc), 6.78-7.47 (m, 23H, Harom). 13C NMR (100 MHz, CD3CN) δ=20.7 (CH2 cyanoethyl), 22.9 (CH3 AcNH), 24.5-24.7 (2×CH3 isopropylamino), 30.6 (CH2 C-5a), 38.5 (CH C-5), 43.7 (2×CH isopropylamino), 51.7 (CH C-2), 55.5 (2×CH3 OMe), 59.1 (CH2 cyanoethyl), 64.2 (CH2 C-6), 70.5 (CH C-1), 71.5 (CH2 Bn), 74.3 (CH2 Bn), 77.8 (CH C-4), 79.5 (CH C-3), 86.2 (Cq DMTr), 113.6 (CHarom), 127.3-130.7 (CHarom), 136.8-159.2 (5×Cq DMTr), 170 (C═O AcNH). 31P NMR (162 MHz, CD3CN) δ=146.9, 147.26.

General Procedure for Phosphoramidite Coupling, Oxidation and Detritylation on a Typical Scale (0.03-0.3 mmol)

Starting alcohol was co-evaporated 3 times with ACN, and was added freshly activated MS3A and DCI (0.25 M solution in ACN, 1.5 eq). The solution was stirred for 15 min. To the mixture was added phosphoramidite reagent (0.1-0.16 M solution in ACN, 1.3-3 eq) and stirred until the total conversion of the starting material (≈2 hours). Subsequently CSO (0.5M solution in ACN, 2 eq) was added to the reaction mixture and stirred for 15 min. The mixture was diluted with EtOAc and washed with a 1:1 solution of brine/$NaHCO_3$. The water layer was extracted 2 times with EtOAc. The organic layer was dried over $Na_2SO_4$ and concentrated in vacuo. The crude was co-evaporated 3 times with ACN and dissolved in DCM (5-10 mL). To the solution was added TCA (0.18M solution in DCM) and stirred for 1 hour. To the reaction mixture was added $H_2O$ and stirred for 15 min. The reaction was washed with a 1:1 solution of brine/$NaHCO_3$. The water layer was extracted with DCM 3 times. The organic layer was dried over $Na_2SO_4$ and concentrated in vacuo. The crude was purified by flash chromatography (DCM/Acetone) or by size exclusion chromatography (sephadex LH-20, MeOH/DCM 1:1).

1-O-((2-Acetamido-3,4-di-O-benzyl-2-deoxy-5a-carba-α-D-mannopyranosyl-1-O-phosphoryl)$_2$-cyanoethyl)-6-hexyl-benzyl-carbamate (15)

Alcohol 10 (0.21 g, 0.3 mmol), was coupled to phosphoramidite 11 (2.5 mL 0.16M in ACN, 0.45 mmol), oxidized, detritylated using the general procedure as described above. The crude was purified by flash chromatography (DCM/Acetone) leading to product 15 (0.216 g, 0.282 mmol) in 94% yield. 1H NMR (400 MHz, CD3CN) δ=1.24-1.40 (m, 4H, 2×CH2 hexylspacer), 1.40-1.51 (m, 2H, CH2 hexylspacer), 1.58-1.70 (m, 2H, CH2 hexylspacer), 1.80-1.92 (m, 4H, 5a'—H, AcNH), 1.96-2.02 (m, 2H, 5a-H, 5-H), 2.72-2.82 (m, 2H, CH2 cyanoethyl), 2.96 (bs, 1H, OH), 3.02-3.12 (m, 2H, CH2 hexylspacer), 3.56-3.74 (m, 3H, H-6, H-4), 3.76-3.84 (m, 1H, H-3), 3.95-4.07 (m, 2H, CH2 hexylspacer), 4.08-4.20 (m, 2H, CH2 cyanoethyl), 4.44-4.63 (m, 5H, H-1, H-2, CH2 Bn, CHH Bn), 4.72-4.80 (m, 1H, CHH Bn), 5.03 (s, 2H, CH2 Bn spacer), 5.70 (bs, 1H, NH), 6.49-6.60 (m, 1H, NHAc), 7.23-7.44 (m, 15H, Harom). 13C NMR (100 MHz, CD3CN) δ=19.9 (CH2 cyanoethyl), 22.8 (CH3 AcNH), 25.4 (CH2 hexylspacer), 26.4 (CH2 hexylspacer), 30.0 (CH2 C-5a), 30.4 (CH2 hexylspacer), 30.5 (CH2 hexylspacer), 40.0 (CH C-5), 41.0 (CH2 hexylspacer), 51.1 (CH C-2), 62.9 (CH2 C-6), 63.0 (CH2 cyanoethyl), 66.3 (CH2 Bn spacer), 68.8 (CH2 hexylspacer), 72.2 (CH2 Bn), 74.0 (CH2 Bn), 75.1 (CH C-1), 76.7 (CH C-4), 79.3

(CH C-3), 128.1-129.1 (CHarom), 138.9-139.7 (3×Cq Bn), 170.8 (C=O AcNH). 31P NMR (162 MHz, CD3CN) δ=−2.40, −2.36. HRMS: [C40H52N3O10P+H]+ requires 766.34707, found 766.34707.

1-O-di-((2-Acetamido-3,4-di-O-benzyl-2-deoxy-5a-carba-α-D-mannopyranosyl-1-O-phosphoryl)$_2$-cyanoethyl)-6-hexyl-benzyl-carbamate (16)

Alcohol 15 (0.186 g, 0.24 mmol), was coupled to phosphoramidite 9 (2.3 mL 0.16 M in ACN, 0.37 mmol), oxidized, detritylated using the general procedure as described above. The crude was purified by size exclusion chromatography (sephadex LH-20, DCM/MeOH 1:1) leading to product 16 (0.255 g, 0.199 mmol) in 82% yield. 1H NMR (400 MHz, CD3CN) δ=1.25-1.40 (m, 4H, 2×CH2 hexylspacer), 1.40-1.51 (m, 2H, CH2 hexylspacer), 1.58-1.71 (m, 2H, CH2 hexylspacer), 1.80-1.92 (m, 8H, 2×5a'—H, 2×AcNH), 1.96-2.02 (m, 4H, 2×5a-H, 2×5-H), 2.70-2.81 (m, 4H, 2×CH2 cyanoethyl), 2.96 (bs, 1H, OH), 3.01-3.12 (m, 2H, CH2 hexylspacer), 3.56-3.87 (m, 6H, 2×H-6, 2×H-4), 3.94-4.28 (m, 8H, 2×H-3, CH2 hexylspacer, 2×CH2 cyanoethyl), 4.29-4.85 (m, 12H, 2×H-1, 2×H-2, 4×CH2 Bn), 5.03 (s, 2H, CH2 Bn spacer), 5.75 (bs, 1H, NH), 6.52-6.62 (m, 1H, NHAc), 6.85-6.99 (m, 1H, NHAc), 7.21-7.41 (m, 25H, Harom). 13C NMR (100 MHz, CD3CN) δ=19.9-20.0 (2×CH2 cyanoethyl), 22.9-23.0 (2×CH3 AcNH), 25.5 (CH2 hexylspacer), 26.5 (CH2 hexylspacer), 29.1-29.2 (2×CH2 C-5a), 30.1 (CH2 hexylspacer), 30.5 (CH2 hexylspacer), 38.1-40.0 (2×CH C-5), 41.1 (CH2 hexylspacer), 50.9-51.4 (2×CH C-2), 62.5-62.6 (2×CH2 C-6), 63.0-63.2 (2×CH2 cyanoethyl), 66.3 (CH2 Bn spacer), 68.9 (CH2 hexylspacer), 72.1-72.3 (4×CH2 Bn), 75.0-75.4 (2×CH C-1), 75.5-76.9 (2×CH C-4), 79.2-79.5 (2×CH C-3), 128.2-129.1 (CHarom), 138.9-139.6 (5×Cq Bn), 170.8 (2×C=O AcNH). 31P NMR (162 MHz, CD3CN) δ=−2.60, −2.58, −2.34, −2.32, −2.22, −2.17. HRMS: [C66H83N5O17P2+H]+ requires 1280.53320, found 1280.53320.

1-O-tri-((2-Acetamido-3,4-di-O-benzyl-2-deoxy-5a-carba-α-D-mannopyranosyl-1-O-phosphoryl)$_2$-cyanoethyl)-6-hexyl-benzyl-carbamate (17)

Alcohol 16 (0.215 g, 0.167 mmol), was coupled to phosphoramidite 9 (1.6 mL 0.16 M in ACN, 0.25 mmol), oxidized, detritylated using the general procedure as described above. The crude was purified by size exclusion chromatography (sephadex LH-20, DCM/MeOH 1:1) leading to product 17 (0.285 g, 0.158 mmol) in 95% yield. 1H NMR (400 MHz, CD3CN) δ=1.25-1.40 (m, 4H, 2×CH2 hexylspacer), 1.40-1.51 (m, 2H, CH2 hexylspacer), 1.58-1.71 (m, 2H, CH2 hexylspacer), 1.80-1.92 (m, 12H, 3×5a'—H, 3×AcNH), 1.96-2.30 (m, 6H, 3×5a-H, 3×5-H), 2.68-2.83 (m, 6H, 3×CH2 cyanoethyl), 2.93 (bs, 1H, OH), 3.00-3.11 (m, 2H, CH2 hexylspacer), 3.59-3.89 (m, 9H, 3×H-6, 3×H-4), 3.96-4.22 (m, 11H, 3×H-3, CH2 hexylspacer, 3×CH2 cyanoethyl), 4.31-4.86 (m, 18H, 3×H-1, 3×H-2, 6×CH2 Bn), 5.03 (s, 2H, CH2 Bn spacer), 5.78 (bs, 1H, NH), 6.55-6.65 (m, 1H, NHAc), 6.9-7.15 (m, 2H, 2×NHAc), 7.19-7.40 (m, 35H, Harom). 13C NMR (100 MHz, CD3CN) δ=20.0-20.1 (3×CH2 cyanoethyl), 22.9-23.0 (3×CH3 AcNH), 25.5 (CH2 hexylspacer), 26.5 (CH2 hexylspacer), 28.9-29.2 (3×CH2 C-5a), 30.1 (CH2 hexylspacer), 30.5 (CH2 hexylspacer), 38.0-40.0 (3×CH C-5), 41.1 (CH2 hexylspacer), 50.8-51.4 (3×CH C-2), 62.5-63.0 (3×CH2 C-6), 63.0-63.3 (3×CH2 cyanoethyl), 66.3 (CH2 Bn spacer), 68.4 (CH2 hexylspacer), 72.1-74.1 (6×CH2 Bn), 75.2-75.5 (3×CH C-1), 75.5-76.1 (3×CH C-4), 79.3-79.5 (3×CH C-3), 128.2-129.1 (CHarom), 138.9-139.7 (7×Cq Bn), 170.9-171.2 (3×C=O AcNH). 31P NMR (162 MHz, CD3CN) δ=−2.82, −2.77, −2.62, −2.58, −2.36, −2.33, −2.24, −2.20, −2.16. HRMS: [C92H114N7O24P3+H]+ requires 1795.72333, found 1795.22333.

1-O-tetra-((2-Acetamido-3,4-di-O-benzyl-2-deoxy-5a-carba-α-D-mannopyranosyl-1-O-phosphoryl)$_2$-cyanoethyl)-6-hexyl-benzyl-carbamate (18)

Alcohol 17 (0.267 g, 0.148 mmol), was coupled to phosphoramidite 9 (1.4 mL 0.16 M in ACN, 0.22 mmol), oxidized, detritylated using the general procedure as described above. The crude was purified by size exclusion chromatography (sephadex LH-20, DCM/MeOH 1:1) leading to product 18 (0.299 g, 0.129 mmol) in 87% yield. 1H NMR (400 MHz, (CD3)$_2$CO) δ=1.31-1.47 (m, 4H, 2×CH2 hexylspacer), 1.47-1.57 (m, 2H, CH2 hexylspacer), 1.62-1.75 (m, 2H, CH2 hexylspacer), 1.85-2.02 (m, 16H, 4×5a'—H, 4×AcNH), 2.07-2.17 (m, 8H, 4×5a-H, 4×5-H), 2.82-3.00 (m, 8H, 4×CH2 cyanoethyl), 3.08-3.18 (m, 2H, CH2 hexylspacer), 3.66-4.01 (m, 12H, 4×H-6, 4×H-4), 4.04-4.36 (m, 14H, 4×H-3, CH2 hexylspacer, 4×CH2 cyanoethyl), 4.40-4.94 (m, 24H, 4×H-1, 4×H-2, 8×CH2 Bn), 5.05 (s, 2H, CH2 Bn spacer), 6.39 (bs, 1H, NH), 7.17-7.42 (m, 45H, Harom), 7.42-7.80 (m, 4H, NHAc). 13C NMR (100 MHz, (CD3)$_2$CO) δ=20.0-20.1 (4×CH2 cyanoethyl), 23.1-23.2 (4×CH3 AcNH), 25.8 (CH2 hexylspacer), 26.8 (CH2 hexylspacer), 29.2-29.8 (4×CH2 C-5a), 30.8 (CH2 hexylspacer), 30.8 (CH2 hexylspacer), 38.3-40.3 (4×CH C-5), 41.4 (CH2 hexylspacer), 51.2-51.5 (4×CH C-2), 62.6-63.4 (4×CH2 C-6), 63.4-63.6 (4×CH2 cyanoethyl), 66.2 (CH2 Bn spacer), 68.8 (CH2 hexylspacer), 72.0-75.0 (8×CH2 Bn), 75.6-75.8 (4×CH C-1), 76.5-77.2 (4×CH C-4), 79.7-79.8 (4×CH C-3), 128.1-129.1 (CHarom), 139.3-140.1 (9×Cq Bn), 170.7-171.2 (4×C=O AcNH). 31P NMR (162 MHz, CD3)$_2$CO) δ=−2.84, −2.77, −2.68, −2.47, −2.42, −2.37, −2.30, −1.96, −1.91, −1.89. HRMS: [C118H145N9O31P4+2H]++ requires 1155.45892, founded 1155.45892.

1-O-penta-((2-Acetamido-3,4-di-O-benzyl-2-deoxy-5a-carba-α-D-mannopyranosyl-1-O-phosphoryl)$_2$-cyanoethyl)-6-hexyl-benzyl-carbamate (19)

Alcohol 18 (0.277 g, 0.120 mmol), was coupled to phosphoramidite 9 (1.1 mL 0.16 M in ACN, 0.18 mmol), oxidized, detritylated using the general procedure as described above. The crude was purified by size exclusion chromatography (sephadex LH-20, DCM/MeOH 1:1) leading to product 19 (0.31 g, 0.110 mmol) in 92% yield. 1H NMR (400 MHz, (CD3)$_2$CO) δ=1.31-1.46 (m, 4H, 2×CH2 hexylspacer), 1.46-1.58 (m, 2H, CH2 hexylspacer), 1.62-1.75 (m, 2H, CH2 hexylspacer), 1.84-2.02 (m, 20H, 5×5a'—H, 5×AcNH), 2.07-2.19 (m, 10H, 5×5a-H, 5×5-H), 2.82-2.97 (m, 10H, 5×CH2 cyanoethyl), 3.08-3.18 (m, 2H, CH2 hexylspacer), 3.67-4.02 (m, 15H, 5×H-6, 5×H-4), 4.04-4.36 (m, 17H, 5×H-3, CH2 hexylspacer, 5×CH2 cyanoethyl), 4.38-4.95 (m, 30H, 5×H-1, 5×H-2, 10×CH2 Bn), 5.05 (s, 2H, CH2 Bn spacer), 6.43 (bs, 1H, NH), 7.16-7.41 (m, 55H, Harom), 7.42-7.86 (m, 5H, NHAc). 13C NMR (100 MHz, (CD3)$_2$CO) δ=19.8-20.0 (5×CH2 cyanoethyl), 23.0-23.1 (5×CH3 AcNH), 25.7 (CH2 hexylspacer), 26.7 (CH2 hexylspacer), 29.2-30.0 (5×CH2 C-5a), 30.7 (CH2 hexylspacer), 30.7 (CH2 hexylspacer), 38.2-40.2 (5×CH C-5), 41.2 (CH2 hexylspacer), 51.0-51.4 (5×CH C-2), 62.5-63.2 (5×CH2 C-6), 63.3-63.5 (5×CH2 cyanoethyl), 66.1 (CH2 Bn spacer), 68.7 (CH2 hexylspacer), 72.0-75.0 (10×CH2 Bn), 75.6-75.8 (5×CH C-1), 76.5-77.2 (5×CH C-4), 79.7-79.8 (5×CH C-3), 128.0-129.0 (CHarom), 139.2-140.0 (11×Cq Bn), 170.7-171.2 (5×C═O AcNH). 31P NMR (162 MHz, $CD3)_2CO$) δ=−2.84, −2.77, −2.68, −2.47, −2.42, −2.37, −2.30, −1.96, −1.88, −1.89, −1.86, −1.84, −1.79. HRMS: [C144H176N11O38P5+2H]++ requires 1412.55219, found 1412.55219.

1-O-hexa-((2-Acetamido-3,4-di-O-benzyl-2-deoxy-5a-carba-α-D-mannopyranosyl-1-O-phosphoryl)$_2$-cyanoethyl)-6-hexyl-benzyl-carbamate (20)

Alcohol 19 (0.280 g, 0.099 mmol), was coupled to phosphoramidite 9 (1.24 mL 0.16 M in ACN, 0.20 mmol), oxidized, detritylated using the general procedure as described above. The crude was purified by size exclusion chromatography (sephadex LH-20, DCM/MeOH 1:1) leading to product 20 (0.29 g, 0.087 mmol) in 88% yield. 1H NMR (500 MHz, $(CD3)_2CO$) δ=1.31-1.46 (m, 4H, 2×CH2 hexylspacer), 1.46-1.57 (m, 2H, CH2 hexylspacer), 1.63-1.74 (m, 2H, CH2 hexylspacer), 1.84-2.02 (m, 24H, 6×5a'—H, 6×AcNH), 2.07-2.30 (m, 12H, 6×5a-H, 6×5-H), 2.82-2.97 (m, 12H, 6×CH2 cyanoethyl), 3.09-3.18 (m, 2H, CH2 hexylspacer), 3.67-4.04 (m, 18H, 6×H-6, 6×H-4), 4.04-4.38 (m, 20H, 6×H-3, CH2 hexylspacer, 6×CH2 cyanoethyl), 4.38-5.00 (m, 36H, 6×H-1, 6×H-2, 12×CH2 Bn), 5.05 (s, 2H, CH2 Bn spacer), 6.42 (bs, 1H, NH), 7.16-7.41 (m, 65H, Harom), 7.42-7.89 (m, 6H, NHAc). 13C NMR (100 MHz, $(CD3)_2CO$) δ=19.9-20.0 (6×CH2 cyanoethyl), 23.0-23.1 (6×CH3 AcNH), 25.7 (CH2 hexylspacer), 26.8 (CH2 hexylspacer), 29.2-30.2 (6×CH2 C-5a), 30.4 (CH2 hexylspacer), 30.7 (CH2 hexylspacer), 38.2-40.2 (6×CH C-5), 41.3 (CH2 hexylspacer), 51.0-51.4 (6×CH C-2), 62.5-63.4 (6×CH2 C-6), 63.4-63.5 (6×CH2 cyanoethyl), 66.2 (CH2 Bn spacer), 68.7 (CH2 hexylspacer), 72.2-75.6 (12×CH2 Bn), 75.6-75.8 (6×CH C-1), 76.5-77.2 (6×CH C-4), 79.7-79.8 (6×CH C-3), 128.1-129.1 (CHarom), 139.2-140.0 (13×Cq Bn), 170.7-171.2 (6×C═O AcNH). 31P NMR (162 MHz, $CD3)_2CO$) δ=−2.84, −2.77, −2.68, −2.45, −2.42, −2.37, −2.31, −1.94, −1.81, −1.78. HRMS: [C170H207N13O45P6+NH4]+ requires 3356.312, found 3357.010.

In order to prepare the oligomer where n=6, the general deprotection procedure described below may be performed after the above step.

1-O-epta-((2-Acetamido-3,4-di-O-benzyl-2-deoxy-5a-carba-α-D-mannopyranosyl-1-O-phosphoryl)$_2$-cyanoethyl)-6-hexyl-benzyl-carbamate (21)

Alcohol 20 (0.140 g, 0.042 mmol), was coupled to phosphoramidite 9 (0.8 mL 0.1 M in ACN, 0.84 mmol), oxidized, detritylated using the general procedure as described above. The crude was purified by size exclusion chromatography (sephadex LH-20, DCM/MeOH 1:1) leading to product 21 (0.139 g, 0.036 mmol) in 86% yield. 1H NMR (500 MHz, $(CD3)_2CO$) δ=1.31-1.46 (m, 4H, 2×CH2 hexylspacer), 1.46-1.57 (m, 2H, CH2 hexylspacer), 1.63-1.74 (m, 2H, CH2 hexylspacer), 1.84-2.02 (m, 28H, 7×5a'—H, 7×AcNH), 2.07-2.30 (m, 14H, 7×5a-H, 7×5-H), 2.82-2.97 (m, 14H, 7×CH2 cyanoethyl), 3.09-3.18 (m, 2H, CH2 hexylspacer), 3.67-4.04 (m, 21H, 7×H-6, 7×H-4), 4.04-4.38 (m, 23H, 7×H-3, CH2 hexylspacer, 7×CH2 cyanoethyl), 4.38-5.00 (m, 42H, 7×H-1, 7×H-2, 14×CH2 Bn), 5.05 (s, 2H, CH2 Bn spacer), 6.42 (bs, 1H, NH), 7.16-7.41 (m, 75H, Harom), 7.42-7.89 (m, 7H, NHAc). 13C NMR (125 MHz, $(CD3)_2CO$) δ=19.9-20.0 (7×CH2 cyanoethyl), 23.0-23.1 (7×CH3 AcNH), 25.7 (CH2 hexylspacer), 26.8 (CH2 hexylspacer), 29.2-30.2 (7×CH2 C-5a), 30.4 (CH2 hexylspacer), 30.7 (CH2 hexylspacer), 38.2-40.2 (7×CH C-5), 41.3 (CH2 hexylspacer), 51.0-51.4 (7×CH C-2), 62.5-63.4 (7×CH2 C-6), 63.4-63.5 (7×CH2 cyanoethyl), 66.2 (CH2 Bn spacer), 68.7 (CH2 hexylspacer), 72.2-75.6 (14×CH2 Bn), 75.6-75.8 (7×CH C-1), 76.5-77.2 (7×CH C-4), 79.7-79.8 (7×CH C-3), 128.1-129.1 (CHarom), 139.2-140.0 (15×Cq Bn), 170.7-171.2 (7×C═O AcNH). 31P NMR (202 MHz, $CD3)_2CO$) δ=−2.84, −2.77, −2.68, −2.45, −2.42, −2.37, −2.31, −1.94, −1.81, −1.78. HRMS: [C196H238N15O52P7+2H]++ requires 1926,73908, founded 1926, 73908.

1-O-octa-((2-Acetamido-3,4-di-O-benzyl-2-deoxy-5a-carba-α-D-mannopyranosyl-1-O-phosphoryl)$_2$-cyanoethyl)-6-hexyl-benzyl-carbamate (22) n=8

Alcohol 22 (0.105 g, 0.027 mmol), was coupled to phosphoramidite 9 (0.7 mL 0.1 M in ACN, 0.68 mmol), oxidized, detritylated using the general procedure as described above. The crude was purified by size exclusion chromatography (sephadex LH-20, DCM/MeOH 1:1) leading to product 22 (0.103 g, 0.023 mmol) in 87% yield. 1H NMR (500 MHz, $(CD3)_2CO$) δ=1.31-1.46 (m, 4H, 2×CH2 hexylspacer), 1.46-1.57 (m, 2H, CH2 hexylspacer), 1.63-1.74 (m, 2H, CH2 hexylspacer), 1.84-2.02 (m, 32H, 8×5a'—H, 8×AcNH), 2.07-2.30 (m, 16H, 8×5a-H, 8×5-H), 2.82-2.97 (m, 16H, 8×CH2 cyanoethyl), 3.09-3.18 (m, 2H, CH2 hexylspacer), 3.67-4.04 (m, 24H, 8×H-6, 8×H-4), 4.04-4.38 (m, 26H, 8×H-3, CH2 hexylspacer, 8×CH2 cyanoethyl), 4.38-5.00 (m, 48H, 8×H-1, 8×H-2, 16×CH2 Bn), 5.05 (s, 2H, CH2 Bn spacer), 6.42 (bs, 1H, NH), 7.16-7.41 (m, 85H, Harom), 7.42-7.89 (m, 8H, NHAc). 13C NMR (125 MHz, $(CD3)_2CO$) δ=19.9-20.0 (8×CH2 cyanoethyl), 23.0-23.1 (8×CH3 AcNH), 25.7 (CH2 hexylspacer), 26.8 (CH2 hexylspacer), 29.2-30.2 (8×CH2 C-5a), 30.4 (CH2 hexylspacer), 30.7 (CH2 hexylspacer), 38.2-40.2 (8×CH C-5), 41.3 (CH2 hexylspacer), 51.0-51.4 (8×CH C-2), 62.5-63.4 (8×CH2 C-6), 63.4-63.5 (8×CH2 cyanoethyl), 66.2 (CH2 Bn spacer), 68.7 (CH2 hexylspacer), 72.2-75.6 (16×CH2 Bn), 75.6-75.8 (8×CH C-1), 76.5-77.2 (8×CH C-4), 79.7-79.8 (8×CH C-3), 128.1-129.1 (CHarom), 139.2-140.0 (17×Cq Bn), 170.7-171.2 (8×C═O AcNH). 31P NMR (202 MHz, $CD3)_2CO$) δ=−2.84, −2.77, −2.68, −2.45, −2.42, −2.37, −2.31, −1.94, −1.81, −1.78. HRMS: [C222H269N17059P8+2H]++ requires 2184.33410, found 2184.33410.

General Procedure for Deprotection on a Typical Scale (5-40 μmol)

Starting alcohol was dissolved in NH3 (aqueous solution 30-33%, 1 mL per 10 μmol) and dioxane (until it completely dissolved). The reaction mixture was stirred for 2 hours. The mixture was concentrated in vacuo. 1H NMR and 31P NMR analysis showed a total conversion to the semi-protected intermediate. The crude was dissolved in MilliQ H2O and eluted through a column containing Dowex Na+ cation-exchange resin (type: 50WX4-200, stored on a 0.5 M NaOH in H2O, flushed with MilliQ H2O and MeOH before use). The crude was dissolved in MilliQ H2O (2 mL per 10 μmol). To the reaction mixture was added 4-5 drops of glacial AcOH. The mixture was purged with Ar. To the solution was added a scup of Pd black. The reaction mixture was purged with H2 for a few seconds and stirred under H2 atmosphere for 3 days. To the mixture was added celite. The solution was filtrated and concentrated in vacuo. The crude was purified by size-exclusion chromatography (Toyopearl HW-40). The pure compound was dissolved in MilliQ H2O, eluted through a column containing Dowex Na+ cation-exchange resin (type: 50WX4-200, stored on a 0.5 M NaOH in H2O, flushed with MilliQ H2O and MeOH before use) and lyophilized.

1-O-octa-(2-Acetamido-2-deoxy-5a-carba-α-D-mannopyranosyl-1-O-phosphoryl)-6-hexyl-amine (8) n=8

Alcohol 22 (23.2 μmol) was deprotected using the general procedure described above. The pure oligomer 8 was obtained in 44% yield (25.9 mg, 10.2 μmol). $^1$H NMR (500 MHz, $D_2O$) δ=1.33-1.43 (m, 4H, 2×$CH_2$ hexylspacer), 1.57-1.69 (m, 4H, 2×$CH_2$ hexylspacer), 1.73-2.08 (m, 48H, 8×5a'—H, 8×5a-H, 8×5—H, 8×AcNH), 2.92-3.00 (m, 2H, $CH_2$ hexylspacer), 3.48-3.68 (m, 8H, 8×H-4), 3.68-3.76 (m, 2H, $CH_2$ hexylspacer), 3.81-4.22 (m, 24H, 8×H-3, 8×H-6), 4.25-4.36 (m, 8H, 8×H-1), 4.37-4.53 (m, 8H, 8×H-2). $^{13}$C NMR (126 MHz, $D_2O$) δ=21.9 (8×$CH_3$ AcNH), 24.4 ($CH_2$ hexylspacer), 25.1 ($CH_2$ hexylspacer), 26.6 ($CH_2$ hexylspacer), 28.0 (8×$CH_2$ C-5a), 29.5 ($CH_2$ hexylspacer), 38.6 (8×CH C-5), 39.4 ($CH_2$ hexylspacer), 53.5 (8×CH C-2), 61.9 (8×$CH_2$ C-6), 66.2 ($CH_2$ hexylspacer), 70.1 (8×CH C-1), 70.4 (8×CH C-4), 71.9 (8×CH C-3), 174.7 (8×C═O AcNH). $^{31}$P NMR (202 MHz, $D_2O$) δ=0.25, 0.37, 0.41, 0.44, 0.48. HRMS: $[C_{78}H_{145}N_9O_{57}P_8+H]^{++}$ requires 1183.83071, founded 1183.83071.

Production of Randomly Acetylated Carba Oligomers According to the Invention

1. Amine Protection as Boc Derivative

The dried carba-analogues DP6 (n=6), DP7 (n=7) and DP8 (n=8) were solubilized in $H_2O$:dioxane 1:1 v/v, then $NaHCO_3$ (2.95 eq) and $(Boc)_2O$ (1.13 eq) were added at 4° C. The reactions were then kept under magnetic stirring at room temperature overnight, then the products were purified by Sephadex G10 column (Eluent: $H_2O$) and fractions containing the compounds were dried.

2. Random O-acetylation

The dried Boc protected carba-analogues from step 1 were resuspended in acetonitrile, then acetic anhydride (3.6 eq for each —OH group in the molecule) and imidazole (1.8 eq) were added. The reactions were kept at 40° C. and the acetylation reaction time was extended until the target acetylation % (~75%) was reached (monitoring by $^1$H-NMR). Then the crude acetylated compounds were dried.

For the avoidance of doubt, "random O-acetylation" is intended to mean that there is no ultimate control over which and how many of $R^x$ and $R^y$ are —C(O)$CH_3$. However, using NMR techniques, it is possible to determine the total % 0-acetylation in the oligomer.

3. Boc Deprotection

The dried crude 0-acetylated carba-analogues from step 2 were solubilized in $CH_2Cl_2$:TFA 4:1 v/v and the reactions were kept under magnetic stirring at room temperature for 1 h. Then the crude reactions were dried, resolubilized in $H_2O$ and purified by Sephadex G10 column (Eluent: $H_2O$).

NMR Protocol for % Acetylation Determination

The samples were dried under vacuum, reconstituted in 0.6 mL $D_2O$ and transferred to 5 mm NMR tubes. The proton NMR spectra were collected by a standard monodimensional pulseprogram at 400 MHz and 25° C. The acquisition and processing has been conducted by TopSpin Bruker software.

The determination of % 0-acetylation in carba-analogues has been done by integrating the peaks of $H_3$+$H_4$ O—Ac (i.e.

H of acetate groups) at 5-5.4 ppm and the triplet of the $CH_2$ next to the $NH_2$ of the linker at ~3 ppm, to which is given the value 2. Looking at FIG. 1, by assuming that, if the O-Acetylation is 100%, the integration value of $H_3$+$H_4$ O—Ac must be 12 for DP6 (14 for DP7 and 16 for DP8), the following proportion can be applied:

12:100=9.04:X where X=% Acetylation

Figure 2:
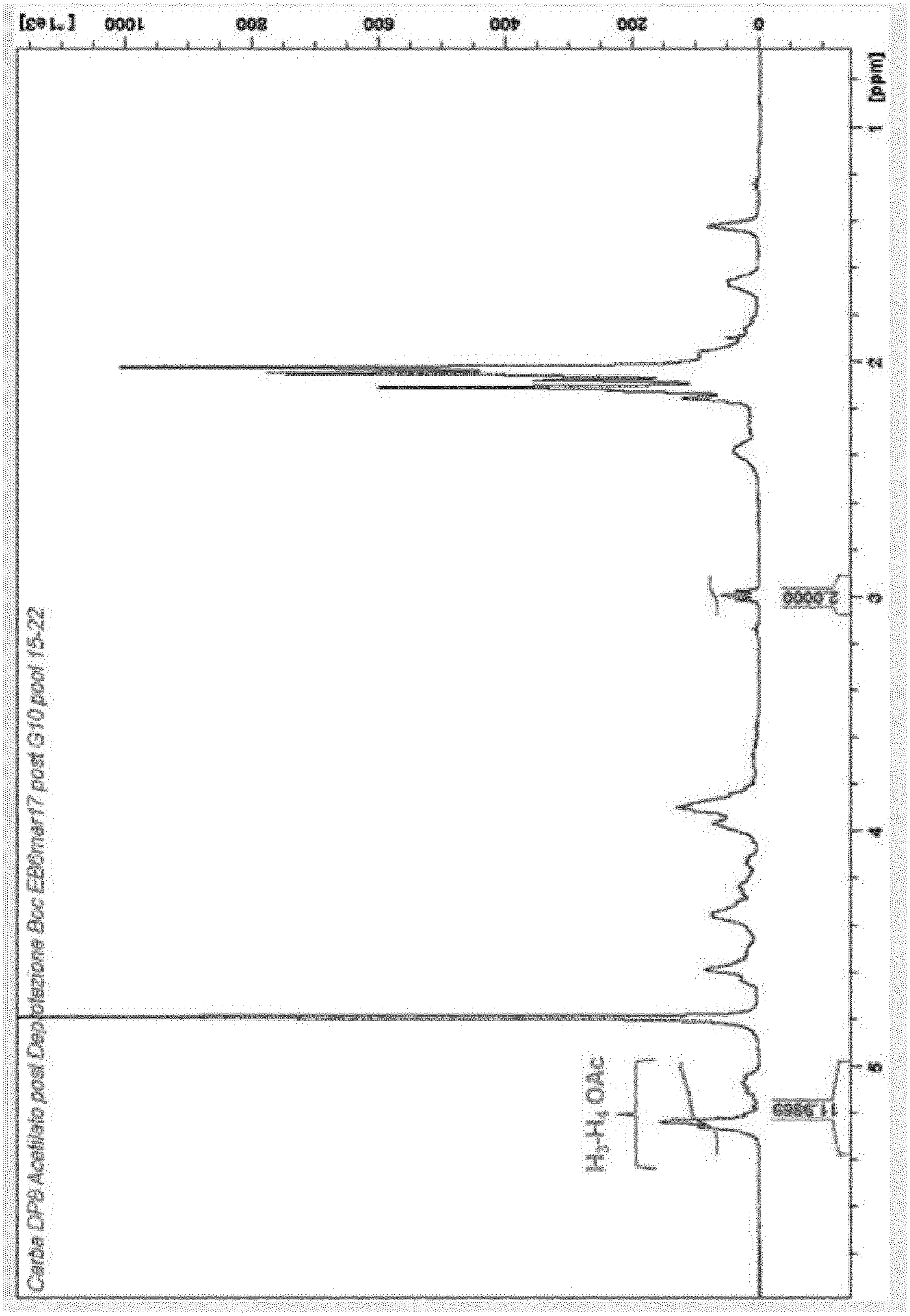
FIG. 2 is a $^{1}$H-NMR spectrum of the final randomly O-acetylated carba analogue DP8 (i.e. Formula (Ia) where n=8) with integrals for acetylation % determination.

The final products were characterized by $^1$H-NMR to confirm the identity structure and to determine the O-acetylation % of the synthetic sugars (FIG. 2 and Table 1).

FIG. 2 depicts the $^1$H NMR of the final randomly acetylated carba analogue, with integrals for % acetylation determination, where n=8.

TABLE 1

| Carba-analogue | Random O-Acetylation degree % (by $^1$H-NMR) |
|---|---|
| DP 6 | 75 |
| DP 7 | 78 |
| DP 8 | 75 |

Figure 3:
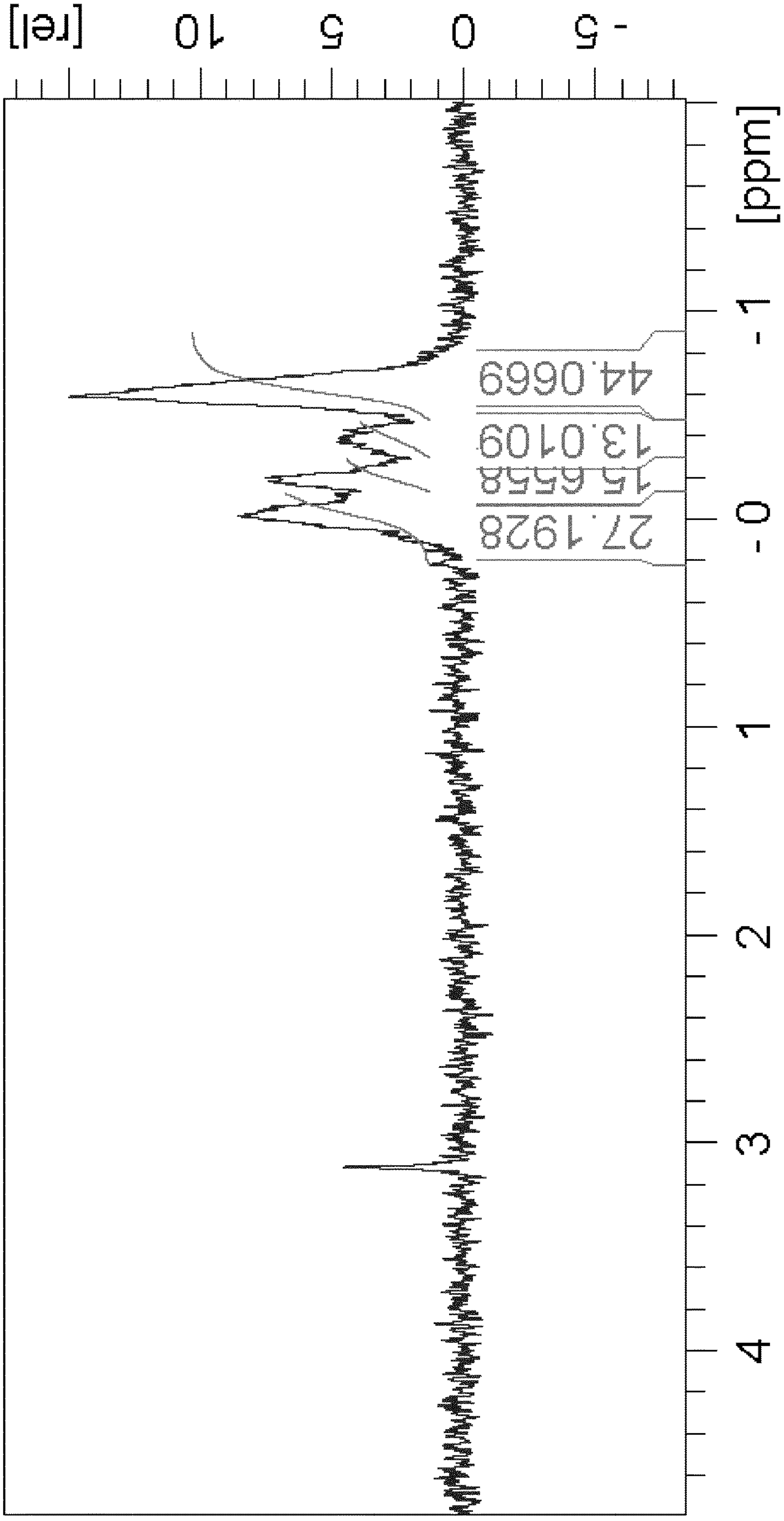
FIG. 3 is a $^{31}$P NMR spectrum of the final randomly O-acetylated carba analogue DP8 (Formula Ia). The spectrum shows concomitant acetylation occurring to an extent of 44% at position C3+C4, and acetylation at either C3 or C4 to an extent of 28%. 27% of the molecule is non acetylated.

For the same randomly acetylated carba analogue of Formula (Ia) with n=8 the distribution of the acetyl groups between 3 and 4 positions was determined by $^{31}$P NMR spectroscopy (101 MHz, $D_2O$). The spectrum recorded is depicted in FIG. 3: it shows concomitant acetylation occurring to an extent of 44% at positions C3 and C4 (i.e. $R^x$ and $R^y$ in a same repeat unit of the oligomer are both —C(O)$CH_3$), and acetylation at either C3 or C4 (i.e. $R^x$ is —C(O)$CH_3$ and $R^y$ is H or $R^x$ is H and $R^y$ is —C(O)$CH_3$ in a same repeat unit) to an extent of 28%; and 27% of the repeat units are non-acetylated.

Production of Selectively Acetylated Carba Monomer Building Block in Accordance with Scheme 2 (i.e. where $R^x$ is H and $R^y$ is —C(O)$CH_3$ D-glucal (23)

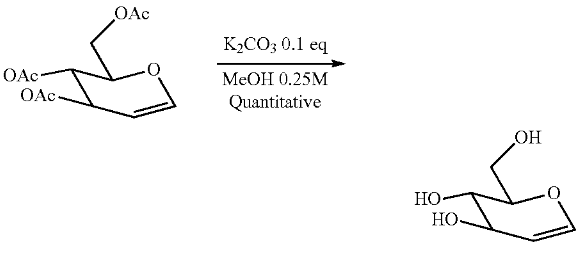

23

To a mixture of 3,4,6-tri-O-acetyl-D-glucal (10.0 g, 36.7 mmol) was added $K_2CO_3$ (508 mg, 3.67 mmol) in $MeOH_{dry}$ (150 mL) and then stirred under $N_2$ at room temperature. After 1 hour the reaction was completed and quenched with acetic acid to reach a pH of 7. The solvent was evaporated under reduce pressure and the crude product of D-glucal, a transparent oil, was directly involved in the next step.

4,6-O-(4-Methoxybenzylidene)-D-glucal (24)

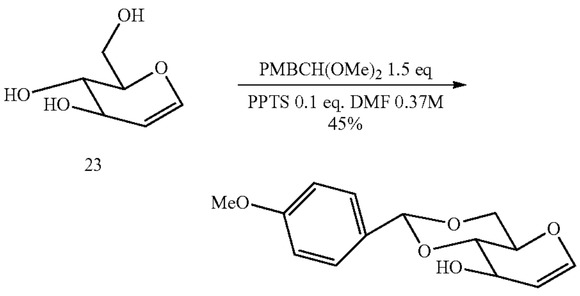

23

24

To the crude compound 23 in dry DMF (100 mL) were added anisaldehyde dimethyl acetal (9.40 mL, 55.1 mmol) and then pyridine p-toluenesulfonate (922 mg, 3.67 mmol) under $N_2$. The reaction was carried at 25-30° C. under vacuum (180 mbar) for 2.5-3 hours, on a rotavapor. The DMF was then evaporated under reduced pressure and the crude product was extracted by 100 mL of DCM. The organic layer was washed successively by 50 mL $NH_4Cl$, 50 mL of distilled water and 50 mL of a brine solution. Finally the gathered aqueous layers was extracted by 50 mL DCM. The mixture was then dried over $Na_2SO_4$ and evaporated under reduced pressure to obtain 4,6-O-(4-Methoxybenzylidene)-D-glucal as a white powder with a yield of 45%.

δ $^1H$ (400 MHz; CDCl3)

7.43 (2H, td, J 8.6, J 4.7, 8-H), 6.90 (2H, dt, J 8.8, J 4.9, 9-H), 6.33 (1H, ddd, J 6.1, J 1.6, J 0.4, 1-H), 5.55 (1H, s, 7-H), 4.76 (1H, dd, J 6.1, J 2.0, 2-H), 4.49 (1H, br d, J 7.3, 3-H), 4.35 (1H, dd, J 10.3, J 5.0, 5-H), 3.93-3.87 (1H, m, 6-H), 3.83-3.79 (1H, m, 6-H), 3.80 (3H, s, —OMe), 3.77-3.75 (1H, m, 4-H), 2.47 (1H, s, —OH).

δ $^{13}C$ (100 MHz; CDCl3)

159.4 (11-C), 143.3 (1-C), 128.6 (8-C), 126.7 (9-C), 112.8 (10-C), 102.7 (2-C), 100.9 (7-C), 79.8 (4-C), 68.9 (5-C), 67.6 (6-C), 65.7 (3-C), 54.4 (OMe).

3-O-Benzyloxy-4,6-O-(4-Methoxybenzylidene)-D-glucal (25)

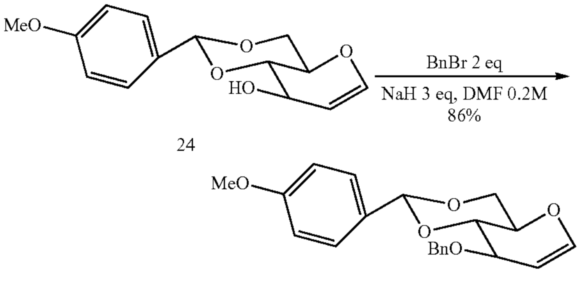

24

25

To a solution of 24 (16.05 g, 60.7 mmol) in DMF (350 mL) at 0° C. was added portionwise Sodium Hydride 60% in mineral oil (7.29 g, 182 mmol)—NaH can be previously washed off its mineral oil with n-Hexane dry 3 times. After 30 minutes stirring at the same temperature, the ice bath was removed. Benzyl Bromide was added (14.4 mL, 121 mmol) and the reaction was stirred overnight, while the temperature was warming up to room temperature. The mixture was then quenched by methanol (20 mL) and the DMF was evaporated under reduced pressure. The organic phase was extracted by 100 mL of EtOAc and then the organic layer was washed with $NH_4Cl$, $NaHCO_3$ and brine (50 mL each). The organic layer was dried over $Na_2SO_4$ and the solvent was evaporated under reduced pressure. The residue was purified by flash column chromatography on silica gel (EtOAc/Hexane=3:7) to afford 3-O-Benzyloxy-4,6-O-(4-Methoxybenzylidene)-D-glucal (18.43 g, 86%) as a white powder.

δ $^1H$ (400 MHz; CDCl3)

7.42 (2H, dt, J 8.5, J 4.6, 8-H), 7.37-7.23 (7H, m, Harom), 6.90 (2H, dt, J 8.9, J 4.9, 9-H), 6.34 (1H, dd, J 6.2, J 1.4, 1-H), 5.58 (1H, s, 7-H), 4.81 (1H, dd, J 6.17, J 2.06, 2-H), 4.79 (1H, d, J 12.1, 10-H $CH_2$ Ph), 4.70 (1H, d, J 12.1, 10-H $CH_2$ Ph), 4.36-4.32 (2H, m, 3-H, 6a-H), 4.00 (1H, dd, J 9.8, J 7.4, 6b-H), 3.88 (1H, td, J 10.1, J 4.7, 5-H), 3.81 (1H, t, J 10.1, 4-H), 3.80 (3H, s, —OMe).

δ$^{13}C$ (100 MHz; CDCl3)

160.2 (11-C), 144.5 (1-C), 138.6 (13-C), 129.9 (8-C), 129.9-127.2 ($C_{arom}$ 9, 14, 15, 16-C), 113.7 (10-C), 102.4 (2-C), 101.3 (7-C), 80.1 (5-C), 73.2 (4-C), 72.1 (6-C), 68.8 (3-C), 68.4 (12-C), 55.4 (—OMe).

3-O-Benzyloxy-4-O-(4-Methoxybenzyloxy)-D-glucal (26)

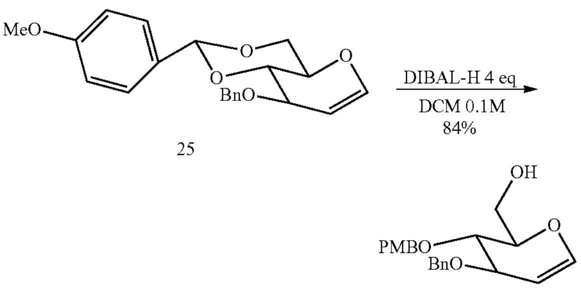

25

26

The glucal 25 (780 mg, 2.20 mmol) was dissolved in DCM (20 mL), cooled at 0° C. and stirred for 20 minutes at RT. DIBAL-H 1M in hexane (11.0 mL, 11.0 mmol) was then added dropwise at 0° C. The mixture was stirred for 2 h at 0° C. The reaction was quenched by a solution of potassium sodium tartrate tetrahydrate commonly named Rochelle salt in distilled water (1.5 g tartrate in 7.5 mL water) for 20 minutes. The mixture was then extracted by DCM (30 mL) and the organic layer was washed by distilled water twice and brine (40 mL each). The aqueous layers were finally extracted with DCM (20 mL). The organic phases were grouped and dried on $Na_2SO_4$. The solvent was evaporated under reduced pressure. The residue was purified by flash chromatography on silica gel (EtOAc/Hexane=1:3) to afford 3-O-Benzyloxy-4-O-(4-Methoxybenzyloxy)-D-glucal as a white solid yielding 84%

δ $^1H$ (400 MHz; CDCl3)

7.34-7.20 (7H, m, $H_{arom}$), 6.83 (2H, dt, J 8.7, J 4.8, 9-H), 6.34 (1H, dd, J 6.1, J 1.2, 1-H), 4.82 (1H, dd, J 6.1, J 2.6, 2-H), 4.75 (1H, d, J 11.1, 10-H $CH_2$ Ph), 4.63 (1H, d, J 11.1, 10-H $CH_2$ Ph), 4.61 (1H, d, J 11.8, 7-H $CH_2$ Ph(4-OMe)), 4.52 (1H, d, J 11.8, 7-H $CH_2$ Ph(4-OMe)), 4.19 (1H, ddd, J 6.3, J 2.4, J 2.3, 3-H), 3.87 (1H, dt, J 8.8, J 4.2, 5-H), 3.81-3.79 (2H, m, 6-H), 3.77 (1H, dd, J 8.7, J 6.3, 4-H), 3.71 (3H, s, —OMe), 2.65 (1H, s, —OH).

δ $^{13}C$ (100 MHz; CDCl3)

159.2 (11-C), 144.4 (1-C), 138.1 (13-C), 130.1 (8-C), 129.7-127.6 ($C_{arom}$ 9, 14, 15, 16-C), 113.7 (10-C), 100.1 (2-C), 77.5 (5-C), 75.6 (3-C), 74.1 (4-C), 73.3 (12-C), 70.4 (7-C), 61.4 (6-C), 55.1 (—OMe).

1,5-Anhydro-3-O-benzyloxy-4-O-(4-methoxybenzyloxy)-2,6,7-trideoxy-D-arabino-hept-1,6-dienitol (28)

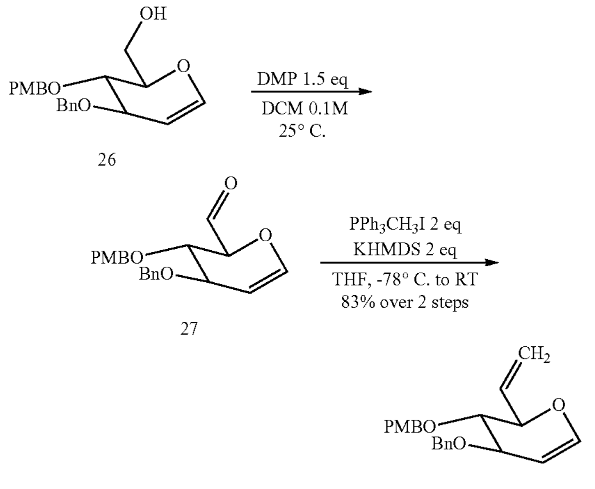

26

27

28

To a solution of the previous alcohol 26 (650 mg, 1.82 mmol) in DCM dry (6.1 mL) was added DMP (926 mg, 2.18 mmol). The mixture was then stirred at room temperature (25° C.) for 1 hour.

Meanwhile, the ylide was prepared with fresh $PPh_3CH_3I$ (1.48 g, 3.65 mmol) in THF dry (12.0 mL) at −78° C. and stirred for 25 minutes. KHMDS (7.3 mL, 3.65 mmol, 0.5M in Toluene) was then added dropwise at −78° C. The mixture was sequentially stirred at −78° C. for 20 min, at 0° C. for 50 min and finally at −78° C. for 30 min to form the ylide.

Besides the oxidation reaction was quenched by a solution of $Na_2S_2O_3$ (30 mL) and $NaHCO_3$ (30 mL) for 10 min. Then the aldehyde was worked up with DCM (3*40 mL), dried over $Na_2SO_4$ and the DCM was evaporated under reduced pressure.

The aldehyde in THF dry (11.0 mL) was then added dropwise to the ylide at −78° C. The reaction was stirred overnight. The mixture was worked up with $NH_4Cl$ (20 mL) and DCM (50 mL). Then the organic layer was again extracted with DCM (2*30 mL), washed by NaCl (80 mL) and dried over $Na_2SO_4$. The residue was purified by flash chromatography (nHexane/EtOAc=7:3) to afford the alkene as a yellow oil with a yield of 83% over 2 steps.

δ $^1H$ (400 MHz; CDCl3)

7.37-7.27 (4H, m, $H_{arom}$), 7.24 (2H, dt, J 8.6, J 5.5, 9-H), 6.86 (2H, td, J 8.7, J 5.5, 10-H), 6.41 (1H, dd, J 6.1, J 1.3, 1-H), 6.04 (1H, ddd, J 17.2, J 10.6, J 6.6, 6-H), 5.43 (1H, dt, J 2.9, J 17.3, 7b-H), 5.31 (1H, dt, J 2.6, J 10.6, 7a-H), 4.88 (1H, dd, J 6.2, J 2.7, 2-H), 4.70 (1H, d, J 10.9, 11-H, $CH_2$ Ph), 4.64 (1H, d, J 11.7, 8-H, $CH_2$ Ph(4-OMe)), 4.62 (1H, d, J 10.9, 11-H $CH_2$ Ph), 4.58 (1H, d, J 11.7, 8-H $CH_2$ Ph(4-OMe)), 4.31 (1H, dd, J 7.1, J 8.0, 5-H), 4.19 (1H, ddd, J 6.2, J 2.5, J 1.5, 3-H), 3.79 (3H, s, —OMe), 3.59 (1H, dd, J 8.6, J 6.2, 4-H).

δ $^{13}C$ (100 MHz; CDCl3)

159.4 (12-C), 144.6 (1-C), 138.5 (14-C), 134.5 (6-C), 130.3 (9-C), 129.8-127.8 ($C_{arom}$ 10, 15, 16, 17-C), 118.4 (7-C), 113.9 (11-C), 100.5 (2-C), 78.2 (5-C), 78.0 (4-C), 75.5 (3-C), 73.6 (8-C), 70.8 (13-C), 55.4 (—OMe).

(3R,4R,5R)-4-O-Benzyloxy-3-O-(4-methoxybenzyloxy)-5-(hydroxymethyl)cyclohexene (29)

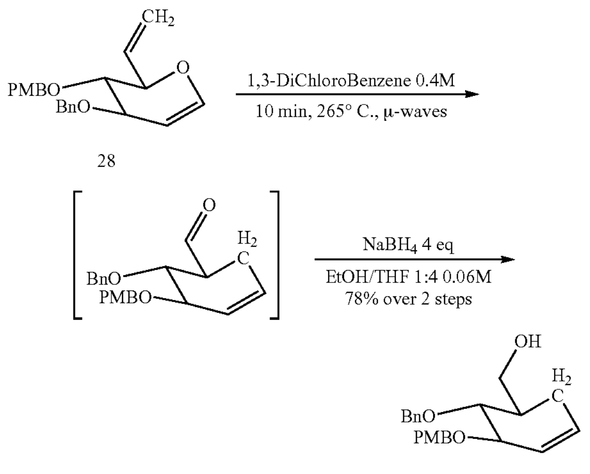

28

29

The alkene 28 (200 mg, 0.57 mmol) was dissolved in m-DCB (1.43 mL, 0.4M) at RT. The Claisen rearrangement was then carried out under micro-waves at 265° C. for 10 min. After consumption ofhe yellow solution of reactive aldehyde was immediately poured in a mixture of $NaBH_4$ (86 mg, 2.27 mmol) in THF/EtOH (10 mL, 4:1) and stirred for 1 h at RT (monospot on the TLC, orange solution). The reaction was quenched with distilled water (10 mL). The aqueous phase was increased by 10 mL of distilled water and extracted with DCM (3*20 mL). Finally, the organic layers were dried over $Na_2SO_4$. The residue was purified by flash chromatography (nHexane/EtOAc=8:2) to afford the alcohol 7 as a colorless oil with a yield of 78% over 2 steps.

δ $^1H$ (400 MHz; CDCl3)

7.28-7.16 (7H, m, $H_{arom}$), 6.79 (2H, br d, J 8.3, 14-H), 5.67-5.64 (1H, m, 1-H), 5.64-5.59 (1H, m, 2-H), 4.88 (1H, d, J 11.3, 8-H $CH_2$ Ph), 4.64 (1H, d, J 11.3, 8-H $CH_2$ Ph), 4.56 (1H, d, J 11.2, 12-H $CH_2$ Ph(4-OMe)), 4.48 (1H, d, J 11.7, 12-H $CH_2$ Ph(4-OMe)), 4.12 (1H, br d, 4-H), 3.71 (3H, s, —OMe), 3.57-3.47 (3H, m, 3-H, 6-H), 2.35 (1H, s, —OH), 2.07-2.00 (1H, m, 7-H), 1.97-1.88 (1H, m, 5-H), 1.82-1.75 (1H, m, 7-H). δ $^{13}C$ (100 MHz; CDCl3)

δ $^{13}C$ (100 MHz; CDCl3)

159.4 (17-C), 138.5 (9-C), 132.1 (14-C), 130.5-128.0 ($C_{arom}$ 10, 11, 12, 15-C), 127.7 (1-C), 126.1 (2-C), 114.0 (16-C), 82.3 (3-C), 80.9 (4-C), 74.4 (8-C), 71.1 (13-C), 65.9 (6-C), 55.4 (—OMe), 40.7 (5-C), 28.1 (7-C).

4-O-Benzyl-3-O-(4-methoxybenzyloxy)-6-O-thexyldimethylsilyl-5-methylcyclohexene (30)

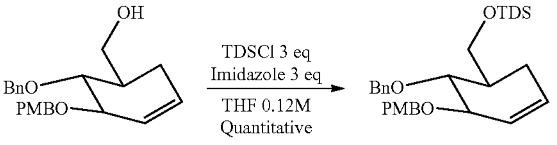

29 30

The alcohol 29 (715 mg, 2.02 mmol) was dissolved in dry THF (17 mL) at RT. Imidazole (125 mg, 1.83 mmol) was added and the mixture was stirred at RT for 5 min and then at 0° C. for 10 min. ThexylDimethylSilylChloride (1.19 mL, 6.05 mmol) was then added dropwise to pay attention to the formation of a white precipitate. Thus the ice bath was removed at the first precipitation and TDSCl remaining was added slowly to the mixture, left warming up to RT and stirring overnight. The reaction was monitored by TLC (Pent/AcOEt 3:1). The organic phase was extracted by EtOAc and then washed with distilled water (5 times). The residue was purified by flash chromatography (nHex/AcOEt 95:5) to allow the formation of compound 30 as a yellow oil with a quantitative yield.

δ $^1$H (400 MHz; CDCl3)

7.37-7.16 (7H, m, $H_{arom}$), 6.88-6.84 (2H, m, 14-H), 5.75 (1H, ddq, J 9.0, J 4.3, J 2.4, 1-H), 5.64 (1H, br d, 2-H), 4.91 (1H, d, J 11.0, 8-H $CH_2$ Ph), 4.68 (1H, d, J 11.0, 8-H $CH_2$ Ph), 4.64 (1H, d, J 11.3, 12-H $CH_2$ Ph(4-OMe)), 4.60 (1H, d, J 11.3, 12-H $CH_2$ Ph(4-OMe)), 4.16 (1H, ddq, J 7.1, J 3.6, J 1.8, 3-H), 3.86 (1H, dd, J 9.8, J 4.8, 6-H), 3.79 (3H, s, —OMe), 3.64 (1H, dd, J 10.0, J 6.6, 4-H), 3.63-3.58 (1H, m, 6-H), 2.28-2.16 (1H, m, 7-H), 2.10 (1H, dt, J 18.4, J 5.3, 7-H), 1.91 (1H, ttd, J 10.5, J 5.1, J 2.7, 5-H), 1.64 (1H, hept, J 6.9, 17-H), 0.90 (6H, d, J 6.9, 18-H), 0.87 (6H, s, 16-H), 0.13 (6H, s, 15-H).

δ $^{12}$C (100 MHz; CDCl3)

159.3 (14-C), 139.3 (9-C), 133.8 (17-C), 131.0-128.0 ($C_{arom}$ 10, 11, 12, 15-C), 127.6 (1-C), 126.3 (2-C), 113.9 (16-C), 81.5 (3-C), 79.7 (4-C), 74.7 (8-C), 71.5 (13-C), 62.6 (6-C), 55.4 (—OMe), 41.4 (5-C), 34.3 (21-C), 28.7 (7-C), 25.3 (19-C), 20.5-20.3 (20-C), 18.8-18.7 (22-C), -3.27--3.46 (18-C).

4-O-Benzyl-3-O-(4-methoxybenzyloxy)-6-O-thexyldimethylsilyl-5a-carba-α-D-glucopyranose (31)

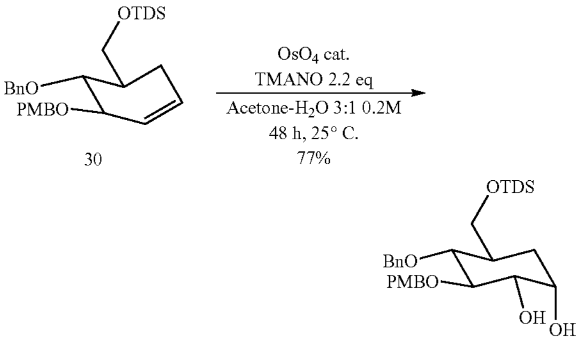

31

Compound 30 (230 mg, 0.46 mmol) was dissolved in a mixture of acetone (1.69 mL) and water (562 μL). A solution of $OsO_4$ (537 μL based on a preparation of 250 mg $OsO_4$ in 4.5 mL $H_2O$ and 18 mL acetone) and TMANO (116 mg, 1.02 mmol) were added at RT. The reaction was carried out at 25° C. for 48 h. A saturated aqueous solution of $Na_2S_2O_3$ (2 mL) was the added and the mixture was stirred at RT to reduce the $OsO_4$. The organic phase was extracted by $CHCl_3$ (15 mL), washed by brine (10 mL) and finally dried over $Na_2SO_4$. The crude product was purified by flash chromatography (nHex/AcOEt, 8.2) to afford the formation of the diol 31 as a colourless oil with a yield of 77%.

δ $^1$H (400 MHz; CDCl3)

7.37-7.15 (7H, m, $H_{arom}$), 6.87 (2H, br d, J 8.7, 14-H), 4.90 (1H, d, J 12, 8-H $CH_2$ Ph), 4.88 (1H, d, J 8, 12-H $CH_2$ Ph(4-OMe)), 4.69 (1H, d, J 10.9, 8-H $CH_2$ Ph), 4.61 (1H, d, J 11.1, 12-H $CH_2$ Ph(4-OMe)), 4.05 (1H, br d, J 2.7, 1-H), 3.96 (1H, dd, J 10.0, J 3.3, 6-H), 3.78 (3H, s, —OMe), 3.71 (1H, t, J 9.4, 3-H), 3.48 (2H, t, J 10.0, 6-H, 4-H), 3.43 (1H, dd, J 2.3, J 9.4, 2-H), 2.64 (1H, s, —OH), 2.58 (1H, s, —OH), 2.09-2.03 (1H, m, 5-H), 1.77 (1H, dt, J 14.5, J 3.6, 7-H), 1.62 (1H, hept, J 6.9, 17-H), 1.59-1.52 (1H, m, 7-H), 0.88 (6H, d, J 6.9, 18-H), 0.85 (6H, d, d 1.2, 16-H), 0.07 (6H, s, 15-H).

δ $^{13}$C (100 MHz; CDCl3)

159.5 (14-C), 138.9 (9-C), 130.9 (17-C), 129.7-127.7 ($C_{arom}$ 10, 11, 12, 15-C), 114.2 (16-C), 83.4 (3-C), 81.0 (4-C), 75.1 (13-C), 74.9 (8-C), 74.6 (2-C), 68.5 (1-C), 62.1 (6-C), 55.3 (—OMe), 38.9 (5-C), 34.3 (21-C), 30.4 (7-C), 25.2 (19-C), 20.5-20.4 (20-C), 18.8-18.7 (22-C), -3.35--3.56 (18-C).

1-O-Acetyl-4-O-benzyl-3-O-(4-methoxybenzyloxy)-6-O-thexyldimethylsilyl-5a-carba-α-D-glucopyranose (32)

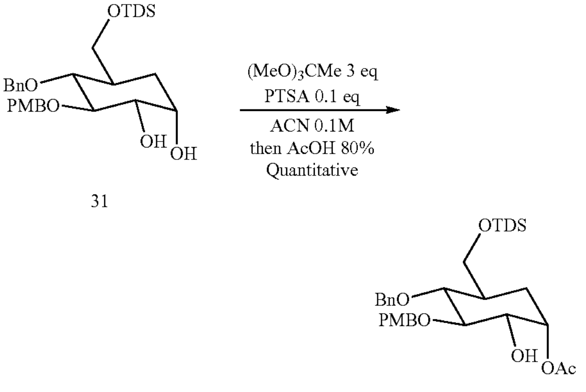

31

32

Compound 31 (155 mg, 0.29 mmol) was dissolved in acetonitrile (2.9 mL) at room temperature, under nitrogen. Trimethyl orthoacetate (115 μL, 0.88 mmol) and PTSA (5 mg, 0.03 mmol) were successively added to the mixture which was then stirred for 60 min at room temperature under nitrogen. After completion of the reaction, a solution of AcOH 80% (2.32 mL AcOH+0.58 mL $H_2O$) was added. The following reaction of acetylation was fully ended in 60 min. The organic phase was extracted with DCM (5 mL) then washed by water (5 mL) and $NaHCO_3$ (5 mL) and finally dried over $Na_2SO_4$. The residue was purified by flash chromatography (nHex/AcOEt) to afford the compound 32 selectively acetylated on the pseudo anomeric position as an uncolored oil in a quantitative yield.

δ $^{1}H$ (400 MHz; CDCl3)

7.39-7.13 (7H, m, $H_{arom}$), 6.87 (2H, dt, J 8.7, J 5.0, 14-H), 5.26 (1H, dd, J 5.7, J 3.0, 1-H), 4.91 (1H, d, J 10.6, 8-H $CH_2$ Ph), 4.90 (1H, d, J 10.9, 12-H $CH_2$ Ph(4-OMe)), 4.70 (1H, d, J 10.0, 8-H $CH_2$ Ph), 4.68 (1H, d, J 10.5, 12-H $CH_2$ Ph(4-OMe)), 3.95 (1H, dd, J 10.0, J 3.5, 6-H), 3.80 (3H, s, —OMe), 3.75 (1H, t, J 9.3, 3-H), 3.58 (1H, br d, J 9.6, 2-H), 3.53 (1H, dd, J 9.1, J 10.1, 4-H), 3.50 (1H, dd, J 9.8, J 2.4, 6-H), 2.28 (1H, s, —OH), 2.08 (3H, s, —OAc), 1.95-1.88 (1H, m, 5-H), 1.85 (1H, dt, J 14.8, J 7.6, 7-H), 1.61 (1H, dt, J 13.8, J 6.9, 7-H), 1.61 (1H, hept, J 6.9, 17-H), 0.88 (6H, d, J 6.8, 18-H), 0.84 (6H, d, J 1.7, 16-H), 0.07 (6H, d, J 4.4, 15-H).

δ $^{13}C$ (100 MHz; CDCl3)

170.9 (C(O), —OAc), 159.5 (14-C), 138.7 (9-C), 130.8 (17-C), 129.8-127.9 ($C_{arom}$ 10, 11, 12, 15-C), 114.8 (16-C), 84.0 (3-C), 80.5 (4-C), 75.4 (13-C), 75.3 (8-C), 73.4 (2-C), 71.8 (1-C), 61.8 (6-C), 55.4 (—OMe), 39.6 (5-C), 34.3 (21-C), 28.8 (7-C), 25.3 (19-C), 21.4 ($CH_3$, —OAc), 20.5-20.4 (20-C), 18.8-18.7 (22-C), −3.28--3.53 (18-C).

1-O-Acetyl-2-azido-4-O-benzyloxy-3-O-(4-methoxybenzyloxy)-6-O-thexyldimethylsilyl-5a-carba-α-D-mannopyranose

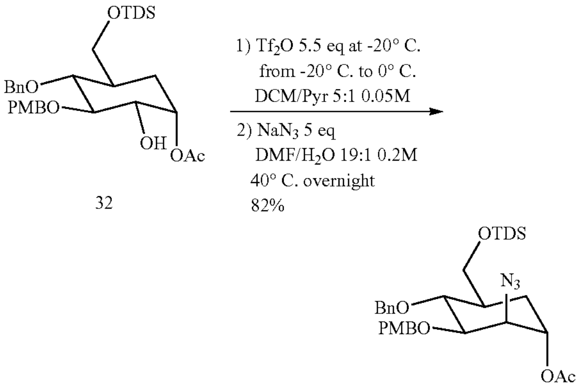

32

Compound 32 (220 mg, 0.38 mmol) was dissolved in a mixture of DCM/Pyridine (5:1, 0.05M) and stirred for 10 min at −10° C. under nitrogen. Triflate anhydride (355 μL, 2.11 mmols) was added dropwise at −10° C. The mixture was sequentially stirred for 30 min to slowly reach 0° C. and another 30 min at 0° C. After completion of the reaction, the organic phase was washed with $NaHCO_3$ and brine. The organic layer was dried over $Na_2SO_4$ and the crude afforded was directly involved in the next step after coevaporation with toluene (3 times). Next, the dry crude was dissolved in DMF/$H_2O$ (19:1, 0.2M) at 40° C. Sodium azide (125 mg, 1.92 mmols) and 15-crown-5 (15.2 μL, 0.08 mmol) were added at room temperature and the reaction was processed overnight at 40° C. After the complete disappearance of the triflate intermediate, the solvent was evaporated and the residue was finally purified by flash chromatography (nHex/EtOAc) to allow the formation of the title compound azide with a yield of 82% as an uncolored oil.

δ $^{1}H$ (400 MHz; CDCl3)

7.38-7.14 (7H, m, $H_{arom}$), 6.86 (2H, dt, J 8.6, J 4.9, 14-H), 4.98-4.94 (1H, m, 1-H), 4.88 (1H, d, J 10.7, 8-H $CH_2$ Ph), 4.66 (1H, d, J 19.1, 12-H $CH_2$ Ph(4-OMe)), 4.63 (1H, d, J 19.5, 12-H $CH_2$ Ph(4-OMe)), 4.59 (1H, d, J 10.9, 8-H $CH_2$ Ph), 3.87-3.84 (1H, m, 2-H), 3.84 (1H, dd, J 6.3, J 2.7, 6-H), 3.80 (3H, s, —OMe), 3.82-3.75 (2H, m, 4-H, 3-H), 3.52 (1H, dd, J 9.9, J 2.1, 6-H), 2.00 (3H, s, —OAc), 1.91-1.82 (2H, m, 5-H, 7-H), 1.65-1.57 (2H, m, 7-H, 17-H), 0.89 (6H, d, J 6.9, 18-H), 0.85 (6H, d, J 1.2, 16-H), 0.07 (6H, d, J 4.1, 15-H).

δ $^{13}C$ (100 MHz; CDCl3)

169.8 (C(O), —OAc), 159.6 (14-C), 138.9 (9-C), 130.2 (17-C), 129.8-127.8 ($C_{arom}$ 10, 11, 12, 15-C), 114.0 (16-C), 81.1 (4-C), 77.0 (3-C), 75.4 (8-C), 72.9 (13-C), 70.6 (1-C), 62.2 (6-C), 61.4 (2-C), 55.4 (—OMe), 39.8 (5-C), 34.4 (21-C), 27.1 (7-C), 25.3 (19-C), 21.2 ($CH_3$, —OAc), 20.6-20.5 (20-C), 18.8-18.7 (22-C), −3.35--3.52 (18-C).

1-O-Acetyl-2-acetamide-4-O-benzyloxy-3-O-(4-methoxybenzyloxy)-6-O-thexyldimethylsilyl-5a-carba-α-D-mannopyranose (33)

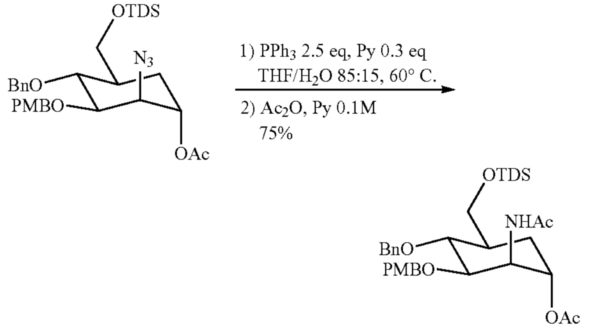

33

To a mixture of the azide as shown (334 mg, 0.56 mmol), $PPh_3$ (366 mg, 1.40 mmols) and a catalytic amount of pyridine (13.6 μL, 0.17 mmol) was added in THF/$H_2O$ (85:15, 0.14M) and stirred at 60° C. for 24 h. After disappearance of the starting material, the generated amine was dried off the solvent and then dissolved in Pyridine (5.6 mL). Acetic anhydride (1.06 mL, 11.2 mmols) was added and the solution was again stirred 24 h. The crude material was purified by flash chromatography (nHex/AcOEt), providing the acetamide 33 as a yellow oil in 75% yield.

δ $^{1}H$ (400 MHz; CDCl3)

7.39-7.28 (5H, m, $H_{arom}$), 7.19 (2H, dt, J 9.4, J 4.6, 13-H), 6.86 (2H, dt, J 9.4, J 4.8, 14-H), 5.59 (1H, d, J 8.1, NHAc), 5.12 (1H, td, J 7.2, J 3.9, 1-H), 4.71 (1H, d, J 11.3, 8-H $CH_2$ Ph), 4.56 (1H, d, J 11.3, 8-H $CH_2$ Ph), 4.50 (1H, d, J 11.2, 12-H $CH_2$ Ph(4-OMe)), 4.42 (1H, td, J 7.7, J 4.1, 2-H), 4.36 (1H, d, J 11.2, 12-H $CH_2$ Ph(4-OMe)), 3.84 (1H, dd, J 2.4, J 4.0, 3-H), 3.85-3.82 (1H, m, 6-H), 3.80 (3H, s, —OMe), 3.72 (1H, t, J 6.3, 4-H), 3.60 (1H, dd, J 9.9, J 5.5, 6-H), 2.09-2.02 (1H, m, 5-H), 2.01 (3H, s, —OAc), 1.90 (3H, s, —NHAc), 1.82 (2H, tdd, J 14.2, J 7.4, J 4.6, 7-H), 1.66-1.57 (1H, hept, J 6.9, 17-H), 0.89 (6H, d, J 6.9, 18-H), 0.84 (6H, s, 16-H), 0.08 (6H, d, J 6.2, 15-H).

δ $^{13}C$ (100 MHz; CDCl3) 170.7 (C(O), —NHAc), 170.1 (C(O), —OAc), 159.6 (14-C), 138.6 (9-C), 130.0 (15-C), 129.9 (17-C), 128.6-127.8 ($C_{arom}$ 10, 11, 12-C), 114.1 (16-C), 78.7 (3-C), 74.4 (4-C), 73.6 (8-C), 71.9 (13-C), 69.6 (1-C), 62.5 (6-C), 55.4 (—OMe), 50.6 (2-C), 39.9 (5-C), 34.4 (21-C), 27.1 (7-C), 25.2 (19-C), 23.5 (CH3, —NHAc), 21.3 (CH3, —OAc), 20.5 (20-C), 18.8 (22-C), −3.37-−3.48 (18-C).

1-O-terbutylsilyl-2-acetamide-4-O-benzyl-2-deoxy-3-O-(4-methoxybenzyloxy)-6-O-thexyldimethylsilyl-5a-carba-α-D-mannopyranose (35)

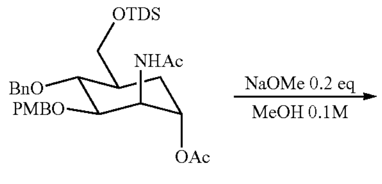

33

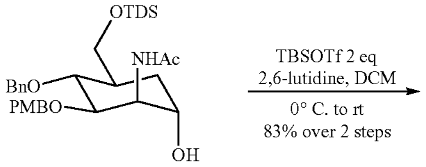

34

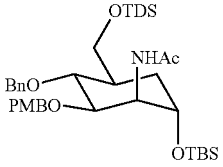

35

Compound 33 (582 mg, 0.95 mmol) was dissolved in MeOH (9.5 mL). To the mixture was added NaOMe (11 mg, 0.2 mmol). The reaction was stirred for 3 h at RT. Amberlite $H^+$ ion exchange resin was added until neutral pH was reached. The suspension was filtered and concentrated in vacuo. The crude was coevaporated 3 times with Toluene.

Under a flow of $N_2$ gas, the flask was charged with a solution of 34 (0.95 mmol) in DCM (4 mL). At 0° C., added was 2,6-lutidine (2.37 mmol) followed by TBSOTf (437 μL, 1.9 mmols) in a dropwise fashion. The mixture was stirred allowing to warm up to room temperature. After its completion, the reaction was cooled to RT, quenched with MeOH and the mixture was diluted with chloroform. The mixture was washed with 10% aq. $CuSO_4$ solution (2×), $H_2O$ and brine, dried over $Na_2SO_4$, filtered and concentrated in vacuo. Purification by column chromatography (nHex/EtOAc) furnished the title compound 35 as an orange oil in 83% yield over 2 steps.

J. D. C. Codée et al., J. Org. Chem, 2017, 82, 2, 848-868.

δ b 5 $^1$H (400 MHz; CDCl3)

7.41-7.24 (5H, m, $H_{arom}$), 7.19 (2H, dt, J 9.5, J 4.6, 13-H), 6.86 (2H, dt, J 9.4, J 4.8, 14-H), 5.57 (1H, d, J 5.7, NHAc), 4.93 (1H, d, J 10.6, 8-H $CH_2$ Ph), 4.58 (1H, d, J 10.5, 8-H $CH_2$ Ph), 4.56 (1H, d, J 11.1, 12-H $CH_2$ Ph(4-OMe)), 4.48 (1H, d, J 11.1, 12-H $CH_2$ Ph(4-OMe)), 4.27 (1H, dd, J 5.2, J 2.3, 2-H), 4.25-4.21 (1H, m, 1-H), 4.03 (1H, dd, J 9.6, J 4.5, 3-H), 3.97 (1H, dd, J 9.7, J 3.6, 6-H), 3.81 (3H, s, —OMe), 3.54 (1H, t, J 9.9, 4-H), 3.48 (1H, dd, J 9.7, J 2.2, 6-H), 2.09-2.02 (1H, m, 5-H), 2.01 (3H, s, —NHAc), 1.78-1.69 (1H, m, 7-H), 1.69-1.59 (1H, m, 17-H), 1.52-1.45 (1H, m, 7-H), 0.93 (6H, d, J 6.9, 18-H), 0.87 (6H, s, 16-H), 0.86 (6H, s, 20-H), 0.84 (6H, s, 16-H), 0.12 (6H, d, J 12.0, 19-H), 0.09 (6H, d, J 9.4, 15-H).

δ $^{13}$C (100 MHz; CDCl3)

170.7 (C(O), —NHAc), 159.5 (14-C), 139.1 (9-C), 130.2 (17-C), 130.0 (15-C), 128.6-127.7 ($C_{arom}$ 10, 11, 12-C), 114.0 (16-C), 78.5 (3-C), 77.6 (4-C), 75.5 (8-C), 71.4 (13-C), 67.7 (2-C), 62.6 (6-C), 55.4 (—OMe), 53.4 (1-C), 38.6 (5-C), 34.6 (21-C), 30.4 (7-C), 25.9 (25-C), 25.2 (19-C), 23.6 ($CH_3$—NHAc), 20.7-20.6 (20-C), 18.9-18.8 (22-C), 18.0 (24-C), −3.37-−3.58 (18-C), −4.82-−4.92 (23-C).

1-O-tertbutylsylil-2-acetamide-4-O-benzyloxy-3-O-(4-methoxybenzyloxy)-6-O-thexyldimethylsilyl-5a-carba-α-D-mannopyranose

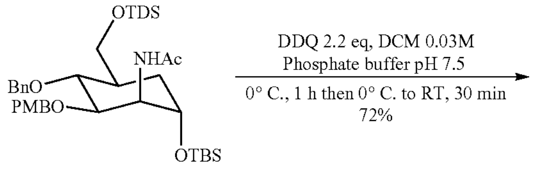

35

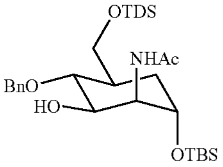

To a cooled (0° C.) solution of 14 (71 mg, 0.10 mmol) in DCM (3.4 mL) a freshly prepared phosphate buffer (362 μL, pH 7.5, 10 mM) was added. Freshly prepared DDQ (50.0 mg, 0.22 mmol) was added over 1 h in small portions, after which the mixture was allowed to warm up to RT and was stirred for 30 min. The mixture was diluted with $NaHCO_3$ and the aqueous layer was extracted with DCM twice. The combined organic layers were dried over $Na_2SO_4$ and concentrated in vacuo. Purification by column chromatography (nHex/EtOAc) afforded the compound 15 as an orange solid yielding 72%.

Dan Van Der Es, Thesis, 2016, Universiteit Leiden, pp 160.

δ 5 $^1$H (400 MHz; CDCl3)

7.41-7.27 (5H, m, $H_{arom}$), 5.52 (1H, d, J 5.4, NHAc), 4.73 (2H, s, 8-H $CH_2$ Ph), 4.26 (1H, br d, J 2.7, 1-H), 4.16 (1H, dt, J 9.0, J 3.8, 3-H), 4.06 (1H, dd, J 9.0, J 4.5, 2-H), 3.94 (1H, dd, J 9.9, J 3.7, 6-H), 3.53 (1H, dd, J 10.0, J 2.1, 6-H), 3.46 (1H, t, J 9.5, 4-H), 2.73 (1H, s, —OH), 2.10-2.03 (1H, m, 5-H), 2.00 (3H, s, —NHAc), 1.81-1.69 (1H, m, 7-H), 1.69-1.59 (1H, m, 14-H), 1.51 (1H, dt, J 13.7, J 3.2, 7-H), 0.93 (6H, d, J 6.9, 15-H), 0.88 (6H, s, 17-H), 0.87 (6H, s, 13-H), 0.14-0.04 (12H, m, 16-H, 12-H).

δ $^{13}$C (100 MHz; CDCl3)

170.1 (C(O), —NHAc), 138.8 (9-C), 128.7-127.7 ($C_{arom}$ 10, 11, 12-C), 79.6 (4-C), 74.8 (8-C), 70.7 (3-C), 67.6 (1-C), 62.9 (6-C), 56.5 (2-C), 38.5 (5-C), 34.6 (16-C), 31.2 (7-C), 25.9 (20-C), 25.3 (14-C), 23.6 (CH3, —NHAc), 20.7-20.6 (15-C), 18.9-18.8 (17-C), 18.0 (19-C), −3.37-−3.53 (13-C), −4.80-−4.90 (18-C).

1-O-tertbutylsylil-2-acetamide-4-O-benzyloxy-6-O-thexyldimethylsilyl-5a-carba-α-D-mannopyranose (36)

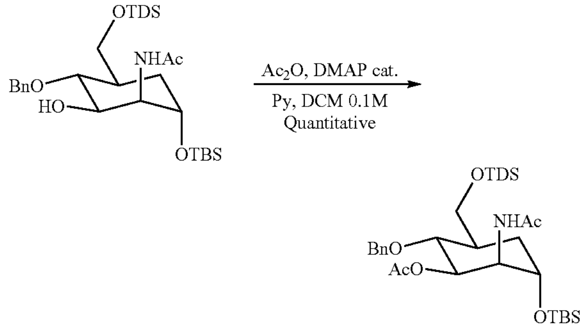

36

Alcohol as shown (180 mg, 0.32 mmol) was dissolved in dry DCM (3.2 mL) at RT under nitrogen. Pyridine (257 μL, 3.18 mmols), acetic anhydride (601 μL, 6.36 mmols) and a catalytic amount of DMAP (7.8 mg, 0.06 mmol) were successively added and the mixture was stirred until the reaction was over. The solution was quenched with MeOH and then concentrated under reduced pressure. Purification by flash chromatography (nHex/EtOAc) allowed the formation of compound 36 as a yellow oil in a quantitative yield.

δ $^{1}$H (400 MHz; CDCl3)

7.37-7.13 (5H, m, $H_{arom}$), 5.44 (1H, dd, J 10.3, J 4.5, 3-H), 5.27 (1H, d, J 7.4, NHAc), 4.70 (2H, d, J 10.9, 8-H $CH_2$ Ph), 4.61 (1H, d, J 10.9, 8-H $CH_2$ Ph), 4.31 (1H, dt, J 7.3, J 3.8, 2-H), 4.10 (1H, br d, J 2.7, 1-H), 3.97 (1H, dd, J 9.8, J 3.2, 6-H), 3.61 (1H, t, J 10.3, 4-H), 3.46 (1H, dd, J 9.8, J 2.0, 6-H), 2.18-2.11 (1H, m, 5-H), 2.00 (3H, s, —NHAc), 1.98 (3H, s, —OAc), 1.79-1.70 (1H, m, 7-H), 1.70-1.61 (1H, m, 14-H), 1.52 (1H, dt, J 14.3, J 2.8, 7-H), 0.95 (6H, d, J 6.9, 15-H), 0.90 (6H, s, 17-H), 0.88 (6H, s, 13-H), 0.13 (6H, d, J 15.1, 16-H), 0.09 (6H, d, J 14.8, 12-H).

δ $^{13}$C (100 MHz; CDCl3)

170.0 (C(O), —NHAc), 169.8 (C(O), —OAc), 138.7 (9-C), 128.6-127.6 ($C_{arom}$ 10, 11, 12-C), 76.2 (4-C), 75.1 (8-C), 73.2 (3-C), 68.1 (1-C), 62.3 (6-C), 54.0 (2-C), 38.7 (5-C), 34.6 (16-C), 30.6 (7-C), 25.8 (20-C), 25.3 (14-C), 23.6 (CH3, —NHAc), 21.2 (CH3, —OAc), 20.7-20.6 (15-C), 19.0-18.9 (17-C), 18.1 (19-C), −3.41-−3.62 (13-C), −4.90-−4.99 (18-C).

2-acetamide-4-O-benzyloxy-5a-carba-α-D-mannopyranose (37)

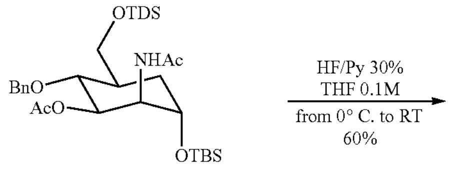

36

-continued

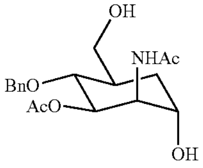

37

Compound 36 (120 mg, 0.20 mmol) was dissolved in dry THF (2.0 mL) at 0° C. A solution of HF/Py 30% (420 μL) was added dropwise and the reaction was left stirring overnight, slowly warming up from 0° C. to RT. The mixture was then quenched with $NaHCO_3$ (3 mL). The organic layer was extracted with EtOAc twice, washed with brine and dried over $Na_2SO_4$. The crude compound 37 afforded was filtrated on silica to provide a white solid in 60% yield.

δ $^{1}$H (400 MHz; $CD_3OD$)

7.37-7.26 (5H, m, $H_{arom}$), 5.33 (1H, dd, J 8.4, J 4.4, 3-H), 4.72 (2H, d, J 11.4, 8-H $CH_2$ Ph), 4.66 (1H, d, J 11.4, 8-H $CH_2$ Ph), 4.45 (1H, t, J 4.8, 2-H), 4.10 (1H, br d, J 2.7, 1-H), 3.87 (1H, q, J 4.5, 1-H), 3.78-3.73 (2H, m, 4-H, 6-H), 3.68 (1H, dd, J 10.6, J 4.2, 6-H), 2.17-2.09 (1H, m, 5-H), 2.04 (1H, s, —OH), 2.03 (1H, s —OH), 2.02 (3H, s, —NHAc), 1.98 (3H, s, —OAc), 1.83 (2H, dd, J 7.8, J 3.8, 7-H).

δ $^{13}$C (100 MHz; CDCl3)

173.6 (C(O), —NHAc), 172.0 (C(O), —OAc), 140.0 (9-C), 129.3-128.6 ($C_{arom}$ 10, 11, 12-C), 77.2 (4-C), 74.9 (8-C), 74.7 (3-C), 68.2 (1-C), 63.1 (6-C), 54.0 (2-C), 40.7 (5-C), 30.9 (7-C), 22.5 (CH3, —NHAc), 21.1 (CH3, —OAc).

2-acetamide-4-O-benzyloxy-6-O-dimethoxytrityl-5a-carba-α-D-mannopyranose (38)

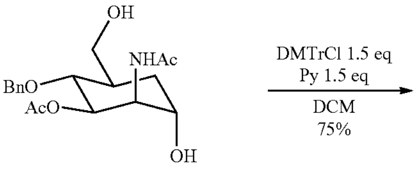

37

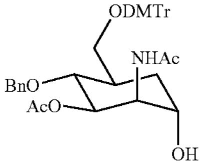

38

Compound 37 (15 mg, 42.7 μmol) was dissolved in dry DCM under nitrogen at RT. Pyridine dry (5.2 μL, 64.0 μpmol) and DMTrCl (217 mg, 64.0 μmol) were successively added and the mixture was then stirred 3 h at RT. To the reaction was then added $H_2O$. The organic layer was washed once with brine and dried over $Na_2SO_4$ and concentrated in vacuo. Purification by flash chromatography (nHex/AcOEt, 0.1% TEA) furnished compound 38 as a white solid in 74% yield.

δ $^{1}$H (400 MHz; $CD_3OD$)

7.40-7.05 (14H, m, $H_{arom}$), 6.79 (4H, dd, J 8.9, J 1.7, 13-H), 5.24 (1H, dd, J 7.9, J 4.3, 3-H), 4.53 (1H, d, J 11.3, 8-H $CH_2$ Ph), 4.38 (1H, t, J 4.8, 2-H), 4.31 (1H, d, J 11.3, 8-H $CH_2$ Ph), 3.79 (1H, q, J 5.2, 1-H), 3.72 (3H, s, —OMe), 3.72 (3H, s, —OMe), 3.61 (1H, t, J 8.1, 4-H), 3.34-3.26 (1H, m, 6-H), 3.05 (1H, t, J 8.3, 6-H), 2.34-2.24 (1H, m, 5-H), 2.08-1.98 (1H, m, 7-H), 1.95 (3H, s, —NHAc), 1.86 (3H, s, —OAc), 1.85-1.79 (1H, m, 7-H).

δ $^{13}C$ (100 MHz; $CD_3OD$)

173.6 (C(O), —NHAc), 172.0 (C(O), —OAc), 160.0 (17-C), 146.7 (9-C), 137.6 (14-C), 137.5 (14-C), 137.3 (9-C), 131.4 (18-C), 129.9-126.3 ($C_{arom}$ 10, 11, 12, 15, 19, 20, 21-C), 114.0 (16-C), 87.2 (13-C), 77.3 (4-C), 74.5 (3-C), 74.4 (8-C), 68.0 (1-C), 65.0 (6-C), 55.7 (—OMe), 54.1 (2-C), 39.2 (5-C), 31.9 (7-C), 22.5 (CH3, —NHAc), 21.1 (CH3, —OAc).

Reference Example: Preparation of Oligomer Conjugate without Acetylation—$CRM_{197}$-MenA DP6 (No OAC) and $CRM_{197}$-MenA DP8 (No OAc)

The starting oligomers (DP6 and DP8) were vacuum dried, solubilized in 1:9 $H_2O$:DMSO solution to a final amino group concentration of 40 mmol/mL, and reacted with a 12-fold molar excess of di-N-hydroxysuccinimidyl adipate linker (SIDEA), in the presence of 5-fold molar excess triethylamine as compared with amino groups. The reaction was kept under gentle stirring at room temperature for 3 h. The activated oligosaccharides were purified by precipitation with 4 volumes of ethyl acetate followed by ten washes of the pellet with 1 mL of the same solvent. Finally, the pellet was dried under vacuum, and the content of introduced N-hydroxysuccinimide ester groups was determined.

Conjugates have been prepared in 50 mM $NaH_2PO_4$ pH 7 using an active ester (AE):protein molar ratio of 40:1, carried over night at room temperature with gentle stirring. The conjugates were purified by tangential flow filtration (Vivaspin) using a cut-off of 30 kDa and using PBS pH 7.2 as buffer. Conjugates were characterized by SDS-page, by micro BCA[2] for total protein content and by MALDI analysis for total saccharide content.

Sodium Dodecyl Sulfate-Polyacrilammide gel electrophoresis (SDS-Page). SDS-Page has been performed on pre-casted 3-8% polyacrylamide gels (NuPAGE® Invitrogen). The electrophoretic runs have been performed in Tris-Acetate SDS running buffer (NuPAGE® Invitrogen) loading 5 μg of protein for each sample, using the electrophoretic chamber with a voltage of 150V for about 40 minutes. Samples were prepared by adding 3 μl of NuPAGE® LDS sample buffer. After electrophoretic running, the gel has been washed in $H_2O$ for 3 times and then dye with comassie.

Example 2: Preparation of Oligomer Conjugate of the Invention According to Formula (IIa)

The randomly O-acetylated carba-analogues prepared as described above were activated with di-N-hydroxysuccinimidyl adipate linker (SIDEA) and the % of activation obtained for the oligosaccharides was estimated to be 56% for DP6OAc, 79% for DP7OAc and 84% for DP8OAc.

Figure 4:
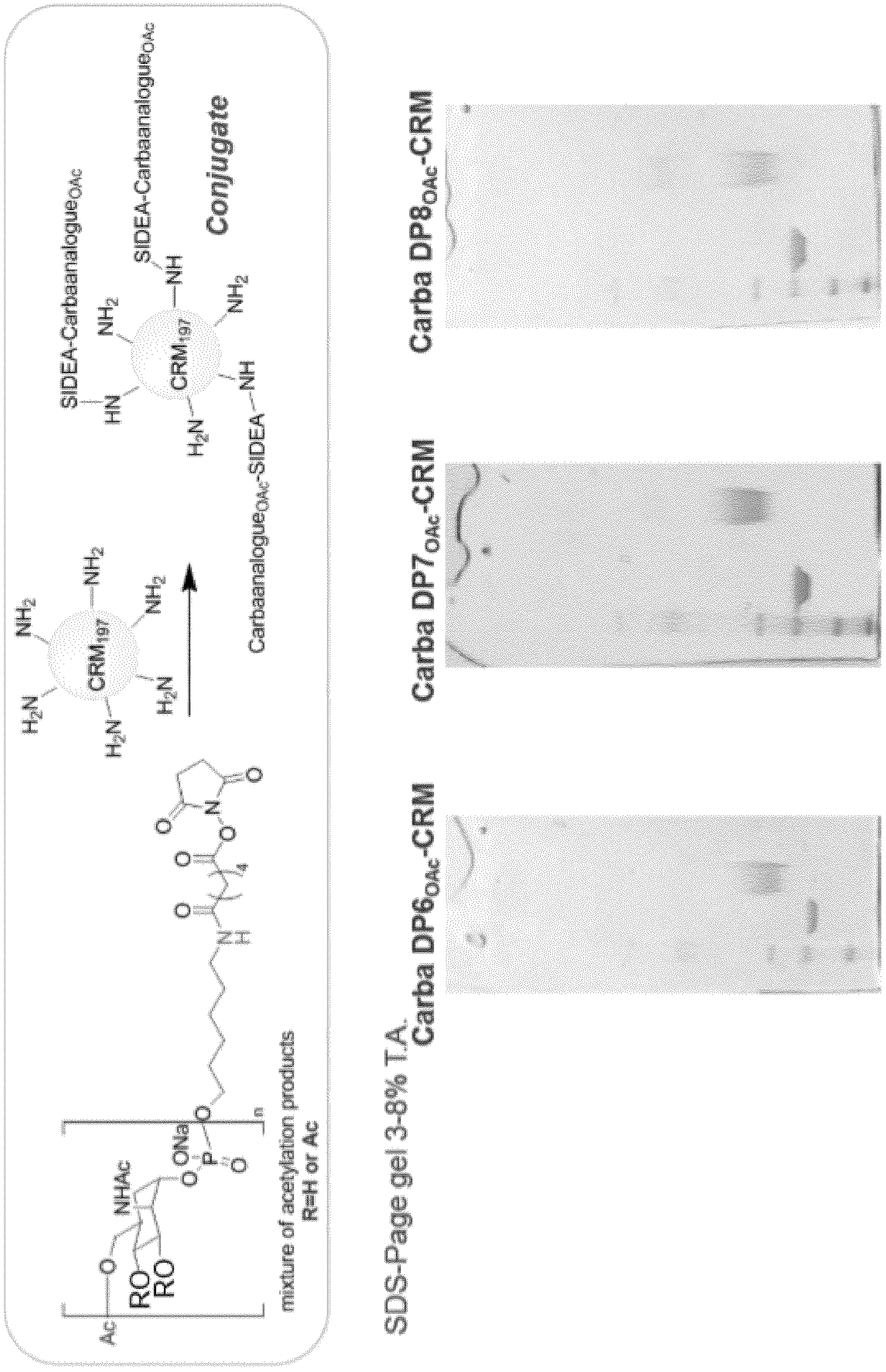
FIG. 4 depicts a conjugation scheme of an oligomer according to the invention with $CRM_{197}$ and SDS-page characterization of the crude reaction.

The activated oligosaccharides (i.e. the activated 0-acetylated carba-analogues) were lyophilized to be ready for the conjugation step. Conjugates were obtained by applying the chemistry reported in FIG. 4 and in the same figure there is shown the SDS-page characterization, where the smear of the conjugates can be observed.

Purified glycoconjugates (i.e. those including the randomly O-acetylated carba-analogues) were characterized in terms of protein content by MicroBCA and saccharide content by HPAEC-PAD, as shown in Table 2.

TABLE 2

| | Protein μg/mL | Saccharide μg/mL | sacc/prot w/w |
|---|---|---|---|
| Carba DP6 OAc-$CRM_{197}$ conj | 378.8 | 95.7 | 0.25 |
| Carba DP7 OAc-$CRM_{197}$ conj | 417.9 | 113.4 | 0.27 |
| Carba DP8 OAc-$CRM_{197}$ conj | 1388.5 | 185.3 | 0.13 |

Mice Immunization and In Vitro Analysis of Antibody Response by ELISA and Serum Bactericidal Assay (rSBA and hSBA).

Antigen formulations were prepared under sterile conditions. Groups of 10 mice (BALB/c) were immunized on days 1, 14 and 28; bleedings were performed on day 0 (pre-immune), day 27 (post 2) and day 42 (post 3). Vaccines were administered in saccharide dose and the dosage of 2 μg/mice per dose in terms of saccharide. Adjuvant $AlPO_4$ was used at the dose of 0.12 mg of $Al^{3+}$.

The vaccine formulation used for the carba MenA conjugates was as follows:

324.96 μl of AlPO4 (4.43 mg/ml containing 2 mg/ml NaCl) was added to the conjugate of interest. The volume was brought to 1.2 ml at a concentration of 1.2 mg/ml of AlPO4 by addition of PBS buffer at pH 7.2. The solution was finally diluted 1:1 v/v with PBS to a volume of 2.4 ml at a final concentration of 0.6 mg/ml of AlPO4. 200 μl/mouse of the formulation were injected. This procedure was used also for formulation of MenA-$CRM_{197}$ from a stock solution.

ELISA of sera. The antibody response induced by the glycoconjugates has been measured by ELISA. The pre-immune serum was used as negative control in this analysis. Plates have been coated with HSA-DeOAc (prepared as described in literature[21]) or MenA CPS by adding 100 μL/well of a 5 μg/mL polysaccharide solution in PBS buffer at pH 8.2 followed by incubation overnight at 4° C. HSA-DeOAc MenA CPS, $CRM_{197}$ conjugates and $CRM_{197}$ were coated at the protein concentration of 2 μg/mL in pH 7.2 PBS buffer. Coating solutions were removed from the plates by washing tree times with PBS buffer with 0.05% of Tween 20 (Sigma) (TPBS). A blocking step has been then performed by adding 100 μl/well of BSA solution at 3% in TPBS and incubating the plates 1 h at 37° C. Blocking solution has been removed from the plates by washing three times with TPBS. 200 μL/well of pre-diluted serum (1:25 for pre immune negative control, 1:200-1:500 for a reference serum and from 1:25 to 1:200 for test sera) was added in the first well of each column of the plate, while on the other wells 100 μl of TPBS has been dispensed. Eight two-fold serial dilutions along each column were then performed by transferring from well to well 100 μL of sera solutions. After primary antibody dilution, plates have been incubated for 2 h at 37° C. Three washes with TPBS, 100 μL/well TPBS solutions of secondary antibody alkaline phosphates conjugates (anti mouse IgG 1:10000, Sigma-Aldrich) were then added, and the plates incubated 1 h at 37° C. After three more washes with TPBS, 100 μL/well of a 1 mg/mL of p-NPP (Sigma) in a 0.5 M di-ethanolamine buffer pH 9.6 was added. Finally, plates were incubated for 30 min at room temperature and read at 405 nm using the plate reader Spectramax 190. Sera titers were expressed as the reciprocal of sera dilution corresponding to a cut-off OD=1.

Each immunization group has been represented as the geometrical mean (GMT) with 95% Cl of the single mouse titers. The statistical and graphical analysis has been done by GraphPad Prism 7 software.

Immunological Evaluation

To test the immunogenicity of the conjugated carba DP6 and DP8 analogues with and without random acetylation, groups of eight BALB/c female mice were immunized with the neoglycoconjugates. Conjugated sized MenA polysaccharide was used as control. Mice were immunized with three subcutaneously (s.c.) doses (2 μg on saccharide base) two weeks apart. Anti MenA CPS response was evaluated and data showed no response for the conjugates obtained with carbaMenA sugar antigen without O-Acetylation, with both the sugar chain length 6 (n=6) and 8 (n=8). Conversely, carbaMenA conjugates obtained after random O-acetylation of the oligomer induced a significantly higher response against the native MenA CPS compared with the non-acetylated vaccine (Table 3 and FIG. 5). In comparison, the response induced by the O-acetylated vaccines was lower than the benchmark MenA-$CRM_{197}$ conjugate, but only 2-fold lower for DP8 that gave the better response between those tested.

The vaccine formulation used for the carba MenA conjugates was as follows:

324.96 μl of $AIP_4$ (4.43 mg/ml containing 2 mg/ml NaC) was added to the conjugate of interest. The volume was brought to 1.2 ml at a concentration of 1.2 mg/ml of $AlPO_4$ by addition of PBS buffer at pH 7.2. The solution was finally diluted 1:1 v/v with PBS to a volume of 2.4 ml at a final concentration of 0.6 mg/ml of $AlPO_4$. 200 μl/mouse of the formulation were injected. This procedure was used also for formulation of MenA-$CRM_{197}$ from a stock solution.

The ELISA response after two and three doses is reported in Table 3. As can be seen, Groups 2 and 3 are those according to the invention. For Group 2, an oligomer conjugate having n=6 and random acetylation as described above was used. For Group 3, an oligomer conjugate having n=8 and random acetylation as described above was used. The level of acetylation of Groups 2 and 3 conjugates was around 75%.

TABLE 3

| | Group 1 MenA-$CRM_{197}$ Native Post 2/Post 3 | Group 2 carbaMenA DP6OAc-$CRM_{197}$ (random OAc) Post 2/Post 3 | Group 3 carbaMenA DP8OAc-$CRM_{197}$ (random OAc) Post 2/Post 3 | Group 4 carbaMenA DP6-$CRM_{197}$ (no OAc) Post 2/Post 3 | Group 5 carbaMenA DP8-$CRM_{197}$ (no OAc) Post 2/Post 3 |
|---|---|---|---|---|---|
| GMTs | 1670/6202 | 174/1317 | 400/5480 | 2/2 | 2/100 |
| | 272/3200 | 400/3200 | 1396/4635 | 2/2 | 2/2 |
| | 1165/5434 | 800/5266 | 381/1350 | 2/100 | 2/2 |
| | 3200/12800 | 275/1600 | 186/1063 | 2/2 | 2/2 |
| | 400/6400 | 687/800 | 800/5398 | 2/2 | 13/100 |
| | 3200/11275 | 80/1600 | 670/3200 | 2/2 | 50/100 |
| | 3200/11708 | 200/1600 | 400/1428 | 2/2 | 2/2 |
| | 2526/12232 | 742/4351 | 168/1600 | 2/2 | 2/2 |
| | 800/4472 | 270/2397 | 800/2932 | 2/2 | 2/2 |
| | 1222/192 | 274/2990 | 400/1009 | 2/2 | 2/2 |
| | 1328/5114 | 314/2165 | 463/2306 | 2/3 | 3/6 |

Figure 5A:
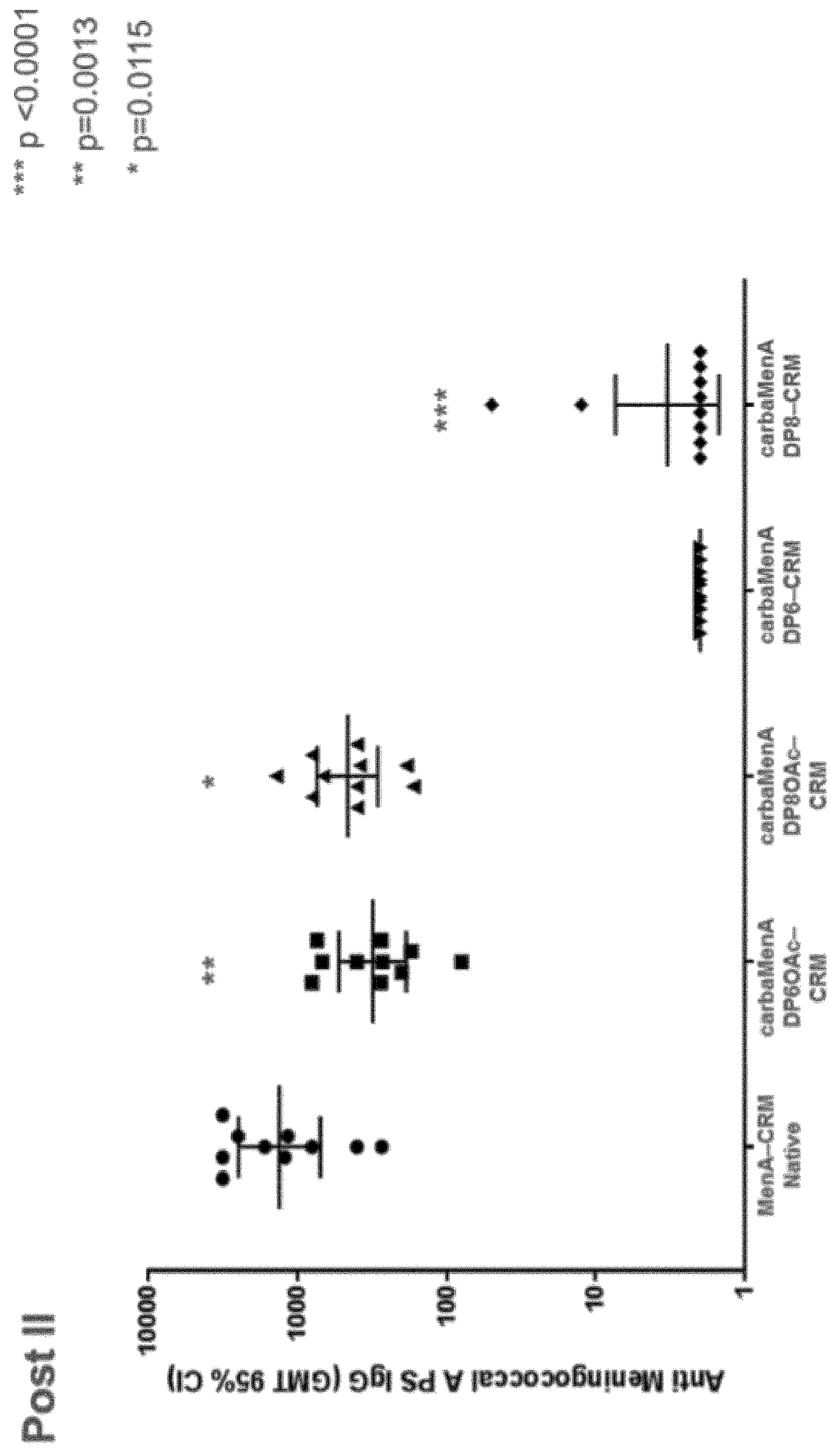
FIGS. 5*a* and 5*b* are ELISA titers post two and three doses of vaccines. The p values refer to the comparison between the benchmark MenA-$CRM_{197}$ native and the other groups of vaccination.
Figure 5B:
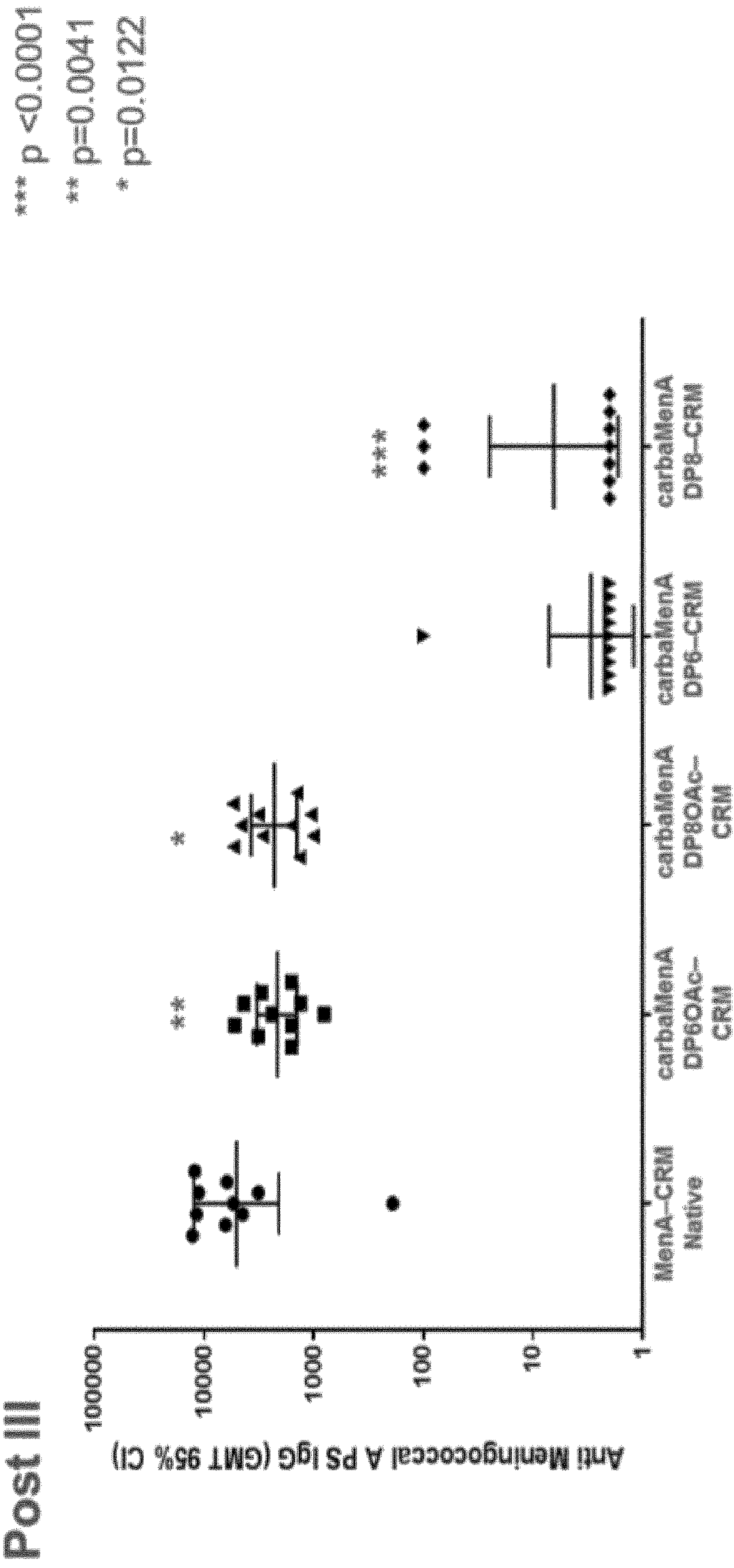

FIGS. 5*a* and 5*b* provide ELISA titers post two and three doses. The p values refer to the comparison between the benchmark native MenA-$CRM_{197}$ and the other groups.

A second immunological study was carried out as described in the following, by comparing the above said randomly O-acetylated carbaMenA DP8 analogue of this invention with a carbaMenA DP8 selectively O-acetylated only at position 3 with a percentage of O-acetylation of about 70%, and with the MenA vaccine as a positive control, all conjugated to $CRM_{197}$.

Figure 6:
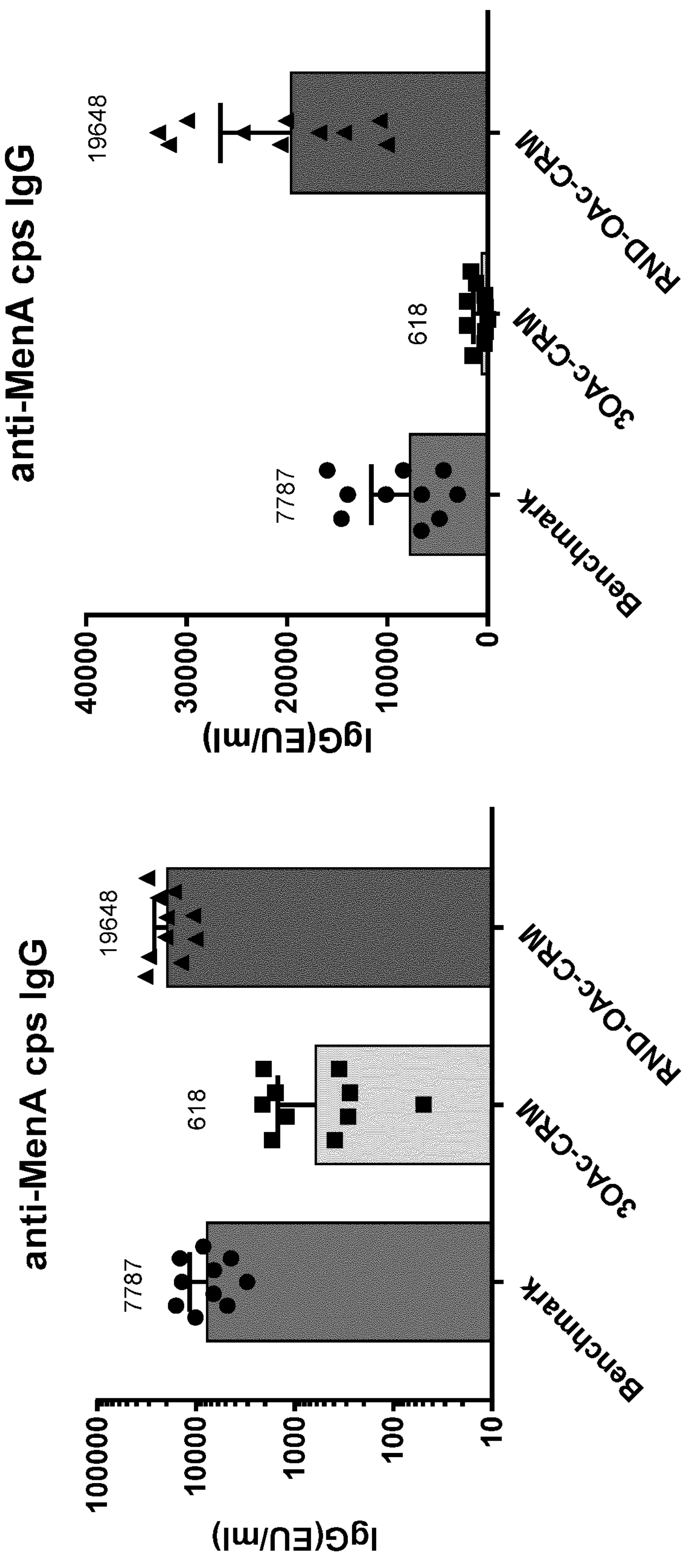
FIG. 6 shows ELISA titers measured post three doses of vaccine: anti-MenA polysaccharide IgG antibodies have been evaluated with $CRM_{197}$ conjugates of randomly O-acetylated carbaMenA analogue DP8 in comparison with $CRM_{197}$ conjugates of selectively 3-O-acetylated carbaMenA DP8 and with native MenA-$CRM_{197}$ vaccine as the benchmark (i.e. positive control).

Three groups of ten Balb/C mice were immunized with the above said conjugates. Mice were immunized with three subcutaneously (s.c.) doses (2 μg on saccharide base; 200 μl/mouse of the formulation) two weeks apart. The vaccine formulation used for the carba MenA conjugates was the same as reported above for the first immunological study. Anti MenA CPS response was evaluated, and data showed a total IgG response after the third immunization about 10 times lower for the 3 O-acetylated carbaMenA DP8 than the MenA vaccine benchmark. Conversely, the randomly O-acetylated carbaMenA DP8 conjugate of the invention induced a significantly higher response against the native MenA CPS compared with the 3 O-acetylated conjugate, and substantially equivalent to that of the MenA vaccine benchmark (FIG. 6).

| | Group 1 MenA $CRM_{197}$ native | Group 2 carbaMenA $CRM_{197}$ (3-OAc) | Group 3 carbaMenA $CRM_{197}$ (random OAc) |
|---|---|---|---|
| ELISA GMT (min; max) | 7787 (3056; 16016) | 618 (50; 2086) | 19648 (10158; 32933) |
| SBA GMT (min; max) | 4350 (1310; 9892) | 63 (8; 526) | 2644 (6788; 630) |

In Vitro Bactericidal Assay

Functional antibodies induced by vaccine immunization were analyzed by measuring the complement-mediated lysis of *N. meningitidis* with an in vitro bactericidal assay.

A commercial lot of baby rabbit complement was used as source of active complement for rSBA, while human plasma obtained from volunteer donors under informed consent was used as complement source for hSBA. Briefly, *N. meningitidis* strain was grown overnight on chocolate agar plates at 37° C. in 5% $CO_2$. Colonies were inoculated in Mueller-Hinton broth, containing 0.25% glucose to reach an OD600 of 0.05-0.08 and incubated at 37° C. with shaking. When bacterial suspensions reached OD600 of 0.25-0.27, bacteria were diluted in the assay buffer (DPBS with 1% BSA and 0.1% glucose) at the working dilution (ca. 104 CFU/mL). The total volume in each well was 50 μL with 25 μL of serial two-fold dilutions of the test serum, 12.5 μL of bacteria at the working dilution and 12.5 μL of complement source. The tested sera were pooled and heat-inactivated for 30 minutes at 56° C. Negative controls included bacteria incubated, separately, with the complement serum without the test serum and with test sera and the heat-inactivated complement. Immediately after the addition of the baby rabbit complement, negative controls were plated on Mueller-Hinton agar plates, using the tilt method (time 0). The microtiter plate was incubated for 1 hour at 37° C., then each sample was spotted in duplicate on Mueller-Hinton agar plates while the controls were plated using the tilt method (time 1). Agar plates were incubated overnight at 37° C. and the colonies corresponding to time 0 and time 1 (surviving bacteria) were counted. The serum bactericidal titer was defined as the serum dilution resulting in 50% decrease in colony forming units (CFU) per mL, after 60 min incubation of bacteria in the reaction mixture, compared to control CFU per mL at time 0. Typically, bacteria incubated without the test serum in the presence of complement (negative control) showed a 150 to 200% increase in CFU/mL, during the 60 min incubation time. The reference strain for meningococcal serotype A was F8238.

Figure 7:
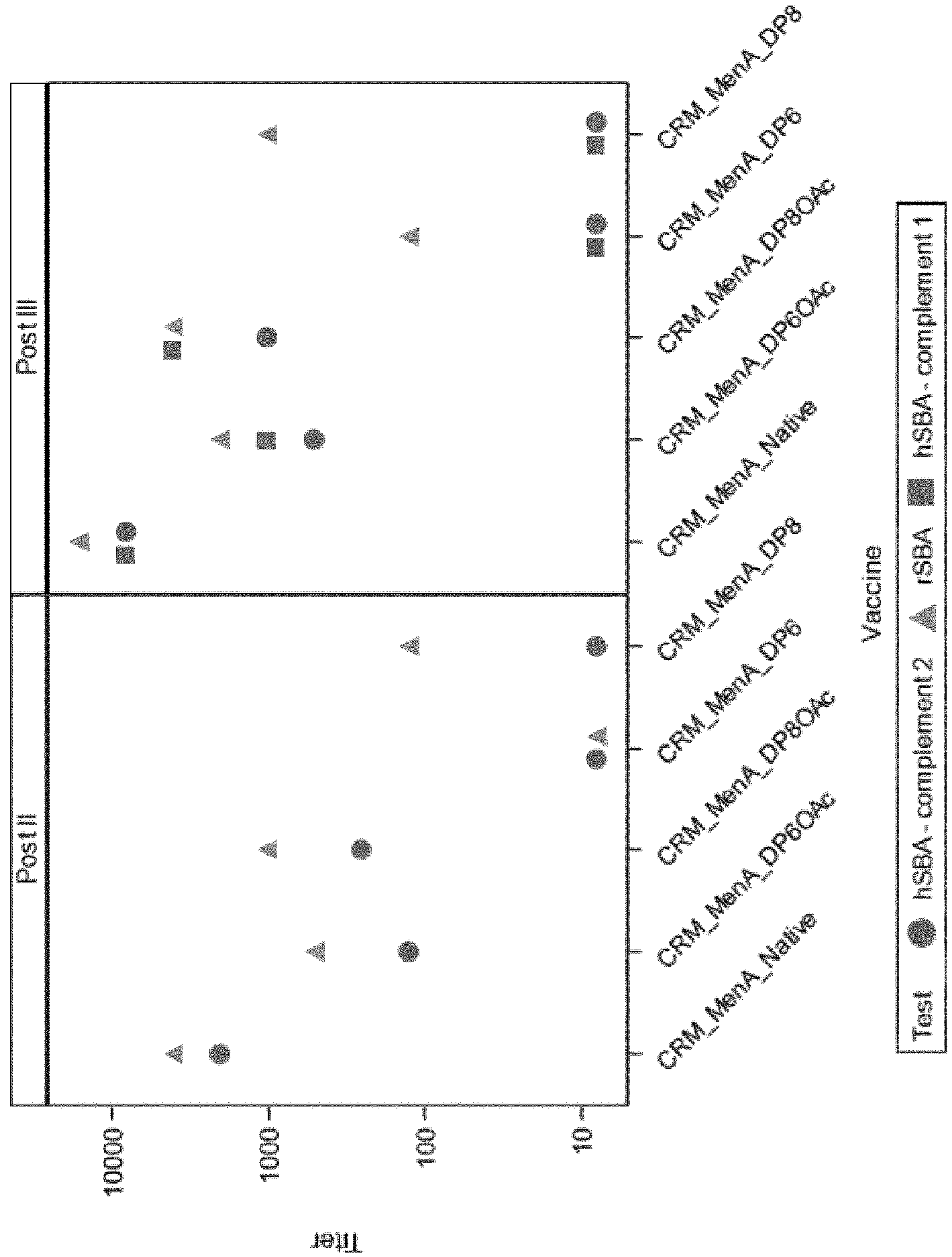
FIG. 7 shows SBA titers post two and three doses of vaccine according to the invention obtained with rabbit (rSBA) and human complement (hSBA).

The results reported in FIG. 7 and Table 4 show the ability of the anti-MenA antibody to be bactericidal against the MenA strain. In particular, the native MenA-$CRM_{197}$ vaccine and the vaccines obtained with the randomly O-acetylated synthetic carba-analogues (Group 2 and Group 3), were able to maintain a significant bactericidal activity also when tested with human complement. FIG. 7 depicts SEA titers post two and three doses obtained with rabbit (rSBA) and human (hSBA) complement.

TABLE 4

| | Group 1 MenA-$CRM_{197}$ Native | Group 2 carbaMenA DP6OAc-$CRM_{197}$ (random OAc) | Group 3 carbaMenA DP8OAc-$CRM_{197}$ (random OAc) | Group 4 carbaMenA DP6-$CRM_{197}$ (no OAc) | Group 5 carbaMenA DP8-$CRM_{197}$ (no OAc) |
|---|---|---|---|---|---|
| Post 2 | | | | | |
| rSBA | 4096 | 512 | 1024 | <16 | 128 |
| hSBA (human complement donor 2) | 2048 | 128 | 256 | <16 | <16 |
| Post 3 | | | | | |
| rSBA | 16384 | 2048 | 4096 | 128 | 1024 |
| hSBA (human complement donor 1) | 8192 | 1024 | 4096 | <16 | <16 |
| hSBA (human complement donor 2) | 8192 | 512 | 1024 | <16 | <16 |

Figure 8:
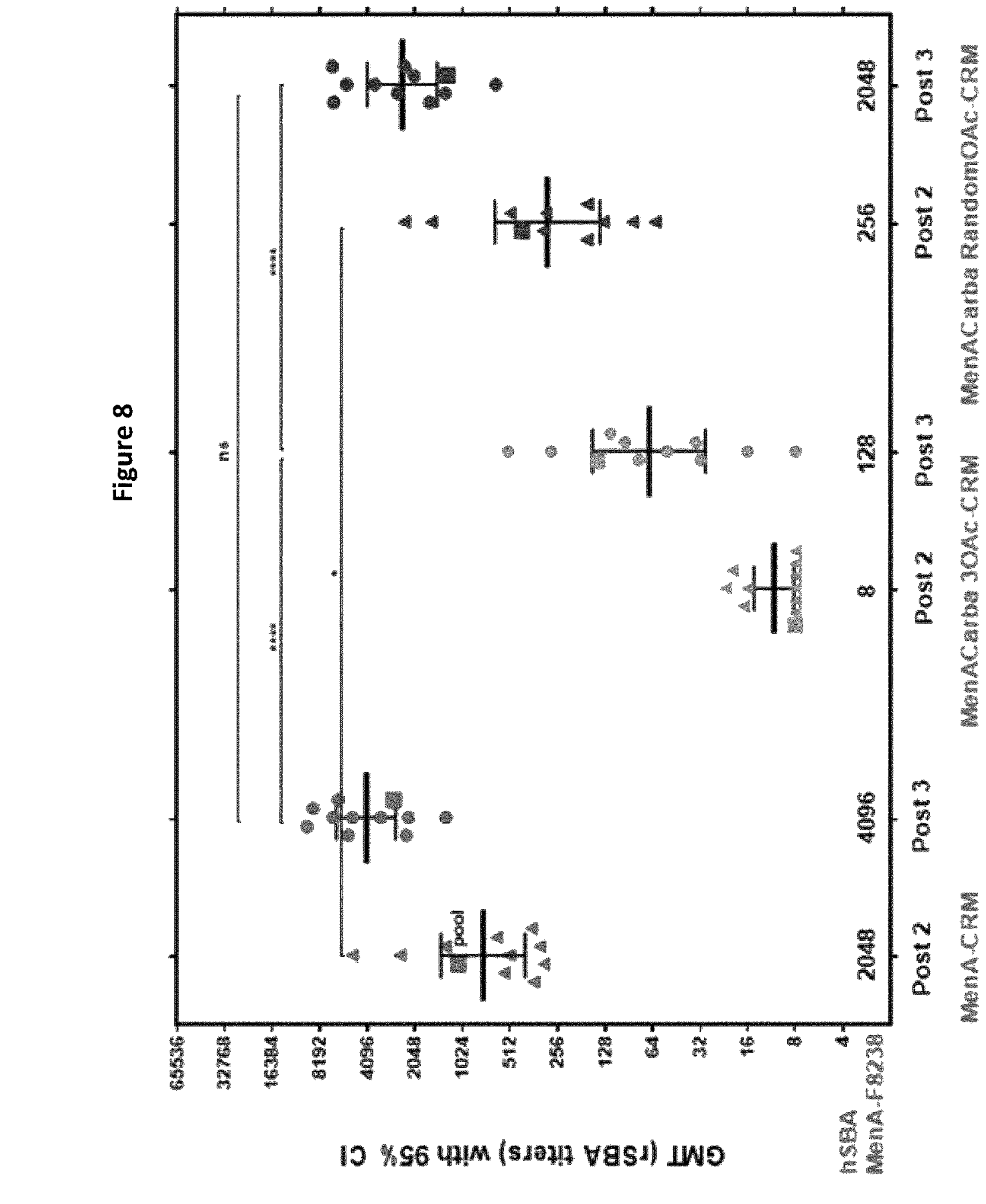
FIG. 8 shows SBA titers post three doses of vaccine: human complement mediated bactericidal titers were measured on sera elicited with the $CRM_{197}$ conjugate of randomly O-acetylated carbaMenA analogue DP8 in comparison with $CRM_{197}$ conjugates of selectively 3-O-acetylated carbaMenA DP8 and with native MenA-$CRM_{197}$ vaccine as the benchmark (i.e. positive control).

FIG. 8 shows human complement mediated serum bactericidal titers elicited by the above said $CRM_{197}$-conjugates of selectively 3-O-acetylated carbaMenA DP8 and the randomly acetylated carbaMenA DP8 of the invention, after three doses. MenA-$CRM_{197}$ vaccine was still the positive control.

The SBA titers induced by the randomly O-acetylated CarbaMenA-$CRM_{197}$ conjugate were statistically comparable to the MenA vaccine benchmark after three doses, while the 3 O-acetylated CarbaMenA-$CRM_{197}$ conjugate induced far lower SBA titers in sera compared to the vaccine benchmark, as measured with both baby rabbit complement and human complement.

Statistical Methods

Non-parametric t test was performed on data obtained from ELISA, Mann-Whitney was conducted applying GraphPad software comparing the rank between two groups of interest (i.e. $CRM_{197}$-MenA avDP15 and $CRM_{197}$-MenA DP6OAc or DP8OAc). ELISA data were reported as geometric mean with 95% of Cl. In addition, an Analysis Of Variance (ANOVA) model was fitted on the log 10 antibody titers including group (all of them except 4 and 5), time and group by time interaction as fixed effects. A heterogeneous variance model was used since identical variances were not assumed between the groups. For each endpoint, this model was used to estimate the group geometric means and their 95% CIs as well as the geometric mean ratios (O-Acetylated formulations vs Benchmark) and 95% CIs. Differently, for SBA data, as there is a single observation for each group at each time point (pools of sera), only a graphical analysis was performed.

Figure 9:
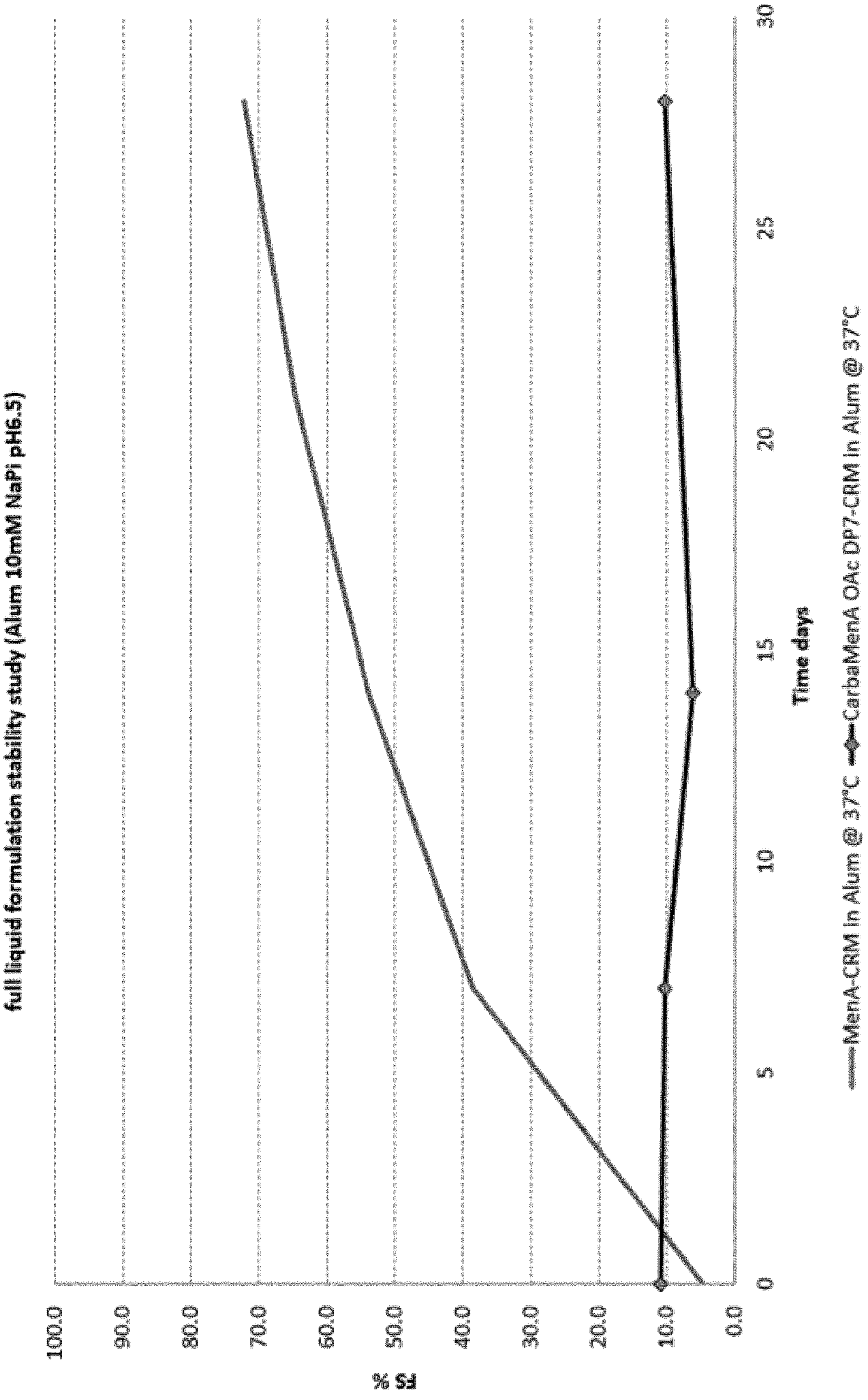
FIG. 9 is a graph comparing stability of MenA-$CRM_{197}$ (i.e. native MenA polysaccharide conjugated to $CRM_{197}$) with an acetylated oligomer of the invention where n is 7 and the oligomer is conjugated to $CRM_{197}$.

Protocol for Quantification of Hydrolyzed MenA and carbaMenA Oligomer in Final Conjugates HPAEC-PAD was used to quantify the amount of monomer released over time from the MenA and carbaMenA conjugates of the invention. Titers reported in the FIG. 9 were obtained by hydrolyzing the samples with HCl at final concentration 6M at 110° C. for 2 hours in dry oven. After incubation samples were dried in as Speedvac system and then re-dissolved with water and filtered 0.45 μm. Quantification was performed by using a standard curve built in the range 0.5-5.0 μg/mL with CarbaMenA DP7, quantified by NMR, and treated as samples. The analysis was performed on a ICS5000 system (Dionex-Themo Fisher) equipped with a CarboPac PA1 column with guard. Elution was made with a gradient of sodium acetate in presence of 100 mM sodium hydroxide at 1.0 mL/min and peak detected in pulse integrated amperometry by using the quadruple wave form for carbohydrates. Results were elaborated with Chromeleon™ 7.2 Chromatography Data System (CDS) Software.

CONCLUSIONS

Based on data obtained, it can be concluded that carba MenA oligomers of the invention can be used for the development of more stable versions of MenA vaccines and the OAc moiety in combination with the oligomer length are key to elicit a functional immune response against MenA strains.

The invention claimed is:

1. An oligomer of Formula (Ia) or (Ib):

(Ia)

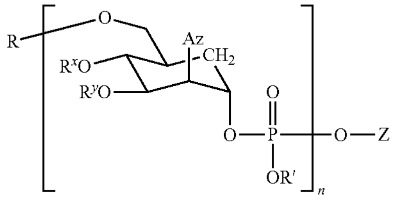

or (Ib)

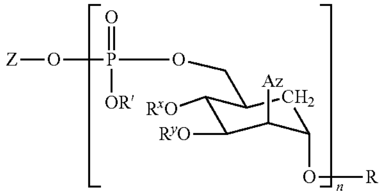

wherein n is ≥6;

R is H or —P(O)(OR")$_2$, wherein R" is H or a pharmaceutically acceptable phosphate counterion;

R' is H or a pharmaceutically acceptable phosphate counterion;

$R^x$ is H or —C(O)$CH_3$ and may be the same or different in each repeat unit;

$R^y$ is H or —C(O)$CH_3$ and may be the same or different in each repeat unit;

wherein at least one of $R^x$ or $R^y$ is —C(O)$CH_3$ in at least one repeat unit, wherein both of $R^x$ and $R^y$ are —C(O)$CH_3$ in at least one same repeat unit; and wherein taken together, about 50 to 90% of $R^x$ and $R^y$ in the oligomer is —C(O)$CH_3$;

Az is an aza substituent selected from the group consisting of —NH(CO)$R^1$, —N($R^1$)$_2$ and —$N_3$, wherein $R^1$ is independently selected from the group consisting of H, a linear or branched $C_1$-$C_6$-alkyl and a linear or branched $C_1$-$C_6$-haloalkyl;

Z is (i) a protecting group, (ii) a functional linker for conjugation to a protein, or (iii) a linear or branched $C_1$-$C_6$ alkyl, optionally substituted phenyl, —C(O) Y, or a linear or branched $C_1$-$C_6$-alkyl-X, wherein Y is H, a linear or branched $C_1$-$C_6$-alkyl or a protecting group, and wherein X is —$NH_2$, —$N_3$, —C≡CH, —CH═$CH_2$, —SH or —S—C≡N.

2. The oligomer of claim 1, which is defined by Formula (Ia).

3. The oligomer of claim 1, wherein n is 8.

4. The oligomer of claim 1, wherein n is 8 to 15.

5. The oligomer according claim 1, wherein Az is —NHC(O)$CH_3$.

6. The oligomer according to claim 1, wherein both of $R^x$ and $R^y$ are —C(O)$CH_3$ in 40 to 50% of the repeat units of the oligomer.

7. The oligomer according to claim 6, wherein in 10 to 30% of the remaining repeat units of the oligomer one of $R^x$ or $R^y$ is —C(O)$CH_3$, the rest of the repeat units in the oligomer having $R^x$═$R^y$═H.

8. An oligomer conjugate antigen of Formula (IIa) or (IIb):

(IIa)

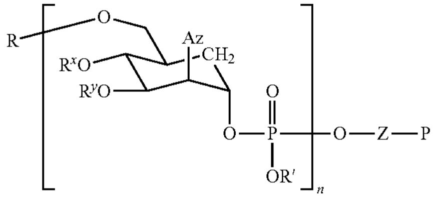

or (IIb)

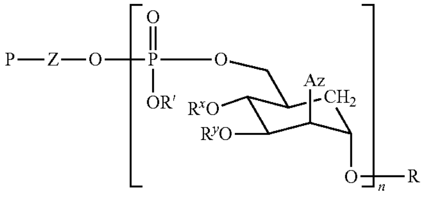

wherein n is ≥6;

R is H or —P(O)(OR")$_2$, wherein R" is H or a pharmaceutically acceptable phosphate counterion;

R' is H or a pharmaceutically acceptable phosphate counterion;

$R^x$ is H or —C(O)$CH_3$ and may be the same or different in each repeat unit;

$R^y$ is H or —C(O)$CH_3$ and may be the same or different in each repeat unit;

wherein at least one of $R^x$ or $R^y$ is —C(O)$CH_3$ in at least one repeat unit, wherein both of $R^x$ and $R^y$ are —C(O)$CH_3$ in at least one same repeat unit; and wherein taken together, about 50 to 90% of $R^x$ and $R^y$ in the oligomer is —C(O)$CH_3$;

Az is an aza substituent selected from the group consisting of —NH(CO)$R^1$, —N($R^1$)$_2$ and —$N_3$, wherein $R^1$ is independently selected from the group consisting of H, a linear or branched $C_1$-$C_6$-alkyl and a linear or branched $C_1$-$C_6$-haloalkyl;

Z is a linker or a bond; and

P is a protein.

9. The conjugate of claim 8, wherein P is an inactivated bacterial toxin selected from diphtheria toxoid (DT), tetanus toxoid (TT), $CRM_{197}$, *E. coli* ST and *Pseudomonas aeruginosa* exotoxin (rEPA), or P is a polyamino acid such as poly(lysine:glutamic acid) or P is hepatitis B virus core protein or SPR96-2021 or *N. meningitidis* serogroup B antigen fHbp-231.

10. The conjugate of claim 8, wherein P is $CRM_{197}$.

11. The conjugate of claim 8, wherein Z is a linker having the following formula:

$$*\text{—}(CH_2)_p\text{—}NH(CO)\text{—}(CH_2)_p\text{—}(X\text{—}(CH_2)_p)_p\text{—}C(O)\text{—}*$$

wherein * represents the point of attachment, and wherein p is independently selected from 1 to 10; and X is selected from —O—, —S— and —NH—; or wherein Z is a linker having the following formula:

$$*\text{—}(CH_2)_m\text{—}NHC(O)\text{—}(CH_2)_m\text{—}C(O)\text{—}*$$

wherein m is independently selected from 1 to 10.

12. A conjugate according to claim 8 having the following structure:

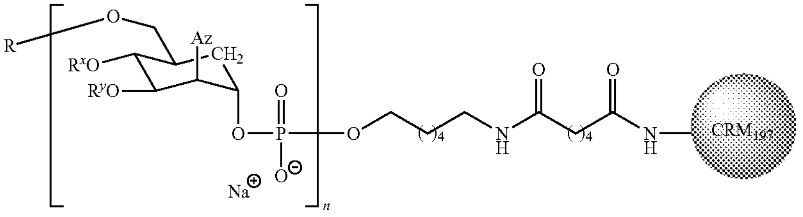

wherein n, R, $R^x$ and $R^y$ are as defined in any one of claims 1 to 8.

13. An immunogenic composition comprising (a) a conjugate according to claim 8; and (b) at least one pharmaceutically acceptable excipient.

14. The immunogenic composition according to claim 13, further comprising an adjuvant.

15. The immunogenic composition according to claim 13, further comprising at least one antigen derived from one of *N. meningitidis* serogroup C, W135, Y and optionally A.

16. An immunogenic composition according to claim 13 for use in the treatment or prevention of Meningitis A, C, W135 or Y.

17. An immunogenic composition according to claim 13 for use in inducing an immune response to Meningitis A, C, W135 or Y.

18. A method for the treatment or prevention of *Meningitidis* A, C, W135 or Y in a subject, the method comprising administering to the subject a therapeutically or prophylactically effective amount of a conjugate according to claim 8.

19. A method of inducing an immune response to Meningitis A, C, W135 or Y in a subject, the method comprising administering to the subject an immunologically effective amount of an immunogenic composition according to claim 13.

20. The oligomer of claim 8, wherein n is 7 to 14.

21. The oligomer of claim 8, wherein n is 8.

22. The oligomer according to claim 8, wherein Az is —NHC (O)$CH_3$.

23. The oligomer according to claim 8, wherein both of Rx and Ry are —C(O)$CH_3$ in 40 to 50% of the repeat units of the oligomer.

24. The oligomer according to claim 23, wherein in 10 to 30% of the remaining repeat units of the oligomer one of $R^x$ or $R^y$ is —C(O)$CH_3$, the rest of the repeat units in the oligomer having $R^x$=$R^y$=H.

* * * * *